United States Patent
Paul et al.

(10) Patent No.: US 11,355,219 B2
(45) Date of Patent: Jun. 7, 2022

(54) GENOTYPE ESTIMATION DEVICE, METHOD, AND PROGRAM

(71) Applicant: Kabushiki Kaisha Toshiba, Tokyo (JP)

(72) Inventors: Topon Paul, Kanagawa (JP); Arika Fukushima, Tokyo (JP); Shinya Umeno, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 546 days.

(21) Appl. No.: 15/419,903

(22) Filed: Jan. 30, 2017

(65) Prior Publication Data

US 2017/0364631 A1    Dec. 21, 2017

Related U.S. Application Data

(63) Continuation of application No. PCT/JP2015/080573, filed on Oct. 29, 2015.

(30) Foreign Application Priority Data

Oct. 30, 2014    (JP) .............................. JP2014-221614

(51) Int. Cl.
*G01N 33/48*    (2006.01)
*G01N 33/50*    (2006.01)
(Continued)

(52) U.S. Cl.
CPC ............. *G16B 20/20* (2019.02); *G16B 20/00* (2019.02); *G16B 30/00* (2019.02); *G16B 40/00* (2019.02); *G16B 20/40* (2019.02)

(58) Field of Classification Search
CPC .......... G16B 20/00; G16B 30/00; G16B 40/00
See application file for complete search history.

(56) References Cited

U.S. PATENT DOCUMENTS 7,127,354 B1    10/2006    Nozaki et al.
7,467,117 B2    12/2008    Kermani
(Continued)

FOREIGN PATENT DOCUMENTS

JP    2004-78371       3/2004
JP    2006-107396      4/2006
(Continued)

OTHER PUBLICATIONS

Southern et al. Analyzing and comparing nucleic acid sequences by hybridization to arrays of oligonucleotides: Evaluation using experimental models. Genomics, vol. 13, pp. 1008-1017. (Year: 1992).*
(Continued)

*Primary Examiner* — Russell S Negin
(74) *Attorney, Agent, or Firm* — Finnegan, Henderson, Farabow, Garrett & Dunner L.L.P.

(57) ABSTRACT

According to one embodiment, a genotype estimation device includes: an acquirer configured to acquire a clustering strength of genotype data of a plurality of specimens including an unknown specimen whose genotype is not known and known specimens whose genotypes are known; and an estimator configured to estimate the genotype of the unknown specimen on the basis of the genotype data in response to the clustering strength being larger than a first threshold, and output an estimation result.

13 Claims, 45 Drawing Sheets

(51) Int. Cl.
*G16B 20/20* (2019.01)
*G16B 20/00* (2019.01)
*G16B 30/00* (2019.01)
*G16B 40/00* (2019.01)
*G16B 20/40* (2019.01)

(56) References Cited

U.S. PATENT DOCUMENTS

| | | | |
|---|---|---|---|
| 8,200,440 B2 | 6/2012 | Hubbell et al. | |
| 2006/0271300 A1* | 11/2006 | Welsh | G06K 9/6226 702/19 |
| 2008/0287308 A1 | 11/2008 | Hubbell et al. | |
| 2010/0094795 A1 | 4/2010 | Irizarry et al. | |
| 2012/0004858 A1 | 1/2012 | Yano et al. | |
| 2013/0054603 A1* | 2/2013 | Birdwell | G06K 9/6253 707/738 |
| 2014/0107933 A1 | 4/2014 | Irizarry et al. | |
| 2014/0153801 A1 | 6/2014 | Sárközy et al. | |

FOREIGN PATENT DOCUMENTS

| | | |
|---|---|---|
| JP | 2007-334719 | 12/2007 |
| JP | 2010-86142 | 4/2010 |
| JP | 2010-218150 | 9/2010 |
| WO | WO-2002/025489 | 3/2002 |
| WO | WO-2009/017204 | 2/2009 |

OTHER PUBLICATIONS

International Search Report dated Dec. 28, 2015, issued by the Japanese Patent Office in counterpart International Application No. PCT/JP2015/080573; 2 pages.

International Preliminary Report on Patentability and Written Opinion issued by The International Bureau of WIPO dated May 11, 2017, for International Application No. PCT/JP2015/080573.

* cited by examiner

| SPECIMEN ID/SNP ID | 01 | 02 | ... | N |
|---|---|---|---|---|
| rs000001 | CG | CC | ... | GG |
| rs000002 | AT | — | ... | TT |
| rs000003 | — | AA | ... | AT |
| ... | ... | ... | ... | ... |
| rs999999 | GG | CG | ... | CC |

GENOTYPE DATA

FIG. 2

| SPECIMEN ID/SNP ID | 01 | | | | 02 | | | | ... | N | | | |
|---|---|---|---|---|---|---|---|---|---|---|---|---|---|
| | x1 | ... | xn | | x1 | ... | xn | | | x1 | ... | xn | |
| rs000001 | 0.8 | ... | 0.5 | | 0.6 | ... | 0.7 | | ... | 0.4 | ... | 0.2 | |
| rs000002 | 0.5 | ... | 0.7 | | 0.4 | ... | 0.6 | | ... | 0.5 | ... | 0.3 | |
| rs000003 | 0.4 | ... | 0.1 | | 0.9 | ... | 0.8 | | ... | 0.8 | ... | 0.7 | |
| ... | ... | ... | ... | | ... | ... | ... | | ... | ... | ... | ... | |
| rs999999 | 0.6 | ... | 0.4 | | 0.2 | ... | 0.3 | | ... | 0.8 | ... | 0.2 | |

SIGNAL INTENSITY DATA

FIG. 3

| CLUSTER ID / SNP ID | 1 | | 2 | | ... | m | |
|---|---|---|---|---|---|---|---|
| | v1 | v2 | v1 | v2 | ... | v1 | v2 |
| rs000001 | 12 | 32 | 24 | 54 | ... | 18 | 20 |
| rs000002 | 23 | 45 | 28 | 32 | ... | 23 | 45 |
| rs000003 | 16 | 43 | 29 | 31 | ... | 53 | 43 |
| ... | ... | ... | ... | ... | ... | ... | ... |
| rs999999 | 20 | 36 | 30 | 25 | ... | 65 | 70 |

CLUSTER COORDINATE DATA

FIG. 4

| SNP ID | CLUSTERING STRENGTH |
|---|---|
| rs000001 | 0.95 |
| rs000002 | 0.78 |
| rs000003 | 0.45 |
| ... | ... |
| rs999999 | 0.64 |

CLUSTERING STRENGTH DATA

FIG. 5

| SNP ID | INTER-CLUSTER DISTANCE 1,2 | INTER-CLUSTER DISTANCE 1,3 | ... | CLUSTERING STRENGTH |
|---|---|---|---|---|
| rs000001 | 0.96 | 0.94 | ... | 0.95 |
| rs000002 | 0.80 | 0.76 | ... | 0.78 |
| rs000003 | 0.40 | 0.50 | ... | 0.45 |
| ... | ... | ... | ... | ... |
| rs999999 | 0.68 | 0.60 | ... | 0.64 |

CLUSTERING STRENGTH DATA

FIG. 6

| SNP ID1 | SNP ID2 | LINKAGE DISEQUILIBRIUM STATISTICAL SCORES | | |
|---|---|---|---|---|
| | | LINKAGE DISEQUILIBRIUM SCORE (D') | CORRELATION COEFFICIENT ($r^2$) | LOGARITHM OF ODDS (LOD) |
| rs125678 | rs129688 | 0.98 | 0.96 | 18.69 |
| ⋮ | ⋮ | ⋮ | ⋮ | ⋮ |
| rs125678 | rs986754 | 0.39 | 0.03 | 0.32 |
| ⋮ | ⋮ | ⋮ | ⋮ | ⋮ |
| rs129688 | rs986754 | 1.00 | 0.05 | 0.75 |
| ⋮ | ⋮ | ⋮ | ⋮ | ⋮ |

LINKAGE DISEQUILIBRIUM STATISTICAL DATA

FIG. 7

| HAPLOTYPE DATA ID/SNP ID | rs123456 | rs623456 | rs987456 | rs987123 | rs598456 | rs387456 | rs912346 | rs778456 | rs873456 | rs987009 |
|---|---|---|---|---|---|---|---|---|---|---|
| refHTD1 | A | T | G | T | C | T | C | A | C | G |
| refHTD2 | G | C | T | T | C | T | C | C | G | G |
| refHTD3 | G | C | T | T | T | G | C | C | G | A |
| refHTD4 | A | T | T | A | C | T | G | A | C | G |
| refHTD5 | A | T | G | A | C | T | G | A | C | G |
| refHTD6 | G | T | T | A | C | T | G | A | C | A |
| ... | ... | ... | ... | ... | ... | ... | ... | ... | ... | ... |

REFERENCE HAPLOTYPE DATA

FIG. 8

| SNP ID | GENOTYPE | FREQUENCY |
|---|---|---|
| rs125678 | CC | 0.42 |
| rs125678 | CT | 0.38 |
| rs125678 | TT | 0.20 |
| ... | ... | ... |

REFERENCE GENOTYPE FREQUENCY DATA

| KNOWN SPECIMEN "Si" | GENOTYPE |
|---|---|
| 1 | AG |
| 2 | GG |
| 3 | AG |
| 4 | AG |
| 5 | AA |

| GENOTYPE | NUMBER OF VOTES |
|---|---|
| AG | 3 |
| GG | 1 |
| AA | 1 |

| KNOWN SPECIMEN "Si" | GENOTYPE | WEIGHT |
|---|---|---|
| 1 | AG | 0.6 |
| 2 | GG | 0.4 |
| 3 | AG | 0.9 |
| 4 | AG | 0.7 |
| 5 | AA | 0.5 |

| GENOTYPE | NUMBER OF VOTES |
|---|---|
| AG | 2.2 |
| GG | 0.4 |
| AA | 0.5 |

| CLUSTER LINE "Ci" | GENOTYPE |
|---|---|
| 1 | AG |
| 2 | GG |
| 3 | AG |
| 4 | AG |
| 5 | AA |

| GENOTYPE | NUMBER OF VOTES |
|---|---|
| AG | 3 |
| GG | 1 |
| AA | 1 |

| SPECIMEN ID/ SNP ID | FOR EVALUATION | | | FOR LEARNING | | |
|---|---|---|---|---|---|---|
| | 01 | ... | 10 | 11 | ... | N |
| rs000001 | CG | ... | CC | CG | ... | GG |
| rs000003 | TT | ... | AA | TA | ... | AT |

FIG. 22

| SPECIMEN ID/ SNP ID | ESTIMATION ACCURACY | | |
|---|---|---|---|
| | k' =1 | k' =3 | k' =5 |
| rs000001 | 0.8 | 0.6 | 0.9 |
| rs000003 | 0.7 | 0.5 | 0.8 |
| ... | ... | ... | ... |

| AVERAGE ESTIMATION ACCURACY | | |
|---|---|---|
| k' =1 | k' =3 | k' =5 |
| 0.75 | 0.55 | 0.85 |
| ... | ... | ... |

| HAPLOTYPE DATA ID/SNP ID | rs123456 | rs623456 | rs987456 | rs987123 | rs598456 | rs387456 | rs912346 | rs778456 | rs873456 | rs987009 |
|---|---|---|---|---|---|---|---|---|---|---|
| HTD1 | A | T | G | A | C | T | G | A | C | — |
| HTD2 | G | C | T | T | T | G | C | C | G | — |

HAPLOTYPE DATA OF UNKNOWN SPECIMEN "S"

FIG. 26

| HAPLOTYPE DATA ID/SNP ID | rs123456 | rs623456 | rs987456 | rs987123 | rs598456 | rs387456 | rs912346 | rs778456 | rs873456 | rs987009 |
|---|---|---|---|---|---|---|---|---|---|---|
| refHTD1 | A | T | G | T | C | T | C | A | C | G |
| refHTD2 | G | C | T | T | C | T | C | C | G | G |
| refHTD3 | G | C | T | T | T | G | C | C | G | A |
| refHTD4 | A | T | T | A | C | T | G | A | C | G |
| refHTD5 | A | T | G | A | C | T | G | A | C | G |
| refHTD6 | G | T | T | A | C | T | G | A | C | A |
| ... | ... | ... | ... | ... | ... | ... | ... | ... | ... | ... |

EXTRACTED REFERENCE HAPLOTYPE DATA

FIG. 27

| HAPLOTYPE DATA ID/SNP ID | rs123456 | rs623456 | rs987456 | rs987123 | rs598456 | rs387456 | rs912346 | rs778456 | rs873456 | rs987009 |
|---|---|---|---|---|---|---|---|---|---|---|
| HTD1 | 1 | 4 | 3 | 1 | 2 | 4 | 3 | 1 | 2 | 1 |
| HTD2 | 3 | 2 | 4 | 4 | 4 | 3 | 2 | 2 | 3 | 1 |

HAPLOTYPE DATA ID/SNP ID

| HAPLOTYPE DATA ID/SNP ID | rs123456 | rs623456 | rs987456 | rs987123 | rs598456 | rs387456 | rs912346 | rs778456 | rs873456 | rs987009 |
|---|---|---|---|---|---|---|---|---|---|---|
| refHTD1 | 1 | 4 | 3 | 4 | 2 | 4 | 2 | 1 | 2 | 3 |
| refHTD2 | 3 | 2 | 4 | 4 | 2 | 4 | 2 | 2 | 3 | 3 |
| refHTD3 | 3 | 2 | 4 | 4 | 4 | 3 | 2 | 2 | 3 | 1 |
| refHTD4 | 1 | 4 | 4 | 1 | 2 | 4 | 3 | 1 | 2 | 3 |
| refHTD5 | 1 | 4 | 3 | 1 | 2 | 4 | 3 | 1 | 2 | 3 |
| refHTD6 | 3 | 4 | 4 | 1 | 2 | 4 | 3 | 1 | 2 | 1 |
| ... | ... | ... | ... | ... | ... | ... | ... | ... | ... | ... |

HAPLOTYPE DATA OF UNKNOWN SPECIMEN "S"

FIG. 29

| SPECIMEN ID/SNP ID | 01 | 02 | ... | N | |
|---|---|---|---|---|---|
| rs000001 | CG | CC | ... | GG | Fullcall SNP |
| rs000002 | AT | — | ... | TT | Nocall SNP |
| rs000003 | — | AA | ... | AT | Nocall SNP |
| ... | ... | ... | ... | ... | |
| rs999999 | GG | CG | ... | CC | Fullcall SNP |

GENOTYPE DATA

| SPECIMEN ID/SNP ID | 01 | 02 | ... | N |
|---|---|---|---|---|
| rs000001 | CG | CC | ... | GG |
| rs000002 | AT | — | ... | TT |
| rs000003 | — | AA | ... | AT |
| ... | ... | ... | ... | ... |
| rs999998 | CC | CC | ... | CC |
| rs999999 | GG | CG | ... | CC |

GENOTYPE DATA

| SPECIMEN ID/SNP ID | 01 | 02 | ... | N |
|---|---|---|---|---|
| rs000001 | 0.8 | 0.6 | ... | 0.4 |
| rs000002 | 0.5 | 0.4 | ... | 0.5 |
| rs000003 | 0.4 | 0.9 | ... | 0.8 |
| ... | ... | ... | ... | ... |
| rs999998 | 0.3 | 0.1 | ... | 0.6 |
| rs999999 | 0.6 | 0.2 | ... | 0.8 |

SIGNAL INTENSITY DATA (x1)

FIG. 38

| SPECIMEN ID/SNP ID | 01 | 02 | ... | N |
|---|---|---|---|---|
| rs000001 | 1 | 2 | ... | 0 |
| rs000002 | 1 | -1 | ... | 2 |
| rs000003 | -1 | 0 | ... | 1 |
| ... | ... | ... | ... | ... |
| rs999998 | 0 | 0 | ... | 0 |
| rs999999 | 2 | 1 | ... | 0 |

GENOTYPE DATA (AFTER SUBSTITUTION)

| SPECIMEN ID/SNP ID | 01 | 02 | ... | N |
|---|---|---|---|---|
| rs000001 | 0.8 | 0.6 | ... | 0.4 |
| ... | ... | ... | ... | ... |
| rs999998 | 0.3 | 0.1 | ... | 0.6 |
| rs999999 | 0.6 | 0.2 | ... | 0.8 |

SIGNAL INTENSITY DATA (x1) OF Fullcall SNP

| SPECIMEN ID/SNP ID | 01 | 02 | ... | N |
|---|---|---|---|---|
| ... | ... | ... | ... | ... |
| rs999998 | 0.3 | 0.1 | ... | 0.6 |

SIGNAL INTENSITY DATA (x1) OF SINGLE-CLUSTER SNP

| SPECIMEN ID/SNP ID | 01 | 02 | ... | N |
|---|---|---|---|---|
| rs000001 | 0.8 | 0.6 | ... | 0.4 |
| ... | ... | ... | ... | ... |
| rs999999 | 0.6 | 0.2 | ... | 0.8 |

SIGNAL INTENSITY DATA (x1) OF MULTIPLE-CLUSTER SNP

FIG. 42

| GENOTYPE | 2 | 1 | 0 |
|---|---|---|---|
| MINIMUM VALUE | -6.29 | -2.11 | -0.80 |
| AVERAGE VALUE | -1.79 | -0.66 | 2.33 |
| MAXIMUM VALUE | 0.69 | 2.11 | 7.46 |
| STANDARD DEVIATION VALUE | 1.15 | 0.97 | 1.83 |

STATISTICAL VALUES OF SIGNAL INTENSITY DATA $x_1$
OF SINGLE-CLUSTER SNP

| GENOTYPE | 2 | 1 | 0 |
|---|---|---|---|
| MINIMUM VALUE | -6.31 | -3.33 | -0.89 |
| AVERAGE VALUE | -1.75 | 0.32 | 2.35 |
| MAXIMUM VALUE | 2.06 | 3.76 | 6.53 |
| STANDARD DEVIATION VALUE | 1.63 | 1.17 | 2.12 |

STATISTICAL VALUES OF SIGNAL INTENSITY DATA $x_1$
OF MULTIPLE-CLUSTER SNP

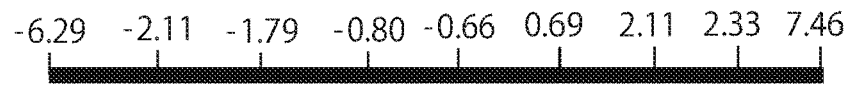
THRESHOLD CANDIDATE LIST OF SINGLE-CLUSTER SNP
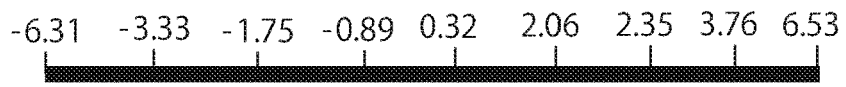
THRESHOLD CANDIDATE LIST OF MULTIPLE-CLUSTER SNP
FIG. 45
| THRESHOLD COMBINATION | $x_l$ | $x_r$ |
|---|---|---|
| 1 | -6.29 | 7.46 |
| 2 | -6.29 | 2.33 |
| ... | ... | ... |
| 24 | -0.80 | 2.11 |
| ... | ... | ... |
| 36 | -0.80 | -0.66 |
THRESHOLD COMBINATION LIST
FIG. 46
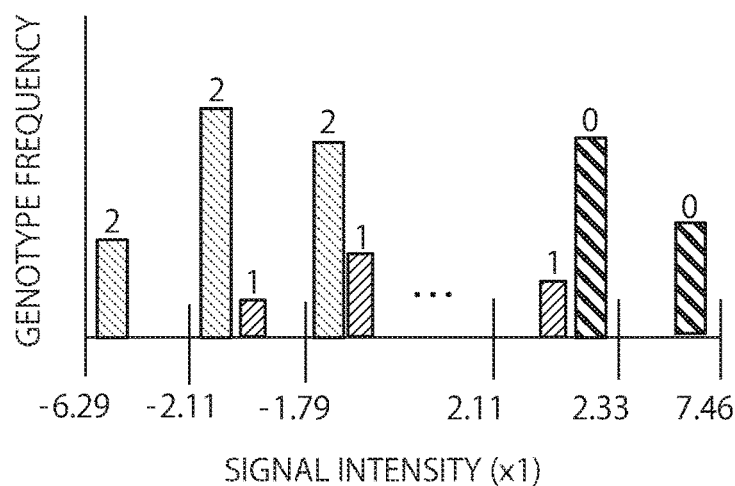
FIG. 47

| THRESHOLD COMBINATION | $x_l$ | $x_r$ | EVALUATED VALUE |
|---|---|---|---|
| 1 | -6.29 | 7.46 | 0.80 |
| 2 | -6.29 | 2.33 | 0.82 |
| ... | ... | ... | ... |
| 24 | -0.80 | 2.11 | 0.97 |
| ... | ... | ... | ... |
| 36 | -0.80 | -0.66 | 0.85 |

THRESHOLD COMBINATION LIST

GENOTYPE ESTIMATION DEVICE, METHOD, AND PROGRAM

CROSS REFERENCE TO RELATED APPLICATIONS

This application is a Continuation of International Application No. PCT/JP2015/080573, filed on Oct. 29, 2015, the entire contents of which is hereby incorporated by reference.

FIELD

Embodiments of the present invention relate to a genotype estimation device, a genotype estimation device method, and a genotype estimation device program.

BACKGROUND

A gene retains genetic information that has significant impacts upon the appearance and constitution of a person who has the gene. Deoxyribonucleic acid (DNA) holds the information of the gene within the body of the person. DNA of various living organisms has a double-helical structure that excels in its ability of autonomous replication for growth and retention of structural strength, and thus holds genetic information in a double-stranded DNA.

Four units called "base" are arranged in one DNA and DNA holds the genetic information in the form of a base sequence. The four bases are adenine (A), thymine (T), cytosine (C), and guanine (G). Combinations of these four represent the differences in the living organisms. In the double-stranded DNA, a base of one DNA corresponds in a complementary manner to a base of another DNA such that an adenine (A) at a certain location with reference to one DNA corresponds to a thymine (T) in another DNA, a cytosine (C) to a guanine (G), and so forth. Also, the number of bases (base pair) constituting a biological body differ from one living organism to another. For example, human DNA is constituted by approximately three billion base pairs.

In typical cases, depending upon the biological species, the number of bases is the same within one biological species, and the 99 percent of the base sequence is common. The sequence varies depending on individuals, and in the base sequence, there is a location of the same biological species and the same DNA where one base is different. The difference of this one base is called single nucleotide polymorphism (SNP). SNP refers to a portion where one particular base in a base sequence differs from one person to another, which is a kind of variant. The combination pattern of the base sequence (alleles) at a gene locus of a certain SNP is called genotype. The genotype of the SNP is related to personal appearance and constitution, the level of risk of a particular disease, effectiveness of a medicine, and development of a side effect of a medicine.

In view of this, the study of genome-wide association study (GWAS) has been gathering much attention, according to which individual genotypes of multiple persons are exhaustively analyzed, making it possible to identify highly-relevant SNPs in terms of diseases and medicines. For example, a common variant in DNA of a commonplace disease is obtained and the difference in genotypes between the group of patients of this disease and the group of healthy persons are exhaustively analyzed for the entire gene region, and thus highly-relevant SNPs are identified. Amongst others, the important key to the future development of the GWAS study is the technology of the genotyping that is capable of determining the genotypes of multiple persons with high throughputs.

Traditionally, as such a genotyping technology, DNA microarray technology has been proposed. DNA microarray technology is a genotype determination technology according to which genotypes of the SNPs (tag SNPs) in the order of several tens of thousands to several hundreds of thousand covering almost all of the entire genome information of multiple persons are allowed to be determined at once with high throughputs.

According to the DNA microarray technology, unknown base sequence of a specimen is hybridized with a known base sequence near a certain SNP used as a probe to measure the fluorescence intensity, the fluorescence intensities of multiple specimens are mapped in a cluster space and subjected to the clustering, and thereby the genotype of this SNP is determined. This draws on the fact that in each SNP, the values of the two types of the fluorescence intensities each reflecting the information of the genotypes form a cluster where they gather on a per-genotype basis in the space.

After carrying out the clustering, clustering strength is also calculated as the degree of confidence of the clustering. The clustering strength becomes higher when the genotypes of the specimen groups are conspicuously separated from each other and more noticeable groups of genotypes can be observed. However, it is difficult for existing clustering techniques to accurately assign the genotype to a specimen having a fluorescence intensity deviated from the observed group, so that, as the case may be, a threshold is specified for the cluster strength so as not to assign a genotype to a less reliable specimen.

BRIEF DESCRIPTION OF THE DRAWINGS

FIG. 2 is a diagram illustrating exemplary genotype data;

FIG. 3 is a diagram illustrating exemplary signal intensity data;

FIG. 4 is a diagram illustrating exemplary cluster coordinate data;

FIG. 5 is a diagram illustrating exemplary clustering strength data;

FIG. 6 is a diagram for explanation of a calculation method of calculating a clustering strength;

FIG. 7 is a diagram illustrating exemplary linkage disequilibrium statistical data;

FIG. 8 is a diagram illustrating exemplary reference haplotype data;

FIG. 22 is a diagram illustrating examples of a specimen for use in estimation and a specimen for use in learning;

FIG. 26 is a diagram illustrating exemplary haplotype data of the unknown specimen;

FIG. 27 is a diagram for explanation of a selection method to select reference haplotype data;

FIG. 29 is a diagram for explanation of a selection method to select reference haplotype data;

FIG. 38 is a diagram illustrating exemplary genotype data;

FIG. 42 is a diagram illustrating exemplary signal intensity data of single-cluster and multiple-cluster SNPs;

FIG. 45 is a diagram illustrating an exemplary threshold candidate list;

FIG. 46 is a diagram illustrating an exemplary threshold combination list;

FIG. 47 is a diagram illustrating an exemplary genotype frequency of a single-cluster SNP;

DETAILED DESCRIPTION

Embodiments of the present invention are described below with reference to the drawings.

First Embodiment

Figure 1:
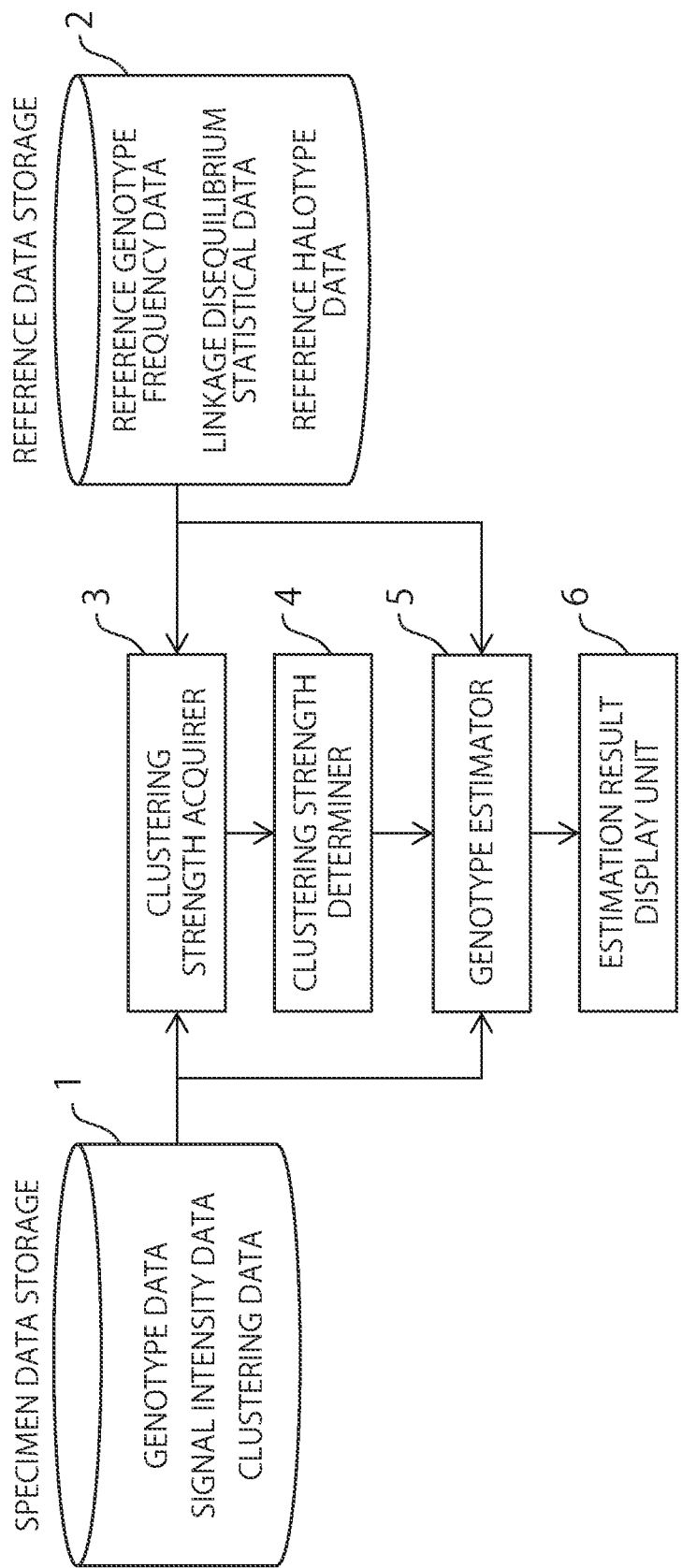
FIG. 1 is a block diagram illustrating functional features of a genotype estimation device in accordance with a first embodiment.

A first embodiment is described with reference to FIGS. 1 to 33. First, the functional features of a genotype estimation device (hereinafter referred to as "estimation device") in accordance with this embodiment are described with reference to FIGS. 1 to 9. FIG. 1 is a block diagram that illustrates the functional features of the estimation device in accordance with this embodiment. As illustrated in FIG. 1, the estimation device includes a specimen data storage 1, a reference data storage 2, a clustering strength acquirer 3, a clustering strength determiner 4, a genotype estimator 5, and an estimation result display unit 6.

The specimen data storage 1 is configured to store data ("specimen data") regarding specimens whose genotypes are already determined by the DNA microarray technology.

The specimen data includes, by way of example and is not limited to, genotype data, signal intensity data, and clustering data.

The genotype data includes pieces of data indicative of respective determination results of the genotypes by the DNA microarray technology. The genotype data includes genotypes that have been determined for each specimen and for each SNP.

FIG. 2 is a diagram that illustrates an example of the genotype data. The genotype data of FIG. 2 includes the determination results of the genotypes of SNPs "rs000001" to "rs9999999" of specimens 01 to N. For example, the genotype of SNP "rs000001" of the specimen "01" is identified as "CG" in FIG. 2.

Still referring to FIG. 2, the symbol "—" indicates the fact that the genotype could not be determined by the DNA microarray technology. The estimation device estimates a genotype like this which could not be determined by the DNA microarray technology.

In the following description, with regard to a certain SNP, a specimen whose genotype is known, i.e., a specimen whose genotype has been determined by the DNA microarray technology is referred to as "known specimen." Also, with regard to a certain SNP, a specimen whose genotype is not known, i.e., a specimen whose genotype could not be determined by the DNA microarray technology is referred to as "unknown specimen." For example, with regard to the SNP "rs000002" of FIG. 2, the specimen "01" is a known specimen whilst the specimen "02" is an unknown specimen.

The signal intensity data includes pieces of data indicative of measurement results of respective signal intensities by the DNA microarray technology. The signal intensity includes, by way of example and is not limited to, measured values of fluorescence intensity, current, and voltage. Also, the signal intensity may be any appropriate parameter calculated from any one of these measured values. The signal intensity data includes respective values of signal intensities in the respective SNPs of the respective specimens.

FIG. 3 is a diagram that illustrates an example of the signal intensity data. The signal intensity data of FIG. 3 includes the values of the signal intensities x1 to xn of the SNPs "rs000001" to "rs9999999" of the specimens "01" to "N." For example, the signal intensity "x1" of the SNP "rs000001" of the specimen "01" is 0.8 in FIG. 3.

The signal intensity data of FIG. 3 includes the values of "n" types of the signal intensities. Although "n" can be specified as appropriate, it is in most cases "2." If n=2, then measured values "A" and "B" of two types of fluorescence intensities can be used as the signal intensities "x1" and "x2." Also, parameters which are calculated from the measured values "A" and "B," respectively, may be used as the signal intensities "x1" and "x2," respectively.

[Expression 1]

$$x1 = \log A - \log B \quad (1)$$

$$x2 = \tfrac{1}{2}(\log A + \log B) \quad (2)$$

When the measured values "A" and "B" of the fluorescence intensities are converted in this manner, the signal intensities can be readily mapped into a cluster space.

The clustering data includes pieces of data indicative of results of clustering performed on a per-SNP basis at the time of determining the genotype by the DNA microarray technology. The clustering by the DNA microarray technology may be hierarchical clustering or non-hierarchical clustering. In the following description, it is assumed that the clustering by the DNA microarray technology is non-hierarchical clustering. The clustering data includes, by way of example and is not limited to, cluster coordinate data and clustering strength data.

Since each cluster corresponds to each genotype in the SNP, the number of clusters to be generated corresponds to the number of the genotypes. For example, if three genotypes of a certain SNP are given as CC, CT, TT, then three clusters are generated in the cluster space. The coordinates of a cluster are, for example, coordinates of the center of gravity of the cluster.

FIG. 4 is a diagram that illustrates an example of the cluster coordinate data. The cluster coordinate data of FIG. 4 includes the coordinates of the clusters "1" to "m" of the SNPs "rs000001" to "rs999999." The coordinates of each cluster are represented by two axes "v1" and "v2" in the cluster space. For example, the coordinates of the cluster 1 in the SNP "rs000001" is given as (v1,v2)=(12,32). It should be noted that the cluster coordinate data may include the coordinates of each specimen in the cluster space as well as the coordinates of each cluster. Also, "vn=xn" is also possible. In this case, the cluster space will be an n-dimensional space of the signal intensities "x1" to "xn."

The clustering strength data includes pieces of data indicative of clustering strengths of the respective SNPs. The clustering strength is an indicator that indicates the degree of confidence of the clustering. A larger clustering strength indicates a higher degree of confidence of the clustering.

FIG. 5 is a diagram that illustrates an example of the clustering strength data. The clustering strength data of FIG. 5 includes the clustering strengths of the SNPs "rs000001" to "rs9999999." For example, the clustering strength of SNP "rs000001" is 0.95 in FIG. 5.

As the clustering strength, for example, an average value of the distances between the clusters can be used. In this case, the clustering strength can be obtained based on the cluster coordinate data in accordance with the following expressions.

[Expression 2]

$$\text{Inter-cluster distance } ij = \sqrt{(vi1 - vj1)^2 + (vi2 - vj2)^2} \quad (3)$$

$$\text{Clustering strength} = \frac{1}{m(m-1)/2} \sum_{i=1}^{m-1} \sum_{j=i+1}^{m} \text{Inter-cluster distance } ij \quad (4)$$

In the above expression (3), the inter-cluster distance "ij" is a Euclidean distance between any two clusters "i" and "j," "(vi1,vi2)" is the coordinates of the center of gravity of the cluster "i", and "(vj1,vj2)" is the coordinates of the center of gravity of the cluster "j." Also, in the above expression (4), "m" is the number of the clusters.

Here, FIG. 6 is a diagram that illustrates the clustering strength data generated from the cluster coordinate data of FIG. 4. Referring to FIG. 6, the inter-cluster distance "ij" and the clustering strength are standardized such that the clustering strength takes a value not less than 0 and not more than 1.

The reference data storage 2 is configured to store known data (reference data) regarding SNPs. The reference data includes, by way of example and is not limited to, linkage disequilibrium statistical data, reference haplotype data, and reference genotype frequency data. As sources of the reference data, large-scale project data of International HapMap Project, 1000 Genomes Project, and the like can be used.

The linkage disequilibrium statistical data (hereinafter referred to as "LD data") includes pieces of data indicative of correlations between SNPs. FIG. 7 is a diagram that illustrates an example of the LD data. The LD data of FIG. 7 includes the scores between the SNPs "rs125678" and "rs129688," the scores between the SNPs "rs125678" and "rs986754," and the scores between the SNPs "rs129688" and "rs986754." The scores are indicators that indicate the strength of correlations between SNPs. The LD data of FIG. 7 includes, as the scores, the linkage disequilibrium score (D'), coefficient of correlation ($r^2$), and logarithm of odds (LOD). For example, with regard to the SNPs "rs125678" and "rs129688" in FIG. 7, the linkage disequilibrium score is 0.98, the coefficient of correlation is 0.96, and the logarithm of odds is 18.69.

The reference haplotype data includes pieces of data indicative of combinations of either of the alleles (bases) of SNPs statistically related on the same chromosome. Specifically, each piece of the reference haplotype data indicates the combination of highly probable bases in some SNPs. The SNP included in the reference haplotype data is selected, for example, on the basis of the LD data.

FIG. 8 is a diagram that illustrates an example of the reference haplotype data. The reference haplotype data of FIG. 8 includes the pieces of the reference haplotype data "refHTD1" to "refHTD6." The respective pieces of the reference haplotype data include the alleles of the SNPs "rs123456," "rs623456," "rs987456," "rs987123," "rs598456," "rs387456," "rs912346," "rs778456," "rs873456," and "rs987009." For example, the allelic gene of SNP "rs123456" of the reference haplotype data "refHTD1" is "A" in FIG. 8.

Figures 9, 10:
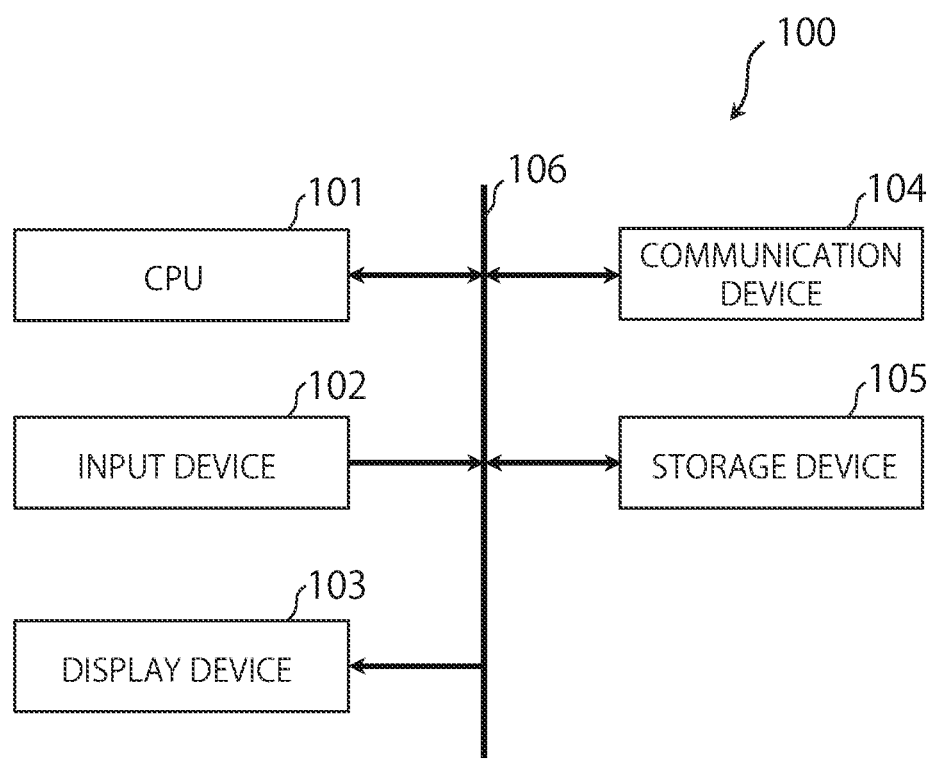
FIG. 9 is a diagram illustrating exemplary reference genotype frequency data.
FIG. 10 is a block diagram of a hardware configuration of the genotype estimation device of FIG. 1.

The reference genotype frequency data includes pieces of data indicative of the genotype frequencies (reference genotype frequency) of the respective SNPs in a certain population. FIG. 9 is a diagram that illustrates an example of the reference genotype frequency data. The reference genotype frequency data of FIG. 9 includes the frequencies of the genotypes "CC," "CT," and "TT" of the SNP "rs125678." In FIG. 9, the allelic gene of the SNP "rs125678" is either "C" or "T." Also, the sum of the frequencies of the respective genotypes becomes 1. For example, in FIG. 9, the frequency of the genotype "CC" of the SNP "rs125678" is 0.42.

The clustering strength acquirer 3 (hereinafter referred to as "acquirer 3") is configured to acquire the clustering strengths of the respective SNPs. If the specimen data includes such clustering strength data as illustrated in FIG. 5, the acquirer 3 acquires the clustering strength data from the specimen data storage 1.

Also, if the specimen data includes such cluster coordinate data as illustrated in FIG. 4, the acquirer 3 may acquire the cluster coordinate data from the specimen data storage 1 and calculate clustering strengths of the respective SNPs on the basis of the cluster coordinate data. The calculation method to calculate the clustering strength has already been described in the foregoing description.

Further, if the specimen data includes such genotype data as illustrated in FIG. 2 and the reference data includes such reference genotype frequency data as illustrated in FIG. 9, then the acquirer 3 may acquire the genotype data from the specimen data storage 1, acquire the reference genotype frequency data from the reference data storage 2, and calculate clustering strengths of the respective SNPs on the basis of the genotype data and the reference genotype frequency data. The calculation method to calculate the clustering strength is described below.

First, the acquirer 3 calculates the frequencies (DNA microarray genotype frequency) of the respective genotypes of the respective SNPs on the basis of the genotype data. The DNA microarray genotype frequency is the frequency of the genotype that has been determined by the DNA microarray technology.

Next, the acquirer 3 calculates the clustering strengths of the respective SNPs on the basis of the DNA microarray genotype frequency and the reference genotype frequency in accordance with the following expression.

[Expression 3]

$$\text{Clustering strength} = 1 - \sqrt{\frac{\sum_{i=1}^{m}(f_{i,r} - f_{i,D})^2}{m}} \quad (5)$$

In the above expression (5), "m" is the number of the genotypes, "$f_{i,r}$" is a reference genotype frequency of the "genotype i," and "$f_{i,D}$" is the DNA microarray genotype frequency of the "genotype i." Since the genotype frequency indicates a probability of each genotype, the sum of "$f_{i,r}$" and the sum of "$f_{i,r}$" are both 1.

For example, if the genotypes of a certain SNP are "CC," "CT," and "TT," the reference genotype frequencies are 0.5, 0.3, and 0.2, respectively, and the DNA microarray genotype frequencies are 0.4, 0.4, and 0.2, respectively, then the clustering strength of this SNP is calculated as 0.92 (=1−sqrt(((0.5−0.4)$^2$+(0.3−0.4)$^2$+(0.2−0.2)$^2$)/3)) in accordance with the above expression (5).

The clustering strength determiner 4 (hereinafter referred to as "determiner 4") compares the clustering strengths for the respective SNPs acquired by the acquirer 3 with a threshold "θ1" (first threshold) and a threshold θ2 (the second threshold). The thresholds "θ1" and "θ2" (θ1≥θ2) are values specified in advance to determine the degree of confidence of clustering by the DNA microarray technology. The determiner 4 determines that the degree of confidence of the clustering is high if the clustering strength is higher than the threshold θ1, determines that the degree of confidence of the clustering is low if it is lower than the threshold θ2, and determines that the degree of confidence of the clustering is at an intermediate level if the clustering strength is not lower than the threshold θ2 and not higher than the threshold θ1. The thresholds θ1 and θ2 depend on the clustering strength. If the clustering strength takes a value in the range of not lower than 0 and not higher than 1, then the clustering strength is identified as a value in the range of not less than 0 and not larger than 1. For example, if the clustering strength is not lower than 0 and not higher than 1, then the thresholds θ1 and θ2 are specified as 0.8 and 0.4, respectively.

Although the following description describes a case where θ1>θ2, another case where θ1=θ2 is also possible. In the latter case, the determiner 4 determines that the degree of confidence is high if the clustering strength is higher than the threshold θ1 and determines that the degree of confidence is low if it is equal to or lower than the threshold θ1.

The genotype estimator 5 (hereinafter referred to as "the estimator 5") estimates the genotype in each SNP of an unknown specimen of the genotype data. For example, the estimator 5 estimates the genotype of the SNP "rs000003" of the specimen "01" in the genotype data of FIG. 2 and the genotype of the SNP "rs000002" of the specimen "02."

The estimator 5 selects the estimation method on the basis of the determination result of the degree of confidence of the clustering by the determiner 4. For example, when the clustering strength is higher than the threshold θ1, i.e., when the degree of confidence of the clustering by the DNA microarray technology is high, then the estimator 5 estimates the genotype by a k-nearest neighbor algorithm on the basis of the genotype data. Also, when the clustering strength is lower than the threshold θ2, i.e., when the degree of confidence of the clustering by the DNA microarray technology is low, then the estimator 5 estimates the genotype by an imputation algorithm on the basis of the genotype data and the reference data. Further, when the clustering strength is not lower than the threshold θ2 and not higher than the threshold θ1, i.e., when the degree of confidence of the clustering by the DNA microarray technology is at an intermediate level, then the estimator 5 estimates the genotype by using both the k-nearest neighbor algorithm and the imputation algorithm. The estimator 5 then outputs the estimation result. The specific examples of the estimation method to estimate the genotype will be described later in detail.

The estimation result display unit 6 (hereinafter referred to as "display unit 6") displays the estimation result obtained by the estimator 5. The display unit 6 may display genotype data and various pieces of information used in the course of the estimation along with the estimation result.

Next, the hardware configuration of the estimation device in accordance with this embodiment is described with reference to FIG. 10. The estimation device in accordance with this embodiment is constituted, as illustrated in FIG. 10, by a computer 100. The computer 100 includes a central processing unit (CPU) 101, an input device 102, a display device 103, a communication device 104, and a storage device 105, which are interconnected via a bus 106.

The CPU 101 is a control device and an arithmetic device of the computer 100. The CPU 101 performs arithmetic processing on the basis of the data and programs input from the individual devices interconnected thereto via the bus 106 (e.g., the input device 102, the communication device 104, and the storage device 105) and outputs arithmetic results and control signals to the individual devices connected thereto via the bus 106 (e.g., the display device 103, the communication device 104, and the storage device 105). The CPU 101 is configured to execute the operating system (OS) of the computer 100, the genotype estimation program (hereinafter referred to as "estimation program"), and the like, and controls the individual devices constituting the computer 100. The estimation program is a program that causes the computer 100 to realize the above-described individual functional features of the estimation device. The computer 100 functions as the estimation device when the CPU 101 executes the estimation program.

The input device 102 is a device for inputting information in the computer 100. The input device 102 may include, by way of example and is not limited to, a keyboard, a mouse, and a touch panel. A user can enter information such as the thresholds θ1 and θ2 by using the input device 102.

The display device 103 is a device that displays images, videos, and the like on the basis of the data, etc. output from the CPU 101. The display device 103 includes, by way of example and is not limited to, a liquid crystal display (LCD), a cathode-ray tube (CRT), and a plasma display panel (PDP). The display unit 6 can be configured using the display device 103.

The communication device 104 is a device for the computer 100 to perform communications in a wired or wireless manner with an external device. The communication device 104 includes, by way of example and is not limited to, a modem, a hub, and a router. The pieces of information such as the specimen data and the reference data may be entered via the communication device 104 from an external device. Also, the communication device 104 is capable of transmitting data such as arithmetic results, etc. output from the CPU 101 to an external device.

The storage device 105 is a storage medium that stores therein the OS of the computer 100, the estimation program, data necessary to run the estimation program, data generated by execution of the estimation program, and the like. The storage device 105 includes a main storage device and an external storage device. The main storage device includes, by way of example and is not limited to, RAM, DRAM, and SRAM. Also, the external storage device includes, by way of example and is not limited to, a hard disk, an optical disc, flash memory, and a magnetic tape. The specimen data storage 1 and the reference data storage 2 can be configured using the storage device 105.

It should be noted that one or more of the computer 100, the CPU 101, the input device 102, the display device 103, the communication device 104, and the storage device 105 may be provided. Also, peripheral devices such as a printer and a scanner may be connected to the computer 100.

Also, the estimation device may be configured by one single computer 100 or may be configured as a system constituted by multiple interconnected computers 100.

Further, the estimation program may be stored in advance in the storage device 105 of the computer 100, stored in a storage medium such as a CD-ROM, or uploaded onto the Internet. In any case, the estimation device can be configured by installing the estimation program on the computer 100 and executing the estimation program.

Figure 11:
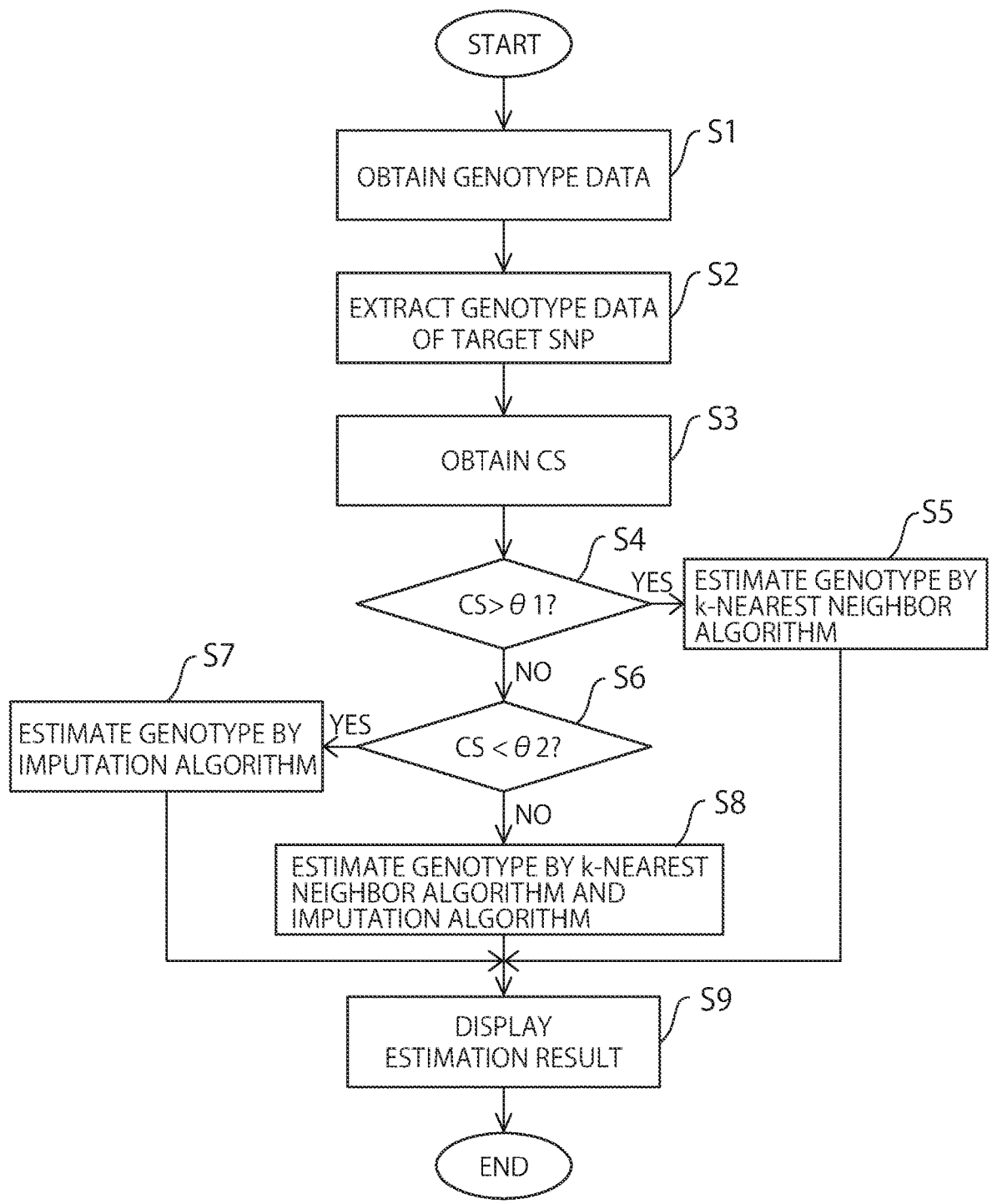
FIG. 11 is a flowchart illustrating an outline of operation of the genotype estimation device of FIG. 1.

Next, the operation of the estimation device in accordance with this embodiment is described below with reference to FIGS. 11 to 30. FIG. 11 is a flowchart that illustrates an outline of the operation of the estimation device in accordance with this embodiment.

In step S1, the acquirer 3 acquires the genotype data from the specimen data storage 1.

In step S2, the acquirer 3 extracts the piece or pieces of genotype data of the target SNP or SNPs from the genotype data. The target SNP is an SNP that includes an unknown specimen. For example, in the case of the genotype data of FIG. 2, the acquirer 3 extracts the genotype data of the SNPs "rs000002" and "rs000003."

In step S3, the acquirer 3 acquires the clustering strengths "CS" of the respective target SNPs. As has been discussed in the foregoing, the acquirer 3 can acquire the clustering strength "CS" on the basis of the genotype data, the clustering data, the reference genotype frequency data, and the like.

In step S4, the determiner 4 acquires the clustering strengths "CS" of the respective target SNPs from the acquirer 3 and compares them with the threshold θ1. One and the same threshold θ1 may be used for all the target SNPs or the threshold θ1 may differ from one target SNP to another.

If CS>θ1, then the determiner 4 determines that the degree of confidence of the clustering is high (YES in step S4) and the process proceeds to step S5.

In step S5, the estimator 5 estimates the genotype of the unknown specimen by the k-nearest neighbor algorithm on the basis of the genotype data. The estimation method to estimate the genotype by the k-nearest neighbor algorithm will be described later.

If CS≤θ1 (NO in step S4), then the process proceeds to step S6.

In step S6, the determiner 4 compares the clustering strengths "CS" of the respective target SNPs acquired by the acquirer 3 with the threshold θ2. One and the same threshold θ2 may be used for all the target SNPs or the threshold θ2 may differ from one target SNP to another.

If CS<θ2, then the determiner 4 determines that the degree of confidence of the clustering is low (YES in step S6), and the process proceeds to step S7.

In step S7, the estimator 5 estimates the genotype of the unknown specimen by the imputation algorithm on the basis of the genotype data and the reference data. The estimation method to estimate the genotype by the imputation algorithm will be described later.

If CS≥θ2 (NO in step S6), then the determiner 4 determines that the degree of confidence of the clustering is at the intermediate level and the process proceeds to step S8.

In step S8, the estimator 5 estimates the genotype of the unknown specimen using both the k-nearest neighbor algorithm and the imputation algorithm. The estimation method to estimate the genotype using both the k-nearest neighbor algorithm and the imputation algorithm will be described later.

After the genotype of the unknown specimen is estimated in steps S5, S7, and S8, the display unit 6 displays the estimation result by the estimator 5 in step S9.

In the following description, the estimation methods to estimate the genotype using the k-nearest neighbor algorithm, the imputation algorithm, or both of these algorithms are described in detail.

First, the estimation method to estimate the genotype by the k-nearest neighbor algorithm in step S5 is described with reference to FIGS. 12 to 23. The "k-nearest neighbor algorithm" as used herein refers to a method of estimating the genotype of the unknown specimen on the basis of the genotypes of "k" nearest-neighbor samples. In the following description, methods that use the known specimen or the cluster line as the sample are described.

Figure 12:
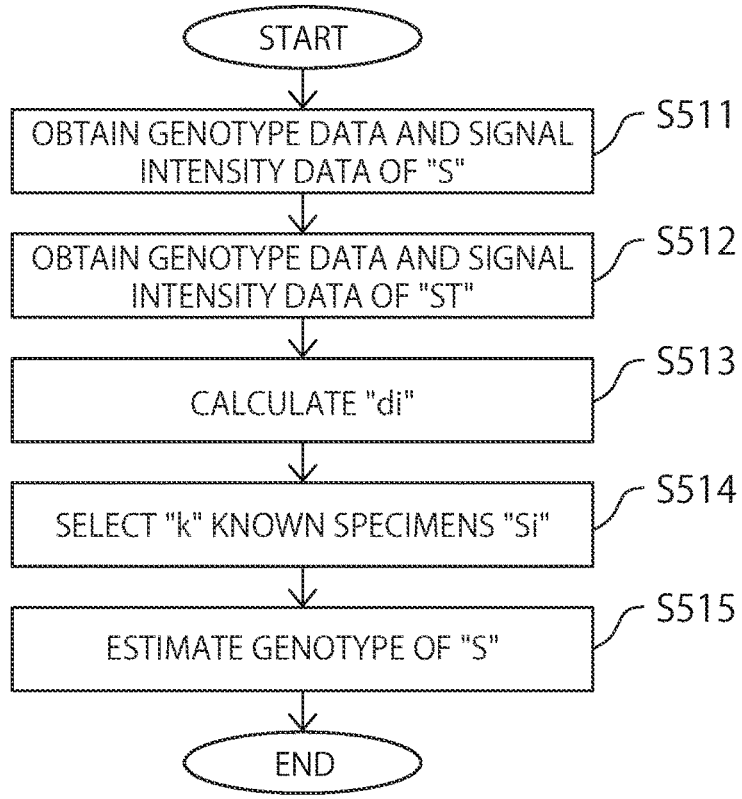
FIG. 12 is a flowchart illustrating an exemplary estimation method to estimate a genotype based on a k-nearest neighbor algorithm.

FIG. 12 is a flowchart that illustrates an example of the estimation method to estimate the genotype by the k-nearest neighbor algorithm. According to the estimation method of FIG. 12, the known specimen is used as the sample.

In step S511, the estimator 5 obtains, from the specimen data storage 1, the genotype data and the signal intensity data of an unknown specimen "S" of the target SNP. In the following description, it is assumed that one single unknown specimen "S" is given, but in a case where multiple unknown specimens "S" exist, the subsequent processes will be performed for the respective unknown specimens "S."

In step S512, the estimator 5 acquires, from the specimen data storage 1, the genotype data and the signal intensity data of the known specimen group "ST" of the target SNP. The known specimen group "ST" refers to a set of known specimens "Si" included in the target SNP.

In step S513, the estimator 5 calculates the distance "di" for the respective known specimens "Si" included in the known specimen group "ST." The distance "di" refers to the distance between the unknown specimen "S" and the known specimen "Si." The distance "di" is calculated in accordance with the following expression, for example, when the signal intensity data of the unknown specimen "S" is (x1, x2, ... xn) and the signal intensity data of the known specimen Si is (xi1, xi2, ... xin).

[Expression 4]

$$di = \frac{1}{n}\sqrt{(xi1 - x1)^2 + (xi2 - x2)^2 + \ldots + (xin - xn)^2} \quad (6)$$

In step S514, the estimator 5 selects, from the known specimens "ST," "k" nearest-neighbor known specimens "Si," i.e., "k" known specimens "Si" starting from the one having the shortest distance "di." The parameter "k" may be any appropriate natural number specified in advance. The method of specifying the parameter "k" will be described later.

Figure 13:
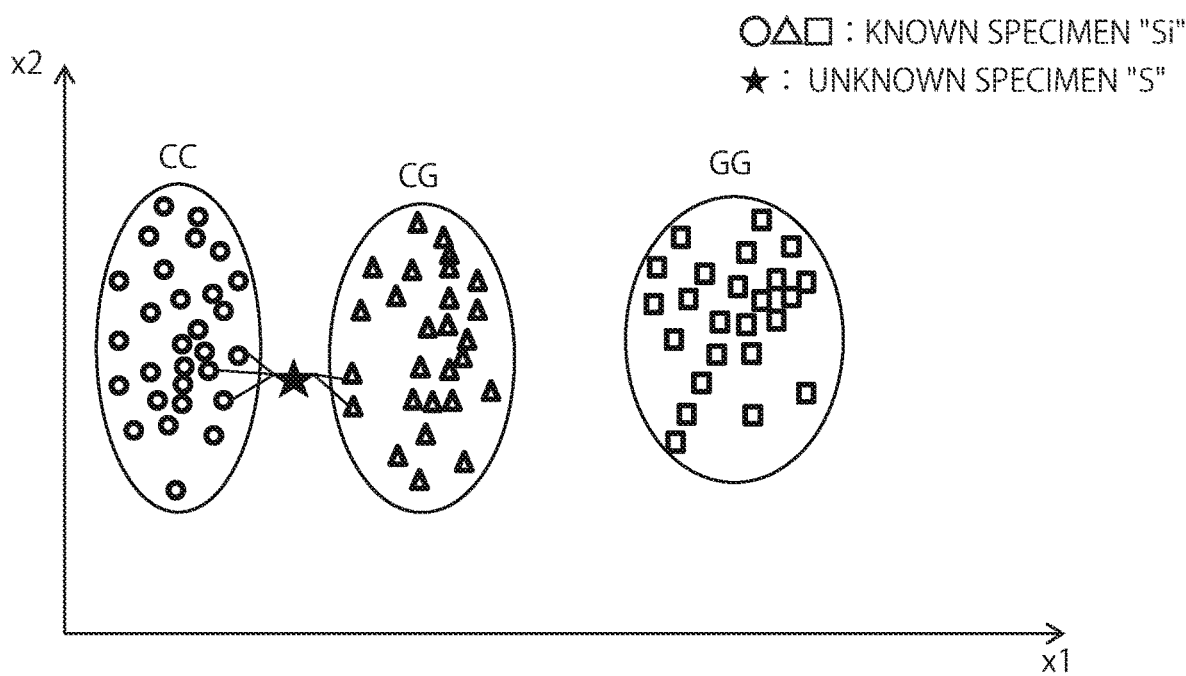
FIG. 13 is a diagram illustrating a method of selecting "k" known specimens.

FIG. 13 is a diagram that describes the method of selecting the known specimens "Si." FIG. 13 illustrates an example of a clustering map of the target SNP. In FIG. 13, there are two types of the signal intensities "x1" and "x2" (n=2) and the value of parameter "k" is 5 (k=5), a star indicates an unknown specimen "S," a circle indicates a known specimen whose genotype is "CC," a triangle indicates a known specimen whose genotype is "CG," and a rectangle indicates a known specimen whose genotype is "GG." In the case of FIG. 13, three known specimens whose genotype is "CC" and two known specimens whose genotypes are "CG" are selected starting from the one having the shortest distance "di" in step S514.

In step S515, the estimator 5 estimates the genotype of the unknown specimen "S" on the basis of the genotypes of the selected "k" known specimens "Si."

The estimator 5 estimates the genotype of the unknown specimen "S" using, for example, a majority voting algorithm. Specifically, the estimator 5 estimates a genotype held by the largest number of the specimens (number of votes) among the genotypes of the selected "k" known specimens "Si" as being the genotype of the unknown specimen "S."

Figure 14:
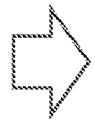
FIG. 14 is a diagram for explanation of an estimation method to estimate a genotype using a majority voting algorithm.

FIG. 14 is a diagram that illustrates the estimation method to estimate the genotype using the majority voting algorithm. Referring to FIG. 14, five known specimens "Si" (i=1 to 5) are selected and their genotypes are "AG," "GG," "AG," "AG," and "AA," respectively. In this case, the numbers of votes of the individual genotypes "AG," "GG," "AA" will be 3, 1, and 1, respectively, so that the genotype of the unknown specimen "S" is estimated as being "AG" having the largest number of votes.

Also, the estimator 5 may estimate the genotype of the unknown specimen "S" using a weighted majority voting algorithm. In this case, the estimator 5 first calculates weights of the selected individual known specimens "Si." As the weights of the known specimens "Si," a proportion of SNPs for which the genotypes have been determined in the known specimens "Si" can be used. For example, a weight of the known specimen "Si" for which 150,000 genotypes have been determined among 200,000 SNPs by the DNA microarray technology will be 0.75.

Figure 15:
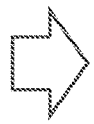
FIG. 15 is a diagram for explanation of an estimation method to estimate a genotype using a weighted majority voting algorithm.

The estimator 5 estimates the genotype having the largest number of votes as being the genotype of the unknown specimen "S" using the weights of the individual known specimens "Si" as the numbers of votes. FIG. 15 is a diagram that describes the estimation method to estimate the genotype using the weighted majority voting algorithm. In FIG. 15, five known specimens "Si" (i=1 to 5) are selected and their genotypes are "AG," "GG," "AG," "AG," and "AA," respectively, and their weights are 0.6, 0.4, 0.9, 0.7, and 0.5, respectively. In this case, the numbers of votes of the individual genotypes "AG," "GG," and "AA" are 2.2, 0.4, and 0.5, respectively, so that the genotype of the unknown specimen "S" is estimated as being "AG," having the largest number of votes.

Figure 16:
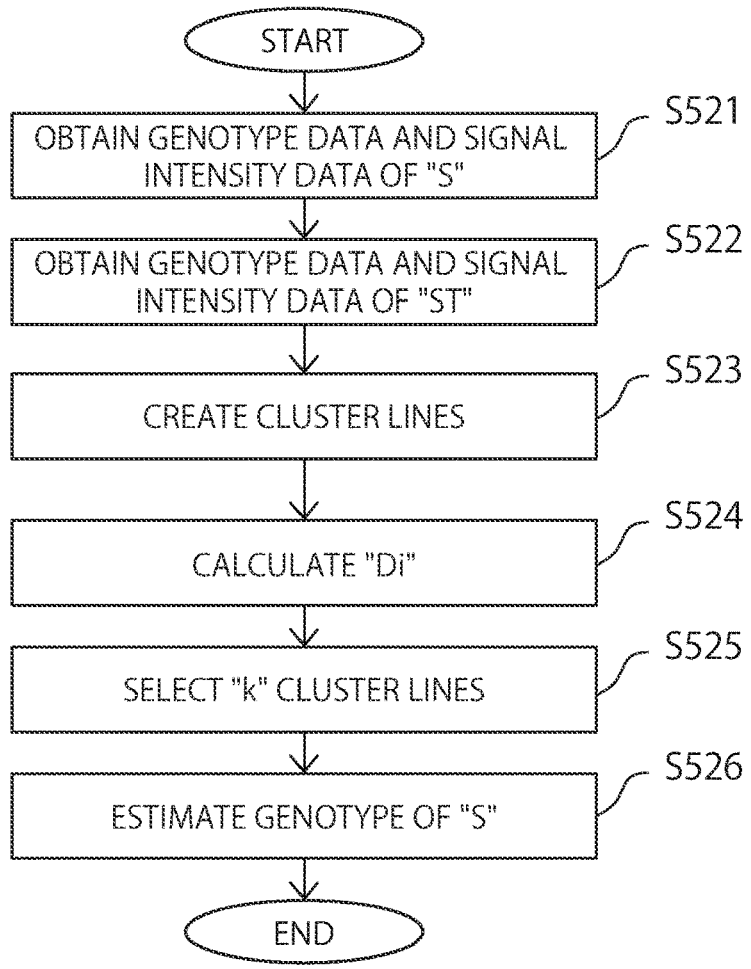
FIG. 16 is a flowchart illustrating another example of an estimation method to estimate a genotype based on a k-nearest neighbor algorithm.

FIG. 16 is a flowchart that illustrates another example of the estimation method to estimate the genotype by the k-nearest neighbor algorithm. According to the estimation method of FIG. 16, a cluster line is used as a sample.

In step S521, the estimator 5 acquires, from the specimen data storage 1, the genotype data and the signal intensity data of the unknown specimen "S" of the target SNP. Step S521 corresponds to the above-described step S511.

In step S522, the estimator 5 acquires, from the specimen data storage 1, the genotype data and the signal intensity data of the known specimen group "ST" of the target SNP. Step S522 corresponds to the above-described step S512.

In step S523, the estimator 5 creates the cluster line "Ci" on the basis of the signal intensity data of the known specimen group "ST." The cluster line "Ci" corresponds to approximation of the known specimens included in the individual clusters (the individual genotypes) in the cluster space by straight lines or curves. The cluster line "Ci" can be created by regression analysis of the coordinates of the known specimens in the cluster space. Both linear regression and non-linear regression may rely on in the regression analysis.

Figure 17:
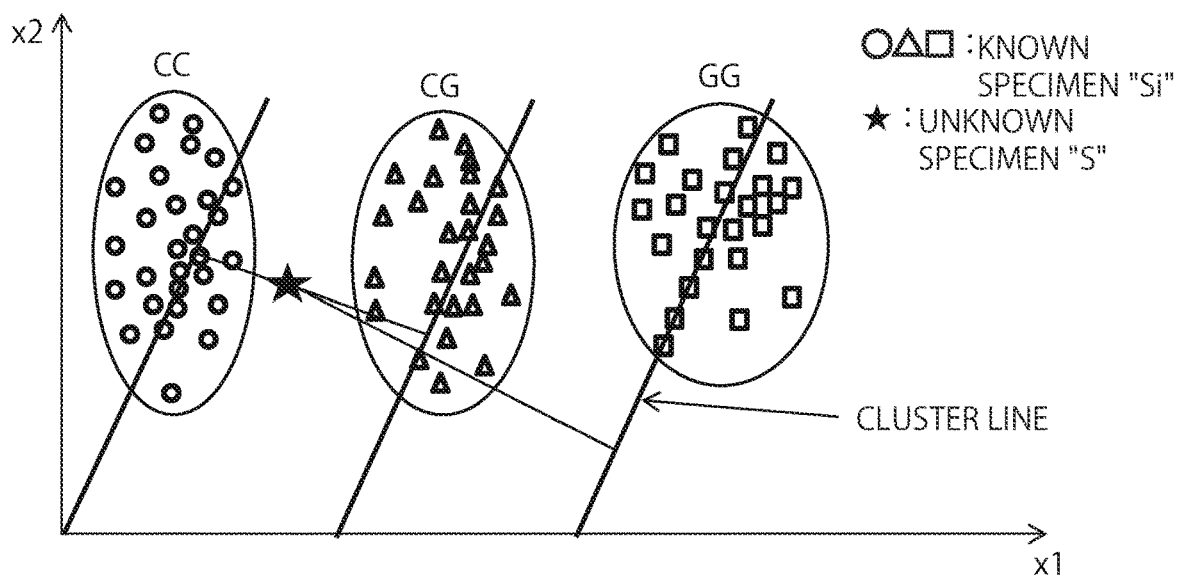
FIG. 17 is a diagram for explanation of a creation method to create a cluster line.

FIG. 17 is a diagram that describes the creation method of the cluster line "Ci." FIG. 17 illustrates an example of the clustering map of the target SNP. Referring to FIG. 17, there are two types of signal intensities "x1" and "x2" (n=2) and five parameters "k" (k=5). A star indicates an unknown specimen "S," a circle indicates a known specimen whose genotype is "CC," a triangle indicates a known specimen whose genotype is "CG," and a rectangle indicates a known specimen whose genotype is "GG." Also, the cluster line "Ci" is a straight line, and one cluster line is created for one cluster. In the case of FIG. 17, the cluster line "Ci" is expressed by the following expression.

[Expression 5]

$$x2 = m_i x1 + c_i \quad (7)$$

In the above expression (7), "$m_i$" and "$c_i$" are constants and obtained by the regression analysis. The estimator 5 can create such a cluster line "Ci" as described above by performing linear regression analysis for each cluster.

Figure 18:
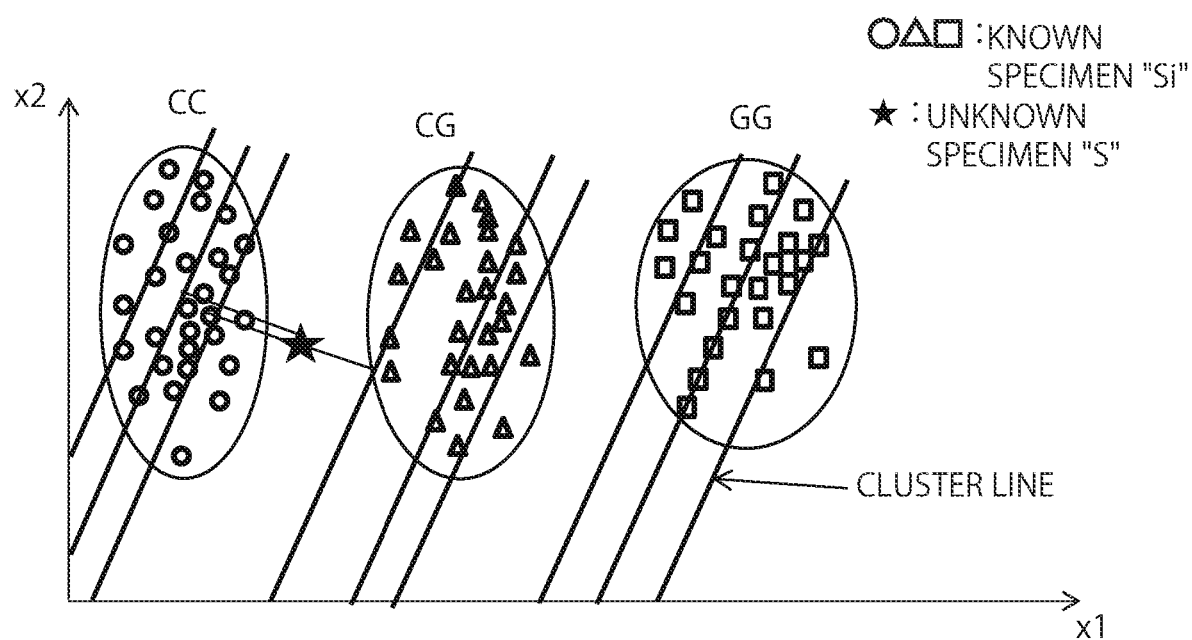
FIG. 18 is a diagram for explanation of a creation method to create multiple cluster lines per genotype.

Also, as illustrated in FIG. 18, several cluster lines "Ci" may be created for each cluster. In this case, the estimator 5 divides each cluster into a plurality of sub-clusters and the cluster lines "Ci" may be created for the respective sub-clusters in accordance with the above expression (7).

It should be noted that cluster line "Ci" is not limited to a straight line but may be a curve. Also, the number of cluster lines "Ci" may be selected as appropriate.

In step S524, the estimator 5 calculates the distances "Di" for the respective cluster lines "Ci." The distance "Di" is a distance between the unknown specimen "S" and the cluster line "Ci." The distance "Di" is calculated in accordance with the following expression, for example, when the signal intensity data of the unknown specimen "S" is "(xs1,xs2)" and the cluster line "Ci" is "$x2 = m_i x1 + c_i$."

[Expression 6]

$$Di = \frac{|xs2 - m_i xs1 - c_i|}{\sqrt{1 + m_i^2}} \quad (8)$$

In step S525, the estimator 5 selects "k" nearest-neighbor cluster lines "Ci," i.e., "k" cluster lines "Ci" starting from the one having the shortest distance "Di" from among the created multiple cluster lines "Ci."

For example, if k=1 in FIG. 17, then the cluster line "Ci" of the genotype "CC" having the shortest distance "Di" is selected. Also, if k=3 in FIG. 18, then two cluster lines with the genotype of "CC" and one cluster line with the genotype of "CG" are selected starting from the one having the shortest distance "Di."

In step S526, the estimator 5 estimates the genotype of the unknown specimen "S" on the basis of the genotypes of the selected "k" cluster lines "Ci."

The estimator 5 estimates the genotype of the unknown specimen "S" using, for example, the majority voting algorithm. Specifically, the estimator 5 estimates a genotype held by the largest number of the cluster lines (number of votes) among the genotypes of the selected "k" cluster lines "Ci" as being the genotype of the unknown specimen "S."

Figure 19:
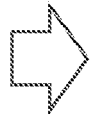
FIG. 19 is a diagram for explanation of an estimation method to estimate a genotype using a majority voting algorithm.

FIG. 19 is a diagram that describes the estimation method to estimate the genotype using the majority voting algorithm. Referring to FIG. 19, five cluster lines "Ci" (i=1 to 5) are selected and their genotypes are "AG," "GG," "AG," "AG," and "AA," respectively. In this case, since the numbers of votes of the respective genotypes "AG," "GG," and "AA" are 3, 1, and 1, respectively, the genotype of the unknown specimen "S" is estimated as being "AG" having the largest number of votes.

Also, the estimator 5 may estimate the genotype of the unknown specimen "S" using the weighted majority voting algorithm. In this case, the estimator 5 first calculates the weights of the selected cluster lines "Ci." As the weights of the cluster lines "Ci," it is possible to use an average value on a per-cluster basis of proportions of SNPs for which the genotypes have been determined in the known specimens "Si." The estimator 5 uses the weights of the respective cluster lines "Ci" as the numbers of votes and estimates the genotype having the largest number of votes as being the genotype of the unknown specimen "S."

Figure 20:
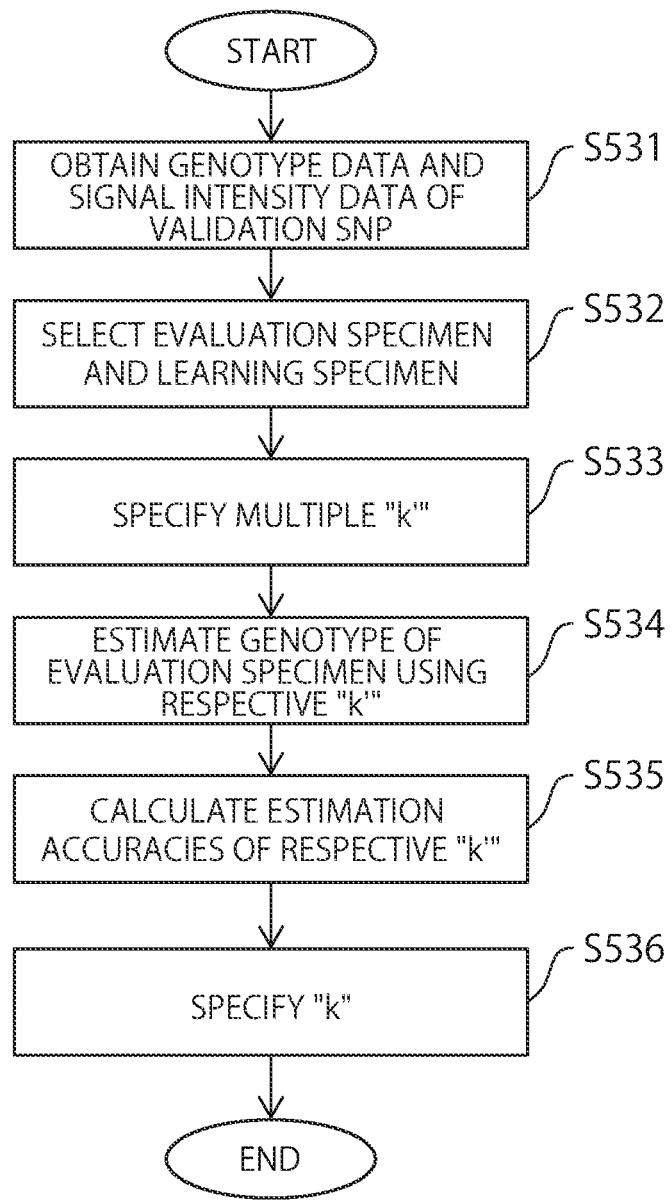
FIG. 20 is a flowchart illustrating a determination method to determine the value of parameter k.

Here, the method of specifying the parameter "k" used in the k-nearest neighbor algorithm is described with reference to FIGS. 20 to 23. FIG. 20 is a flowchart that illustrates the method of specifying the parameter "k." In this embodiment, the estimator 5 specifies the parameter "k" by cross validation.

In step S531, the estimator 5 acquires, from the specimen data storage 1, genotype data and the signal intensity data of one or more validation SNPs for use in validation. The "validation SNP" as used herein refers to an SNP having a large clustering strength "CS" whose specimens are all known specimens. The validation SNP is, for example, an SNP whose clustering strength "CS" is larger than the threshold θ1.

Figure 21:
FIG. 21 is a diagram for explanation of validation SNP.

FIG. 21 is a diagram that describes the validation SNP. In the genotype data of FIG. 21, the specimens of the SNPs "rs00001" and "rs000003" are all known specimens. When the clustering strengths "CS" of these SNPs are large, the estimator 5 extracts the SNPs "rs00001" and "rs000003" as the validation SNPs and acquires their genotype data and signal intensity data.

In step S532, the estimator 5 selects the evaluation specimen for use in evaluation and the learning specimen for use in learning. The "evaluation specimen" as used herein refers to a specimen handled as the unknown specimen. The "learning specimen" is a specimen handled as the known specimen. The genotype of the specimen selected as the evaluation specimen is used as correct answer data for cross validation.

FIG. 22 is a diagram that illustrates an example of the evaluation specimen the learning specimen. Referring to FIG. 22, the specimens "01" to "10" are selected as the evaluation specimens and the specimens "11" to "N" are selected as the learning specimens. It should be noted that the evaluation specimen and the learning specimen can be selected as appropriate.

In step S533, the estimator 5 specifies a plurality of candidates "k'" for the parameter "k." The estimator 5 can specify any appropriate natural number as the candidate "k'" for the parameter "k."

In step S534, the estimator 5 estimates the genotypes of the respective evaluation specimens on the basis of the genotype data and the signal intensity data of the learning specimens. At this point, the estimator 5 estimates the genotype of the evaluation specimens by the k-nearest neighbor algorithm using the respective candidates "k'" as the parameters "k."

In step S535, the estimator 5 calculates the estimation accuracies of the respective candidates "k'" by the cross validation. Specifically, the estimator 5 compares the estimation results of the genotypes of the evaluation specimens with the known genotypes of the evaluation specimens, and calculates a proportion of the evaluation specimen whose genotypes have been correctly estimated.

Figure 23:
FIG. 23 is a diagram illustrating an exemplary calculation result of estimation accuracy.

FIG. 23 is a diagram that illustrates an example of the calculation results of the estimation accuracies. As illustrated in FIG. 23, the estimation accuracies are calculated for the respective candidates "k'" of the respective validation SNPs. For example, referring to FIG. 23, the estimation accuracy of the SNP "rs000001" with the candidate k'=1 is 0.8. Also, as illustrated in FIG. 23, if more than one validation SNP exists, the estimator 5 may calculate the average value (average estimation accuracy) of the estimation accuracies of the respective candidates "k'."

In step S536, the estimator 5 specifies the candidate "k'" having the highest estimation accuracy as the parameter "k." Also, when the cross validation has been performed for multiple validation SNPs, the estimator 5 may specify the candidate "k'" having the highest average estimation accuracy as the parameter "k." For example, in the case of FIG. 23, the parameter "k" is specified as 5 which guarantees the highest average estimation accuracy.

Figure 24:
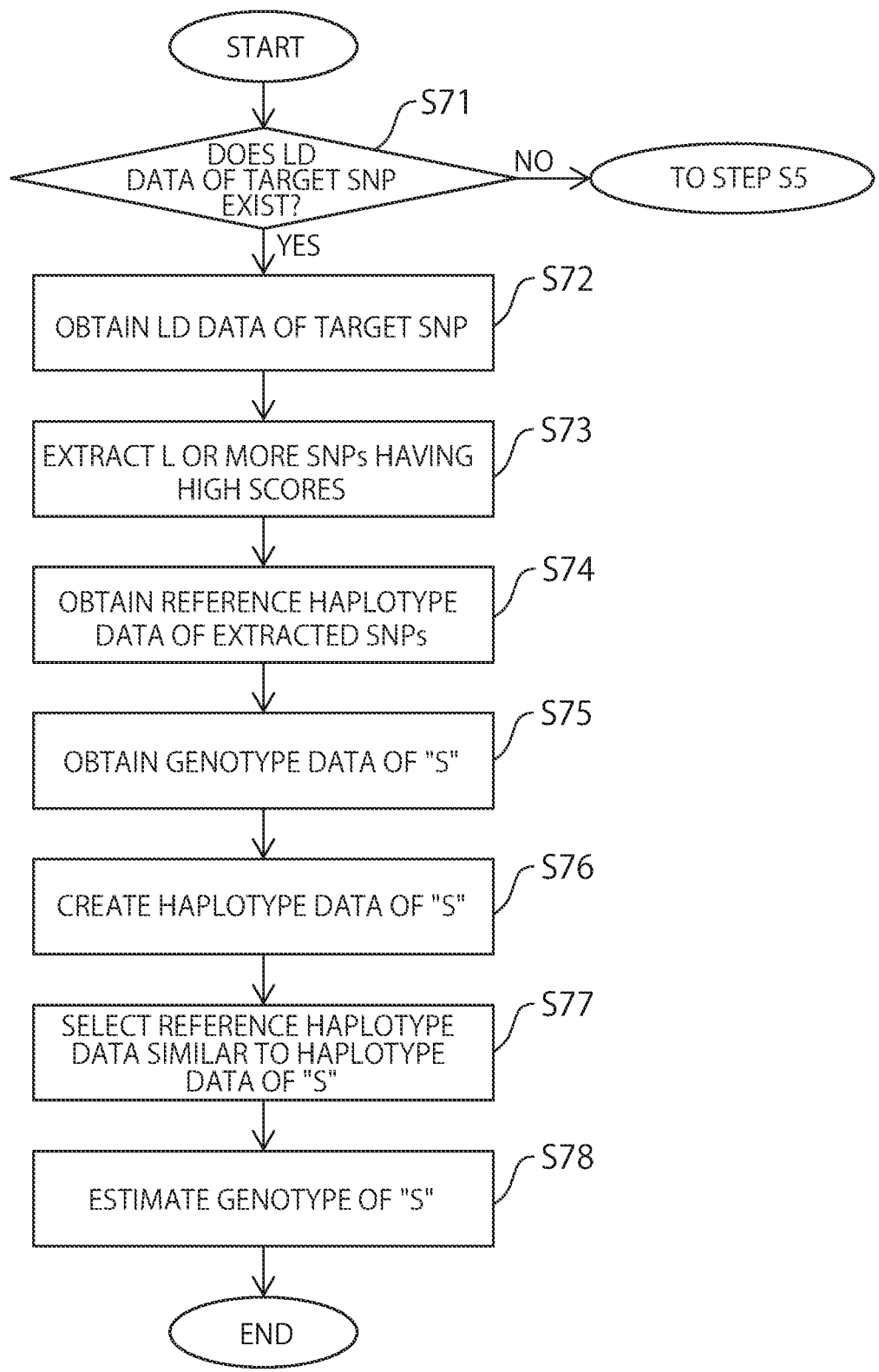
FIG. 24 is a flowchart illustrating an estimation method to estimate a genotype imputation algorithm.

Next, the estimation method to estimate the genotype using the imputation algorithm in step S7 is described with reference to FIGS. 24 to 29. FIG. 24 is a flowchart that illustrates the estimation method to estimate the genotype by the imputation algorithm.

In step S71, the estimator 5 refers to the reference data storage 2 and checks whether or not the LD data of the target SNP exists in the reference data storage 2. According to the imputation algorithm, the LD data of the target SNP is used. Accordingly, if the LD data of the target SNP does not exist (NO in step S71), the process proceeds to step S5 to estimate the genotype of the unknown specimen "S" by the k-nearest neighbor algorithm. The estimation method by the k-nearest neighbor algorithm has already been described in the foregoing description.

Meanwhile, when the LD data of the target SNP exists (YES in step S71), the process proceeds to step S72.

In step S72, the estimator 5 acquires the LD data of the target SNP from the reference data storage 2.

Figure 25:
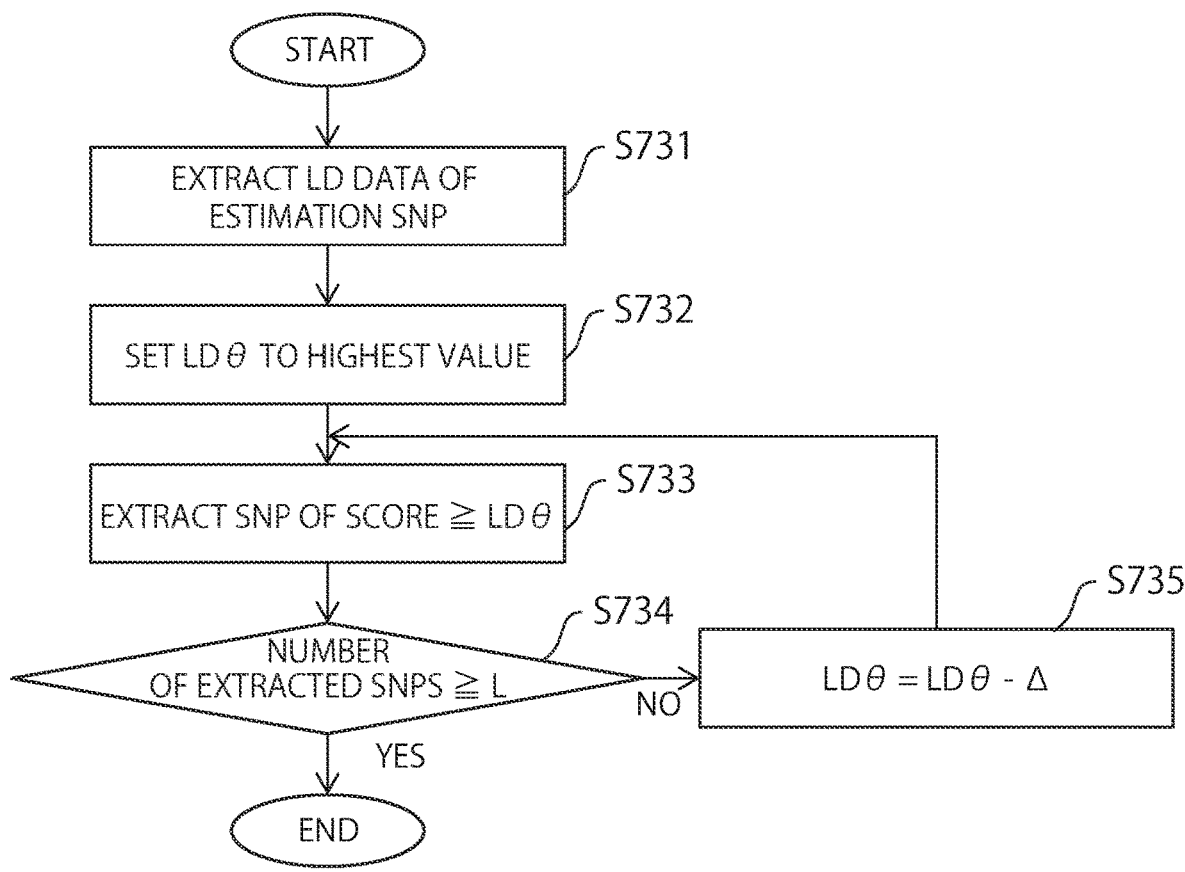
FIG. 25 is a flowchart illustrating an extraction method to extract an SNP.

In step S73, the estimator 5 refers to the LD data of the target SNP and extracts "L" or more SNPs having high scores. FIG. 25 is a flowchart that illustrates the SNP extraction method in step S73.

In step S731, the estimator 5 extracts the LD data of an estimation SNP from the LD data of the target SNP. The estimation SNP refers to an SNP having a larger clustering strength "CS" whose specimens are all known specimens. The estimation SNP is, for example, an SNP whose clustering strength "CS" is larger than the threshold θ1.

The LD data of the target SNP includes scores of multiple SNPs with respect to the target SNP. The estimator 5 refers to the genotype data and the clustering data of the respective SNPs whose scores are included in the LD data of the target SNP and extracts the LD data of the estimation SNP.

In step S732, the estimator 5 specifies the threshold "LDθ" of the scores as the highest value of the scores included in the LD data of the estimation SNP. The score can be selected as appropriate from the linkage disequilibrium score, the coefficient of correlation, and the logarithm of odds or the like included in the LD data.

In step S733, the estimator 5 refers to the LD data of the estimation SNP and extracts, from the estimation SNPs, SNPs whose scores are equal to or higher than the threshold "LDθ."

In step S734, the estimator 5 determines whether or not the number of the extracted SNPs is equal to or larger than a predetermined value "L." The value "L" can be specified as appropriate. When the number of the extracted SNPs is less than the "L" (NO in step S734), the process proceeds to step S735.

In step S735, the estimator 5 lowers the threshold "LDθ" (LDθ=LDθ−Δ). The decrement "Δ" of the threshold "LDθ" is, for example, 0.01. After the threshold "LDθ" is lowered, the process proceeds to step S733. The estimator 5 then repeats the processes of steps S733 to S735 until the number of the extracted SNPs becomes equal to or larger than the "L."

When the number of the extracted SNPs is equal to or larger than "L" (YES in step S734), the SNP extraction process is completed and the process proceeds to step S74. In accordance with the above process, the estimator 5 can extract "L" or more estimation SNPs whose scores are equal to or higher than the threshold "LDθ."

In step S74, the estimator 5 acquires the reference haplotype data of the SNP extracted in step S73 from the reference data storage 2.

In step S75, the estimator 5 acquires genotype data of the unknown specimen "S" from the specimen data storage 1.

In step S76, the estimator 5 creates the haplotype data of the unknown specimen "S" from the genotype data of the unknown specimen "S." The haplotype data of the unknown specimen "S" can be created by extracting the genotype of the SNP from the genotype data using a phasing algorithm and then determining the sequence of alleles existing in each chromosome. As the phasing algorithm, for example, BEAGLE, fastPHASE, IMPUTEv2, MACH, and ShapeIT can be used.

FIG. 26 is a diagram that illustrates an example of the haplotype data of the unknown specimen "S." As illustrated in FIG. 26, two pieces of the haplotype data "HTD1" and "HTD2" are created by the phasing algorithm from the genotype data of the unknown specimen "S." In the haplotype data of the unknown specimen "S," since the pair of alleles of the SNP whose genotype is not known is indefinite, it is indicated by "—."

In step S77, the estimator 5 selects, from the reference haplotype data acquired in step S74, the pieces of the reference haplotype data that are the most similar to the two pieces of haplotype data "HTD1" and "HTD2" of the unknown specimen "S," respectively. Similarity of the reference haplotype data to the haplotype data "HTD1" and "HTD2" refers to similarity of the sequence of the alleles of an SNP other than the one SNP whose genotype is not known.

FIG. 27 is a diagram that illustrates the selection method of the reference haplotype data. For example, in step S74, when the reference haplotype data of FIG. 27 has been extracted, the estimator 5 selects the reference haplotype data "refHTD5" as the reference haplotype data that is the most similar to the haplotype data "HTD1" and selects the reference haplotype data "refHTD3" as the reference haplotype data that is the most similar to the haplotype data "HTD2." The details of the method of selecting the reference haplotype data will be described later.

In step S78, the estimator 5 estimates the genotype of the unknown specimen "5" on the basis of the alleles of the target SNP in the two pieces of the reference haplotype data. For example, when the reference haplotype data is selected as illustrated in FIG. 27, the estimator 5 estimates one of the alleles of the SNP "rs987009" as being "G" and the other of the alleles as being "A." In addition, the estimator 5 estimates the genotype of the SNP "rs987009" of the unknown specimen "5" as being "AG" on the basis of these alleles.

Figure 28:
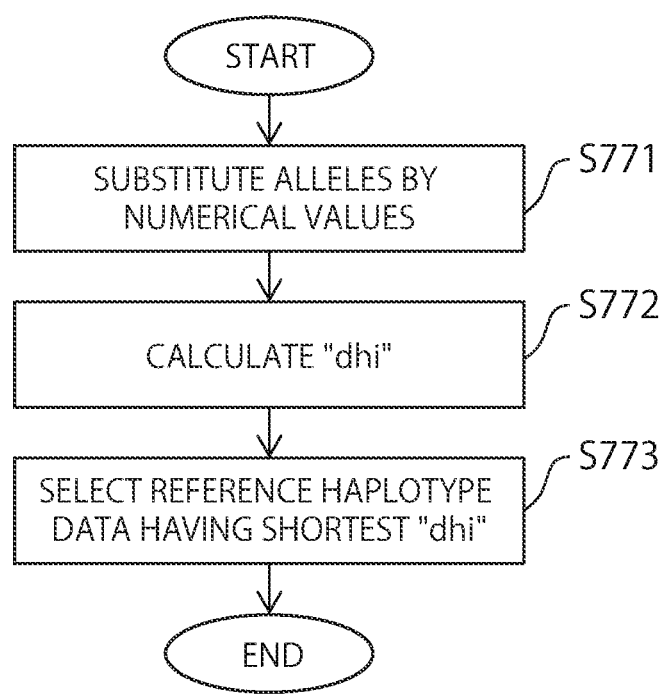
FIG. 28 is a flowchart illustrating a selection method to select reference haplotype data.

FIG. 28 is a flowchart that illustrates the selection method of the reference haplotype data in step S77.

In step S771, the estimator 5 substitutes the extracted reference haplotype data and the alleles of the haplotype data of the unknown specimen "S" into numerical values. FIG. 29 is a diagram that illustrates an example of the reference haplotype data whose alleles are substituted by numerical values and the haplotype data of the unknown specimen "S." In FIG. 29, the alleles "A," "C," "G," and "T" are substituted by the numerical values 1, 2, 3, and 4, respectively.

In step S772, the estimator 5 calculates the distance "dhi." The distance "dhi" is a distance between the respective pieces of the haplotype data of the unknown specimens "S" and the respective pieces of the reference haplotype data. The distance "dhi" is, for example, calculated in accordance with the following expression.

[Expression 7]

$$dhi = \frac{1}{p}\sqrt{(si1 - s1)^2 + (si2 - s2)^2 + \ldots + (sip - sp)^2} \quad (9)$$

In the above expression (9), "p" is the number of the SNPs except for the SNP whose genotype is not known among the SNPs included in the haplotype data of the unknown specimen "S," "sij" (j=1 to p) is the numerical value of the j-th SNP of the reference haplotype data "i," and "sj" (j=1 to p) is the numerical value of the j-th SNP of the haplotype data of the unknown specimen "S."

For example, in the case of FIG. 29, the distance "dhi" between the haplotype data "HTD1" and the reference haplotype data "refHTD1" is calculated as 0.35 (=sqrt(((1−1)$^2$+(4−4)$^2$+(3−3)$^2$+(4−1)$^2$+(2−2)$^2$+(4−4)$^2$+(2−3)$^2$+(1−1)$^2$+(2−2)$^2$))/9).

In step S773, with regard to the respective pieces of the haplotype data of the unknown specimen "S," the estimator 5 selects a piece of reference haplotype data having the shortest distance "dhi" as the most similar piece of the reference haplotype data.

Figure 30:
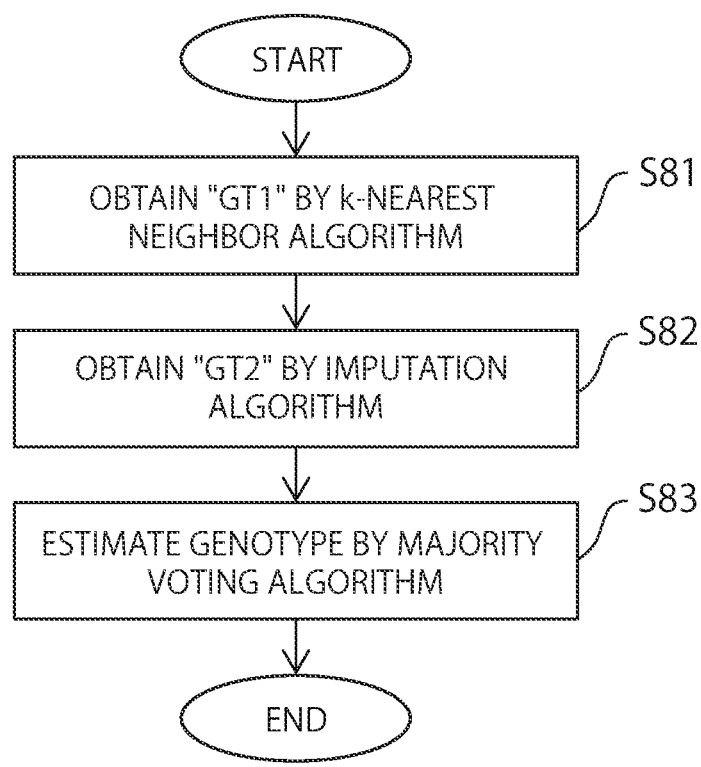
FIG. 30 is a flowchart illustrating an estimation method to estimate a genotype using both the k-nearest neighbor algorithm and the imputation algorithm.

Next, the estimation method to estimate the genotype using both k-nearest neighbor algorithm and the imputation algorithm in step S8 is described with reference to FIG. 30. FIG. 30 is a flowchart that illustrates the estimation method to estimate the genotype using both k-nearest neighbor algorithm and the imputation algorithm.

In step S81, the estimator 5 estimates the genotype of the unknown specimen "S" by the k-nearest neighbor algorithm and acquires genotype group "GT1" that includes one or more genotype candidates. If the number of genotype candidates included in the genotype group "GT1" is given as "α," then the genotype group "GT1" can be acquired, for example, by selecting "α" genotypes as the genotype candidates starting from the one having the largest number of votes, or by estimating genotypes by "α" parameters "k."

In step S82, the estimator 5 estimates the genotype of the unknown specimen "S" by the imputation algorithm, and acquires the genotype group "GT2" that includes one or more genotype candidates. If the number of the genotype candidates included in the genotype group "GT2" is given as "β," then the genotype group "GT2" can be acquired, for example, by selecting "β" pieces of the similar reference haplotype data for each haplotype data of the unknown specimen "S" and estimating the genotype.

In step S83, the estimator 5 estimates the genotype of the unknown specimen "S" from the genotype candidates included in the genotype groups "GT1" and "GT2" using the majority voting algorithm. As the number of votes of the majority voting algorithm, the number of genotypes included in the genotype groups "GT1" and "GT2" can be used.

As has been described in the foregoing description, the estimation device and the estimation method in accordance with this embodiment estimate the genotype that could not be determined by the DNA microarray technology in accordance with the degree of confidence of the clustering by the DNA microarray technology. Specifically, if the degree of confidence is low, the genotype is estimated by the imputation algorithm that uses the reference data. When the degree of confidence is high, the genotype is estimated by the k-nearest neighbor algorithm that uses the genotype data that has been determined by the DNA microarray technology. By virtue of this, the estimation device and the estimation method in accordance with this embodiment can accurately estimate the genotype.

Figure 31:
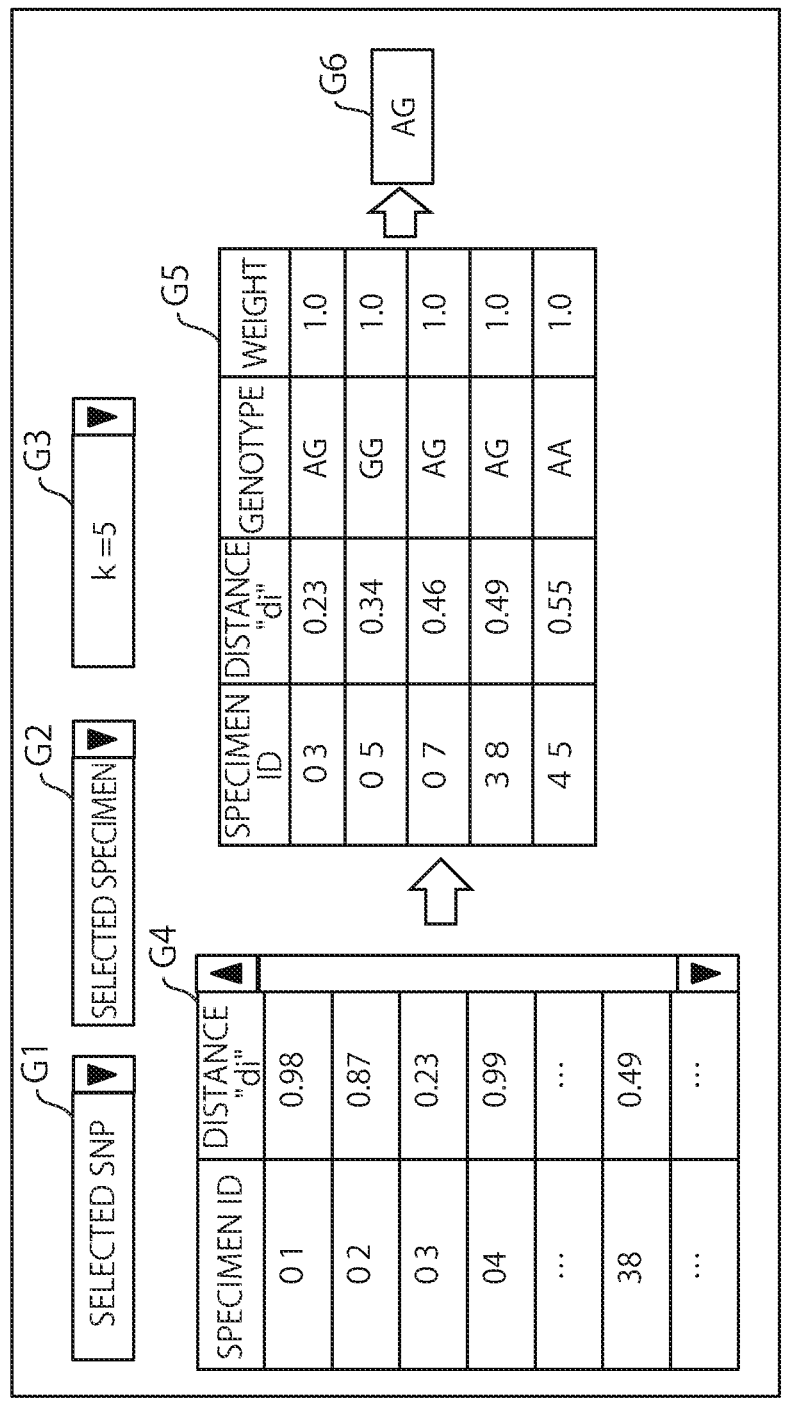
FIG. 31 is a diagram illustrating an example of an operation screen of a graphical user interface (GUI) of the genotype estimation device of FIG. 1.

It is preferable that the above-described estimation device in accordance with this embodiment can be operated by a graphical user interface (GUI). FIG. 31 is a diagram that illustrates an example of the operation screen of the GUI displayed by the display unit 6. FIG. 31 is a GUI in the case where the genotype is estimated by the k-nearest neighbor algorithm using the known specimen as the sample. As illustrated in FIG. 31, this GUI includes an SNP selector G1, a specimen selector G2, a k-value selector G3, a specimen list display section G4, a selection result display section G5, and a genotype display section G6.

The SNP selector G1 is a drop-down list for the user to select the target SNP. The drop-down list of the SNP selector G1 includes the IDs of all the SNPs including the unknown specimens. The ID of the target SNP selected by the user is displayed on the SNP selector G1.

The specimen selector G2 is a drop-down list for the user to select the unknown specimen "S" whose genotype is to be estimated. The drop-down list of the specimen selector G2 includes the IDs of all the unknown specimens "S" included in the genotype data of the target SNP. The content of the drop-down list of the specimen selector G2 changes depending on the target SNP selected by the user. The IDs of the unknown specimens "S" selected by the user are displayed on the specimen selector G2.

The k-value selector G3 is a drop-down list for the user to specify the parameter "k." The drop-down list of the k-value selector G3 includes multiple candidates for the value of the parameter "k." The value of the parameter "k" specified by the user is displayed on the k-value selector G3. In FIG. 31, the parameter "k" is specified as "5." It is preferable that the value of the parameter "k" of the highest estimation accuracy is specified as the default value in the k-value selector G3.

The specimen list display section G4 displays the list of the IDs of the known specimen (the known specimen "Si" included in the known specimens "ST") included in the genotype data of the target SNP selected by the user, and the distance "di" between the individual known specimens "Si" and the unknown specimen "S" selected by the user. The distance "di" displayed in FIG. 31 is a distance calculated by the above-described expression (6).

The selection result display section G5 displays the IDs, distances "di," genotypes, and the weights of the "k" known specimens "Si" having the small distances "di" selected from the known specimens "Si" displayed on the specimen list display section G4. Referring to FIG. 31, since there are five parameters "k," five known specimens "Si" are displayed. The weight is a weight for use in the majority voting algorithm and 1.0 is specified therefor as the default value. If the weight is 1.0, the majority voting algorithm will be an unweighted majority voting algorithm. When a weighted algorithm is used, only the weight of the individual known specimens "Si" calculated by the above-described method is displayed as the weight.

The genotype display section G6 displays the estimation result of the genotype by the k-nearest neighbor algorithm. Referring to FIG. 31, the estimated genotype is "AG."

Figure 32:
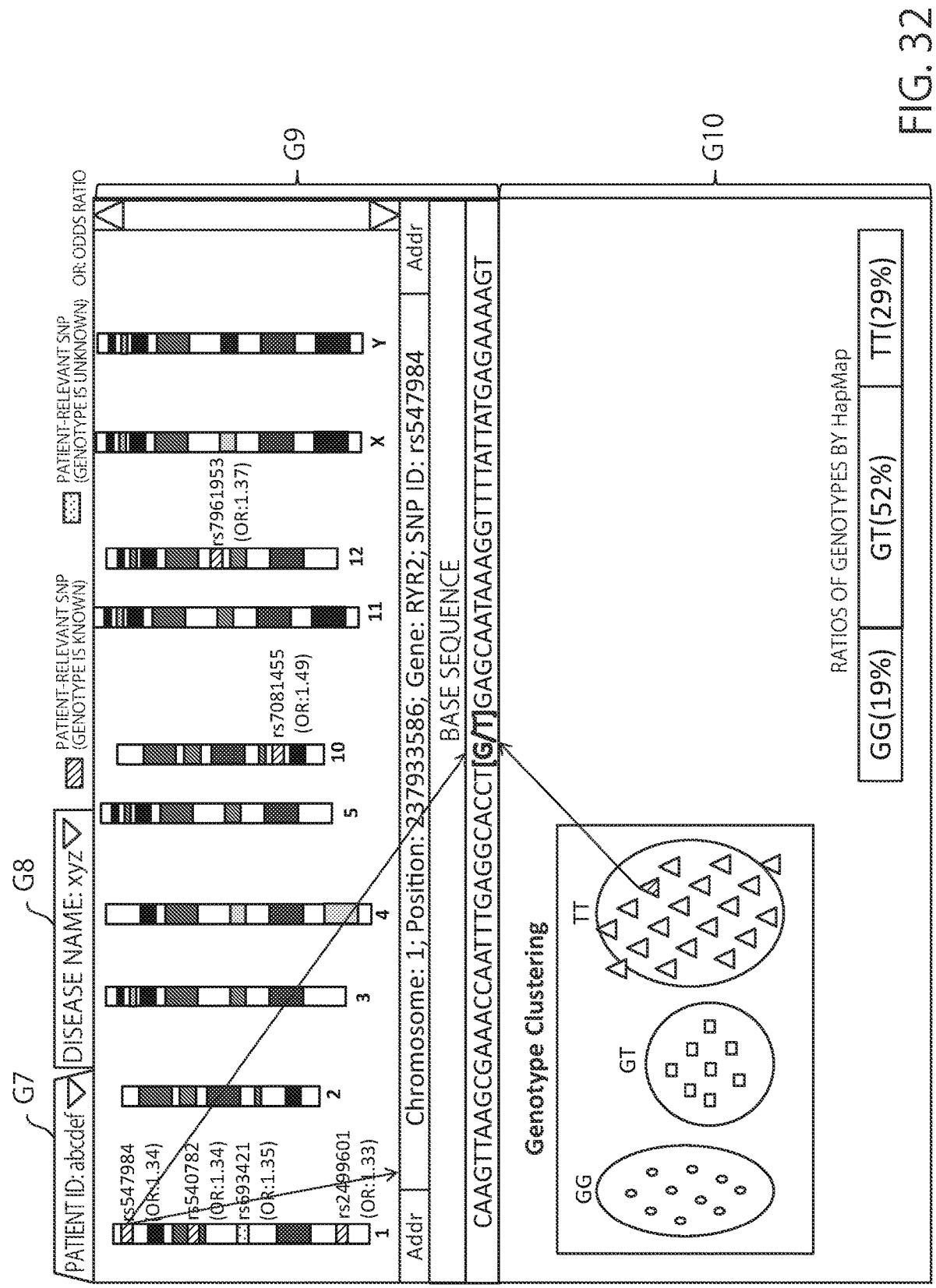
FIG. 32 is a diagram illustrating another example of the operation screen of the GUI of the genotype estimation device of FIG. 1.

FIG. 32 is a diagram that illustrates another example of the operation screen of the GUI of the estimation device. The estimation device that includes the GUI of FIG. 32 stores, in the reference data storage 2, information indicative of the relevance between SNP and disease. As illustrated in FIG. 32, this GUI includes a patient selector G7, a disease selector G8, an SNP information display section G9, and a genotype information display section G10.

The patient selector G7 is a drop-down list for the user to select a patient. The patient as used herein corresponds to the specimen whose genotype has been determined by the DNA microarray technology. IDs of multiple patients (specimens) are included in the drop-down list of the patient selector G7. The IDs of the patients selected by the user are displayed on the patient selector G7.

The disease selector G8 is a drop-down list for the user to select the disease. The drop-down list of the disease selector G8 includes the names of multiple diseases stored in the reference data storage 2. The name or names of a disease or diseases selected by the user are displayed in the disease selector G8.

The SNP information display section G9 displays the SNP information related to the patients and diseases selected by the user. The SNP information includes the types of the chromosome, ID of SNP, gene locus, disease-relevant SNP, odds ratio (OR), Addr information, base sequence information, etc. The "odds ratio" as used herein is a measure used as the method of indicating the result of the medical clinical trials, and is a statistical measure that indicates susceptibility to diseases by comparison of two groups. Also, the Addr information and the base sequence information will be described later. The SNP information is stored in the reference data storage 2.

Still referring to FIG. 32, the SNP information display section G9 displays 1 to 5, 10 to 12, and XY chromosomes. The shaded portion on each chromosome indicates the SNP whose genotype is known among the disease-relevant SNPs, and the dotted portion thereof indicates the SNP whose genotype is not known among the disease-relevant SNPs. In FIG. 32, the SNPs on the respective chromosomes are provided as a command button. When the user selects (clicks on) it, the Addr information related to this SNP and the base sequence around the SNP are displayed.

The Addr information includes the number of the chromosome (Chromosome) to which the SNP belongs, the gene locus (Position) on the chromosome, the name of the gene to which the SNP belongs (Gene), and the ID of the SNP. The Addr information of the SNP selected by the user by the command button is displayed in the "Addr" field of the SNP information display section G9.

The base sequence information is base sequence data of the gene locus except for SNP. When the user selects an SNP by the command button, the base sequence around the selected SNP is extracted from the base sequence information, and the genotype data of the SNPs included in the range of the extracted base sequence is extracted from the specimen data storage 1 and displayed in the base sequence field of the SNP information display section G9. Referring to the base sequence of FIG. 32, the alleles A and B of the SNP are indicated by the notation "[A/B]." For example, in FIG. 32, the alleles of the SNP "rs547984" are "G" and "T."

The genotype information display section G10 displays the genotype information regarding the SNP selected by the user. The genotype information is generated by various pieces of data stored in the specimen data storage 1.

When the genotype of the SNP selected by the user is known, the genotype information display section G10 displays, as illustrated in FIG. 32, a clustering map (Genotype Clustering) of the selected SNP and the ratio of the genotype by the HapMap and the like.

The clustering map may be stored in advance in the specimen data storage 1 or generated from the signal intensity data stored in the specimen data storage 1. Also, the ratio of the genotype by HapMap refers to a ratio of the genotype of the selected SNP in the ethnic group to which the patient belongs. The ratio of the genotype by the HapMap can be extracted from the reference genotype frequency data.

Figure 33:
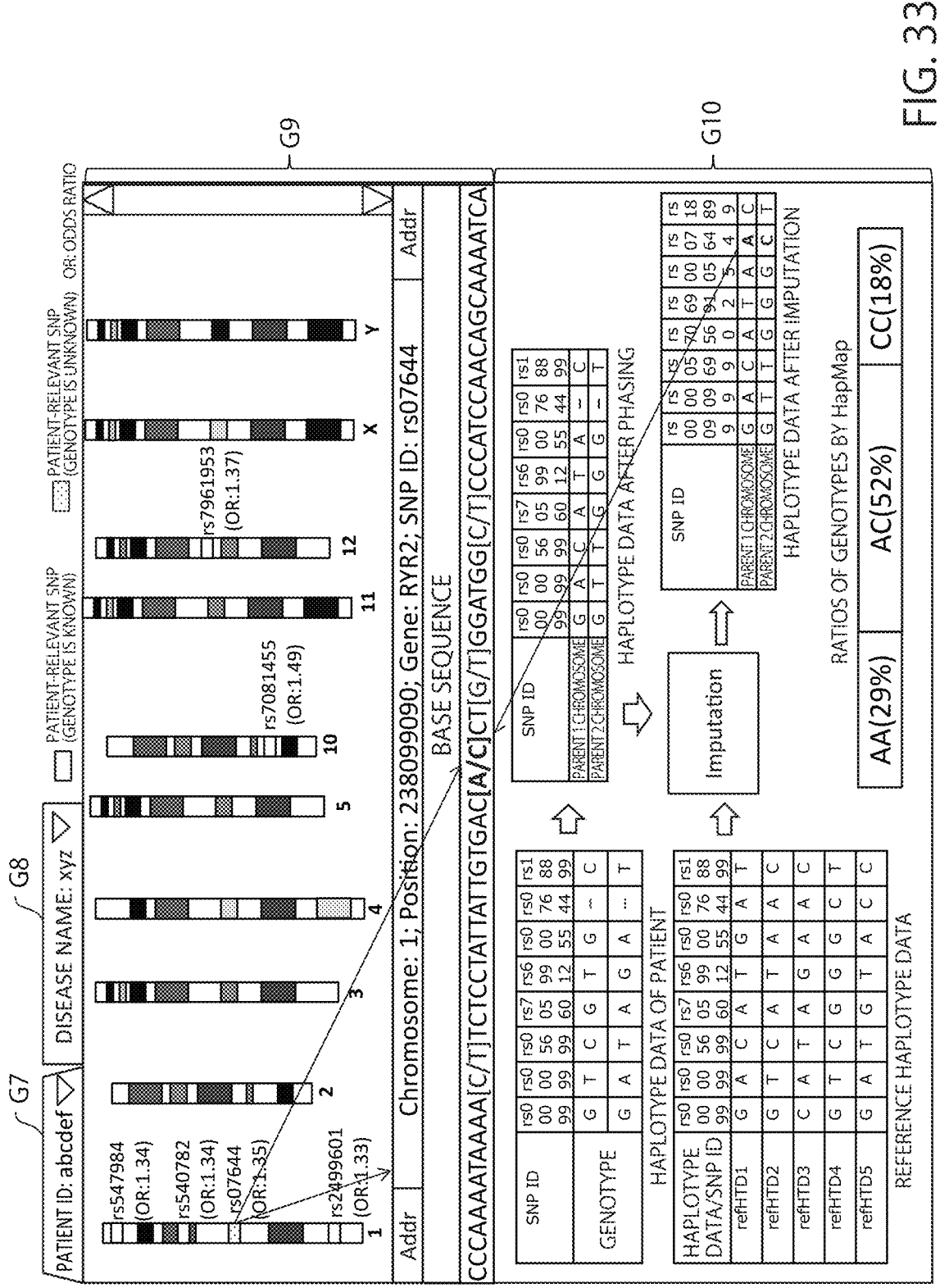
FIG. 33 is a diagram illustrating still another example of the operation screen of the GUI of the genotype estimation device of FIG. 1.

In contrast, when the genotype of the SNP selected by the user is not known, then the genotype information display section G10 displays, as illustrated in FIG. 33, estimation results of the genotype by the estimator 5 and data indicative of the process of the estimation of the genotype.

Referring to FIG. 33, the "Imputation" displayed in the genotype information display section G10 is a display label, and indicates the estimation method to estimate the genotype by the estimator 5. When the genotype has been estimated by the imputation algorithm, the genotype display section G10 displays the reference haplotype data, haplotype data of the patient (specimen), the haplotype data after the phasing, the haplotype data after the imputation, and the like as illustrated in FIG. 33. The haplotype data after the imputation includes the estimated genotype. The estimated genotype (alleles) is displayed in the base sequence field of the SNP information display section G9. Also, the genotype information display section G10 may display the ratio of the genotype of HapMap in the same or similar manner as in FIG. 32.

It should be noted that, when the estimator 5 estimates the genotype by the k-nearest neighbor algorithm, the genotype information display section G10 may display information displayed on the specimen list display section G4, the selection result display section G5, the genotype display section G6, and the like in FIG. 31.

Second Embodiment

A second embodiment is described with reference to FIGS. 34 to 58. This embodiment describes the estimation method to estimate the genotype using a thresholding method. The "thresholding method" as used herein refers to the method of estimating the genotype in which learning of a correspondence relationship between an interval of the signal intensity and the genotype is carried out, and the genotypes of the respective specimens are estimated on the basis of the learned correspondence relationships. The respective intervals of signal intensity are defined by the thresholds of the signal intensity. Details of the thresholding method will be described later.

Figures 34, 35:
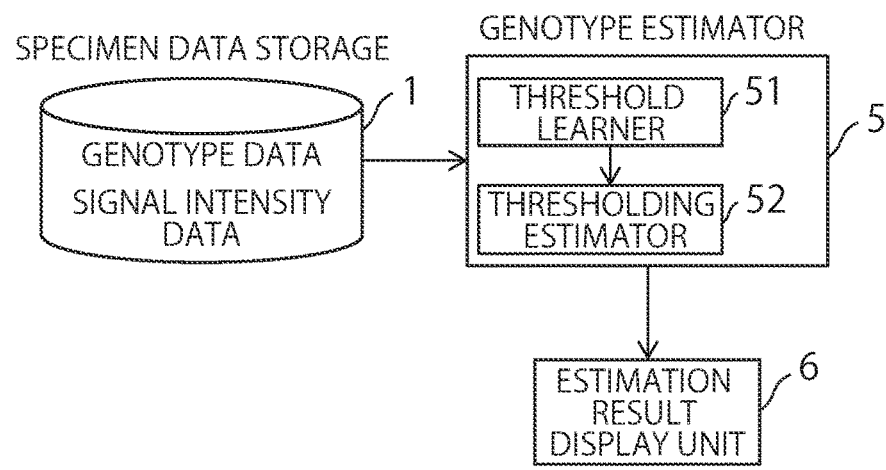
FIG. 34 is a block diagram illustrating the functional features of the genotype estimation device in accordance with a second embodiment.
FIG. 35 is a diagram illustrating exemplary genotype data.

First, the functional features of the estimation device in accordance with this embodiment is described with reference to FIGS. 34 and 35. FIG. 34 is a block diagram that illustrates the functional features of the estimation device in accordance with this embodiment. As illustrated in FIG. 34, this estimation device includes the specimen data storage 1, the estimator 5, and the display unit 6. The following describes the differences from the first embodiment.

According to this embodiment, the specimen data storage 1 stores therein, as the specimen data, the genotype data and the signal intensity data but does not include the clustering data. Also, the estimation device does not include the reference data storage 2, the acquirer 3 and the determiner 4.

This is because the thresholding method does not use the clustering data, the reference data, and the clustering strength. As will be described later, when the estimation method in accordance with this embodiment and the estimation method in accordance with the first embodiment are both used, the clustering data may be stored in the specimen data storage 1 and the estimation device may include the reference data storage 2, the acquirer 3, and the determiner 4.

Also, the estimator 5 includes a threshold learner 51 and a thresholding-method estimator 52.

The threshold learner 51 (hereinafter referred to as "learner 51") carries out learning of the correspondence relationship between the interval of signal intensity used in the thresholding method and the genotype on the basis of the signal intensity of the Fullcall SNP. Specifically, the learner 51 carries out learning of the correspondence relationship between the threshold defining the interval of the signal intensity and the genotype.

The Fullcall SNP refers to an SNP for which the genotypes of all the specimens are determined by the DNA microarray technology, i.e., an SNP all the specimens of which are known specimens. In contrast, an SNP for which the genotype of at least one specimen was not determined by the DNA microarray technology, i.e., an SNP including at least one unknown specimen is referred to as Nocall SNP.

Here, the Fullcall SNP and the Nocall SNP are specifically described with reference to FIG. 35. FIG. 35 is a diagram that illustrates an example of the genotype data stored in the specimen data storage 1. In the example of FIG. 35, with regard to the SNPs "rs00001" and "rs999999," the genotypes of all the specimens are already determined. Accordingly, the SNPs "rs00001" and "rs999999" are Fullcall SNPs. In contrast, with regard to the SNPs "rs000002" and "rs000003," the specimens "02" and "01" are unknown specimens, respectively. Hence, the SNPs "rs000002" and "rs000003" are Nocall SNPs. In this manner, the learner 51 can identify the Fullcall SNPs and the Nocall SNPs by referring to the genotype data.

The learner 51 extracts the Fullcall SNPs from the genotype data in order to learn the thresholds, and extracts the signal intensities of the respective specimens of the Fullcall SNPs from the signal intensity data. If values of "n" types of signal intensity are included in the signal intensity data, the learner 51 may extract any one type of signal intensity to be subjected to the learning. The types of signal intensity about which the learner 51 carries out learning of the thresholds can be specified as appropriate by the user of the estimation device. In the following description, the descriptions are provided on the basis of an exemplary case where the learner 51 extracts the signal intensity "x1" and learns the thresholds of the signal intensity "x1."

Also, the number of the thresholds which the learner 51 learns can be specified as appropriate by the user of the estimation device and one threshold or multiple thresholds may be specified. It is preferable that the number of the thresholds is specified in accordance with the types of genotype included in the respective SNPs.

The number of the intervals of the signal intensity to be defined is larger by one than the number of the thresholds. Accordingly, if there are maximum "X" types of genotype included in the respective SNPs, then it may be considered that the learner 51 carries out learning of, for example, "X−1" thresholds.

In the following description, the explanations are provided based on an exemplary case where the learner 51 carries out learning of two thresholds, i.e., the threshold "$x_l$" (the first threshold) and the threshold "$x_r$" (the second threshold) that is larger than "$x_l$". This envisages a case where maximum three genotypes are included in the individual SNPs in the same or similar manner as in the first embodiment.

Details of the threshold of the signal intensity and the method of learning the threshold will be described later.

The thresholding-method estimator 52 (hereinafter referred to as "estimator 52") estimates the genotypes of the respective specimens of the Nocall SNPs on the basis of the correspondence relationships learned by the learner 51 between the interval (the threshold) of the signal intensity and the genotype. As has been discussed in the foregoing description, the Nocall SNP includes the unknown specimen and the known specimen. Accordingly, in this embodiment, not only the estimation of the genotype of the unknown specimen but also the estimation of the genotype of the known specimen (re-determination) is carried out.

For example, in the first embodiment, with regard to the SNP "rs000002" of FIG. 35, the estimation is only carried out for the genotype of the specimen "02" which is an unknown specimen. In contrast, in this embodiment, with regard to SNP "rs000002," the genotype of the specimen "02" which is the unknown specimen is estimated and the genotypes of the specimens "01" and "N" which are known specimens are estimated as well. The estimation method to estimate the genotype using the thresholding method will be described later.

It should be noted that the hardware configuration of the estimation device in accordance with this embodiment is the same as that of the above-described first embodiment. Specifically, the above-described functional features of the estimation device are realized by the computer 100 executing the estimation program.

Next, the operation of the estimation device in accordance with this embodiment is specifically described with reference to FIGS. 36 to 58. In the following description, the operation of the learner 51 and the operation of the estimator 52 are separately described in this order.

Figure 36:
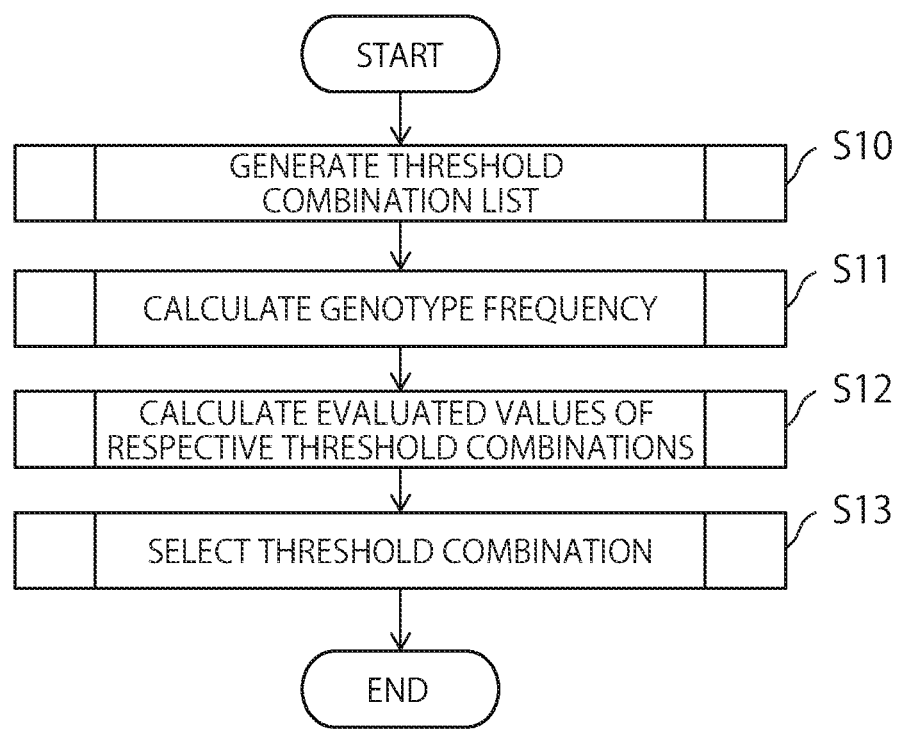
FIG. 36 is a flowchart illustrating an outline of a learning method of learning the threshold of signal intensity.

First, the operation of the learner 51 is described with reference to FIGS. 36 to 50. In the following description, the explanations are provided based on an exemplary case where the learner 51 carries out learning of two thresholds "$x_l$" and "$x_r$" (accordingly three intervals) of the signal intensity "x1." FIG. 36 is a flowchart that illustrates the outline of the method of learning the threshold. Details of the individual steps will be described later.

First, in step S10, the learner 51 generates a threshold combination list. The threshold combination list as used herein is a list that includes a plurality of threshold combinations. The threshold combination as used herein is a combination of threshold candidates. When two thresholds "$x_l$" and "$x_r$" ($x_l<x_r$) is to be learned, the threshold combination will be a combination of a candidate for the threshold "$x_l$" and a candidate for the threshold "$x_r$."

Next, in step S11, the learner 51 calculates the genotype frequency for evaluation of the respective threshold combinations included in the threshold combination list.

Subsequently, in step S12, the learner 51 calculates the evaluated values of the respective threshold combinations on the basis of the threshold candidates included in the respective threshold combinations and the genotype frequency In addition, in step S13, the learner 51 selects the threshold combination having the maximum evaluated value from the threshold combinations included in the threshold combination list. The respective threshold candidates included in the selected threshold combination are adopted as the thresholds for estimation of the genotype by the thresholding method.

Figure 37:
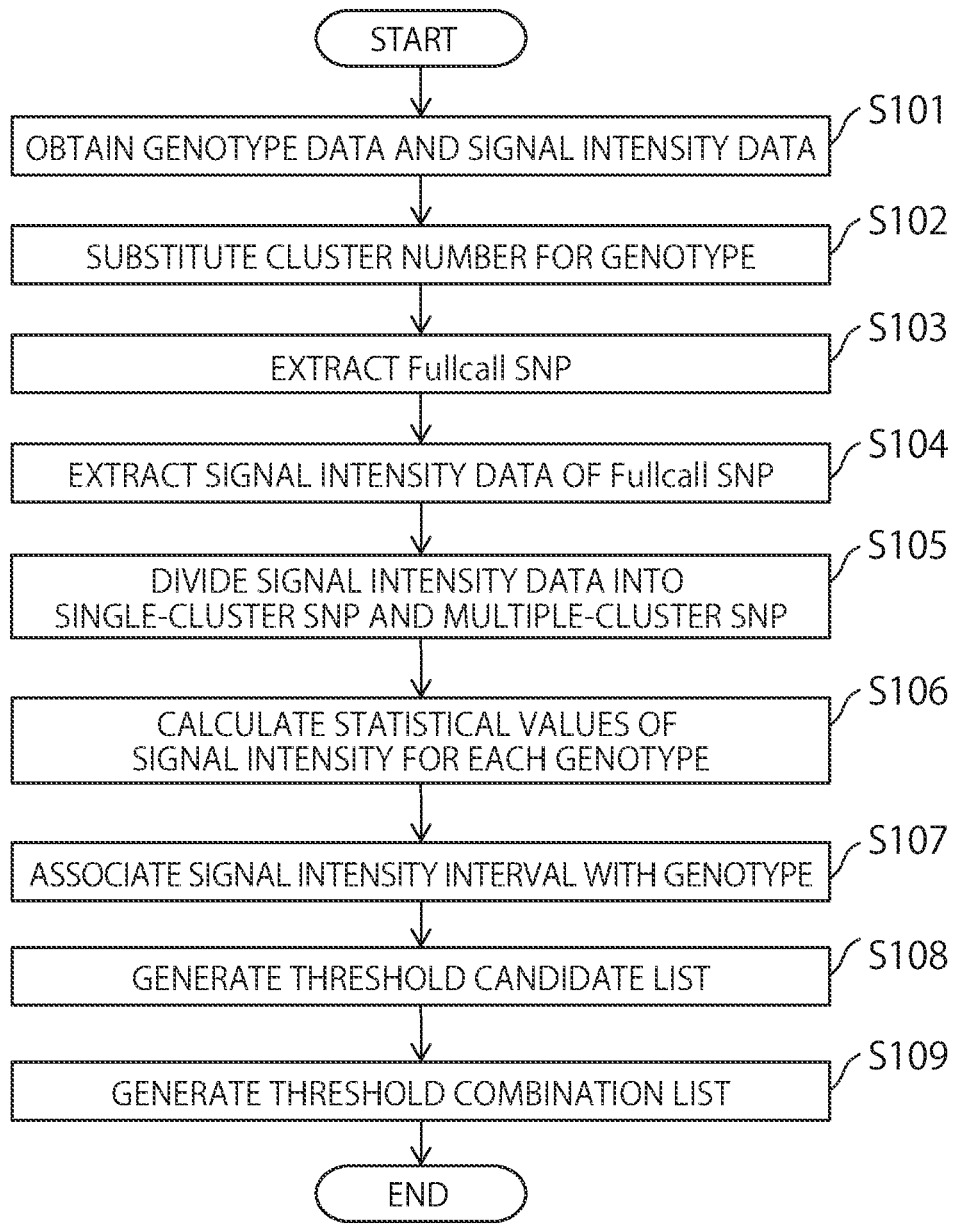
FIG. 37 is a flowchart illustrating a generation method to generate a threshold combination list.

In the following description, steps S10 to S13 are described in detail. FIG. 37 is a flowchart that illustrates an example of the generation method of the threshold combination list in step S10.

In step S101, the learner 51 acquires, from the specimen data storage 1, the genotype data of all the SNPs and the signal intensity data of the signal intensity "x1" of all the SNPs.

FIG. 38 is a diagram that illustrates an example of the acquired genotype data and the signal intensity data. In the example of FIG. 38, the genotype data and the signal intensity data of SNPs "rs000001" to "rs9999999" are acquired.

In step S102, the learner 51 substitutes the respective genotypes included in the genotype data acquired in step S101 by the cluster numbers. The cluster numbers are values assigned in accordance with the relative positions of the respective clusters in the clustering map. The learner 51 first assigns the cluster numbers to the respective clusters of the respective SNPs.

Figures 39, 40, 41:
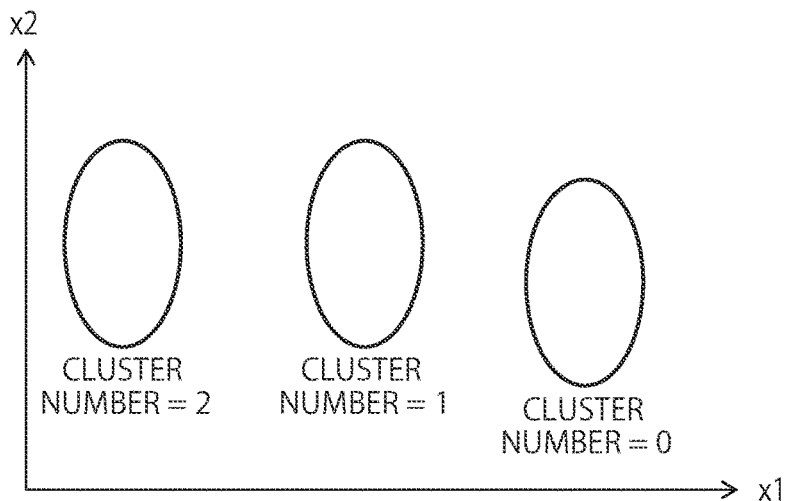
FIG. 39 is a diagram illustrating an exemplary assignment method to assign the cluster number.
FIG. 40 is a diagram illustrating exemplary genotype data after substitution.
FIG. 41 is a diagram illustrating exemplary signal intensity data of a Fullcall SNP.

FIG. 39 is a diagram that illustrates an example of the assignment method of the cluster numbers. In the example of FIG. 39, the cluster numbers 0, 1, and 2 are assigned to the clusters starting from the cluster residing at the right portion of the clustering map. This is equivalent to assigning the cluster numbers 0, 1, and 2 starting from the cluster having the highest signal intensity "x1" of its center of gravity.

The learner 51 calculates the signal intensity "x1" of the center of gravity of the respective clusters from the genotype data and the signal intensity data acquired in step S101 and is thus allowed to assign the cluster numbers thereto. Also, when the cluster coordinate data is stored in the specimen data storage 1, the learner 51 may acquire the cluster coordinate data from the specimen data storage 1, refer to the acquired cluster coordinate data, and assign the cluster number.

The cluster numbers are assigned on a per-SNP basis by the same method. Accordingly, it may happen that, in a certain SNP, the cluster number 0 is assigned to the cluster of the genotype "AA," and, in another SNP, the cluster number 0 is assigned to the cluster of the genotype "CC."

The learner 51, after having assigned the cluster numbers to the individual clusters, substitutes the genotypes of the individual specimens by the cluster numbers assigned to the clusters in which the specimens are included. For example, when the cluster number 0 is assigned to a certain cluster, the learner 51 substitutes the genotypes of the respective specimens included in this cluster by 0.

FIG. 40 is a diagram that illustrates an example of the genotype data after the substitution of the genotypes by the cluster numbers. The genotype data of FIG. 40 corresponds to the genotype data of FIG. 38. Referring to FIG. 40, 0, 1, and 2 are the cluster numbers that correspond to the respective genotypes whilst −1 is the cluster number that corresponds to the fact that the genotype is not determined.

For example, with regard to the SNP "rs000001," the genotype "CG" is substituted by the cluster number 1, and the genotype "CC" by the cluster number 2. Also, with regard to the SNP "rs000002," the genotype "AT" is substituted by the cluster number 1 and the genotype "TT" by the cluster number 2. This indicates the fact that the relative position of the cluster of the genotype "CG" in the SNP "rs000001" is identical with the relative position of the genotype "AT" in the SNP "rs000002."

Although, the cluster numbers are assigned to the individual clusters in the descending order of the signal intensity "x1" in the example of FIG. 39, they may be assigned to them in the ascending order of the signal intensity "x1," or the descending order or ascending order of the signal intensity "x2."

In the following description, the genotypes of the individual specimen are represented by the cluster numbers. For example, the genotype of the specimen 01 of the SNP "rs000001" of FIG. 40 is represented as genotype 1.

In step S103, the learner 51 refers to the genotype data after the substitution and extracts the Fullcall SNP. For example, when the genotype data of FIG. 40 is referred to, the SNPs "rs000001," "rs999998," and "rs999999" are extracted as the Fullcall SNPs.

In step S104, the learner 51 extracts, from the signal intensity data acquired in step S101, the signal intensity data of the Fullcall SNPs extracted in step S103.

FIG. 41 is a diagram that illustrates an example of the signal intensity data of the extracted Fullcall SNPs. The signal intensity data of FIG. 41 are the signal intensity data of the Fullcall SNPs extracted from the signal intensity data of FIG. 38.

In step S105, the learner 51 divides the signal intensity data of the Fullcall SNPs extracted in step S104 into the signal intensity data of single-cluster SNPs and the signal intensity data of multiple-cluster SNPs.

The single-cluster SNP as used herein refers to an SNP that includes only one type of genotype as the determination result. Specifically, the single-cluster SNP is an SNP for which all the specimens are determined as being of the same genotype. In contrast, the multiple-cluster SNP as used herein refers to an SNP that includes multiple types of genotype as the determination result. SNPs having two or more types of genotype are all included in the multiple-cluster SNPs as the determination result. However, the two or more types of genotype as used herein does not include the above-described genotype −1.

The learner 51 counts the types of genotype included in the genotype data of the respective SNPs for division of the signal intensity data. If one single type of genotype is included in the genotype data of a certain SNP (for example, the genotype 1), then the learner 51 determines that this SNP is a single-cluster SNP. Also, if two or more types of the genotype is included in the genotype data of a certain SNP, then the learner 51 determines that this SNP is a multiple-cluster SNP. The learner 51 divides the signal intensity data of the Fullcall SNPs on the basis of the determination result of the SNP that has thus been obtained.

FIG. 42 is a diagram that illustrates an example of the signal intensity data of the single-cluster SNPs and the signal intensity data of the multiple-cluster SNPs. The signal intensity data of FIG. 42 is obtained by dividing the signal intensity data of FIG. 41. As can be appreciated from FIG. 40, the SNP "rs999998" is a single-cluster SNP which includes only one type of the genotype 0 and the SNP "rs000001" and "rs999999" are multiple-cluster SNPs which includes three types of the genotypes 0, 1, and 2. As a result, as illustrated in FIG. 42, the signal intensity data of the single-cluster SNP includes the signal intensity data of the SNP "rs999998" and the signal intensity data of the multiple-cluster SNPs includes the signal intensity data of the SNP "rs000001" and "rs999999."

The SNPs are divided into single-cluster SNP or SNPs and the signal intensity data of the multiple-cluster SNP or SNPs in this manner because there is a large difference between the distribution of the clusters in the single-cluster SNP and the distribution of the clusters in the multiple-cluster SNP. The estimation accuracy of the genotype can be improved when learning of the thresholds of signal intensity, estimation of the genotypes using the learned thresholds are performed for the single-cluster SNP and the multiple-cluster SNP.

It should be noted that, in this embodiment, the estimation device may process the single-cluster SNP and the multiple-cluster SNP together. In this case, the learner 51 does not carry out the division of the signal intensity data in step S105 but may carry out the subsequent processes for the single-cluster SNP and the multiple-cluster SNP together.

In step S106, the learner 51 refers to the signal intensity data of the single-cluster SNPs that has been divided in step S105 and calculates the statistical value of the signal intensity for each genotype. Also, the learner 51 refers to the signal intensity data of the multiple-cluster SNPs divided in step S105 and calculates the statistical value of the signal intensity for each genotype.

The statistical value of the signal intensity includes a minimum value, an average value, a maximum value, and a standard deviation value. The learner 51 refers to the genotype data after the substitution and extracts the signal intensity of the genotype 0 from the signal intensity data of the single-cluster SNPs (or multiple-cluster SNPs) after the division, and calculates the statistical value of the extracted signal intensity, and thereby can calculate the statistical value of the signal intensity of the genotype 0 of the single-cluster SNPs (or multiple-cluster SNPs). Other genotypes are calculated by the same or similar methods.

Figures 43, 44:
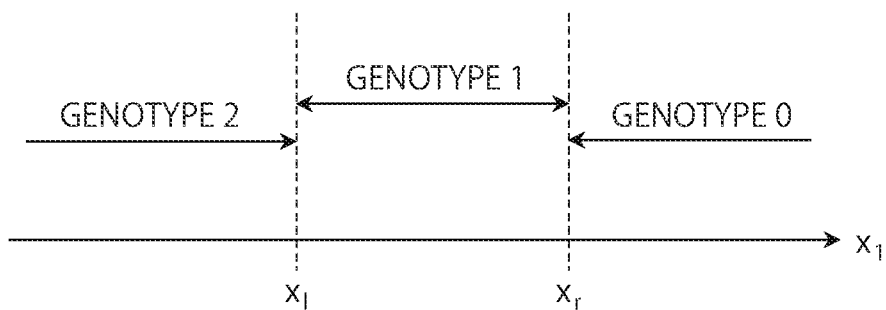
FIG. 43 is a diagram illustrating an exemplary statistical value of the signal intensity.
FIG. 44 is a diagram illustrating an exemplary correspondence relationship between an interval of the signal intensity and the genotype.

FIG. 43 is a diagram that illustrates an example of the statistical values of the signal intensity of the single-cluster SNP and the statistical value of the signal intensity of the multiple-cluster SNP. In the example of FIG. 43, the minimum value of the signal intensity of the genotype of the single-cluster SNP 2 is −6.29.

In step S107, the learner 51 associates the intervals of the signal intensity of the single-cluster SNP with the genotypes on the basis of the average value of the signal intensities of the respective genotypes of the single-cluster SNP. Also, the learner 51 associates the intervals of the signal intensity of the multiple-cluster SNP with the genotypes on the basis of the average value of the signal intensities of the respective genotypes of the multiple-cluster SNP.

When the learner 51 learns the two signal intensities "$x_l$" and "$x_r$," three intervals of the signal intensity are formed. The learner 51 associates the intervals with the genotypes such that an interval having a lower signal intensity is associated with a genotype having a smaller average value of the signal intensities.

FIG. 44 is a diagram that illustrates an example of the correspondence relationship between the intervals of the signal intensity and the genotypes. The correspondence relationship of FIG. 44 is based on the average value of the signal intensities of FIG. 43. In the example of FIG. 43, the average values of the signal intensities of the genotypes 2, 1, and 0 become smaller in this order. As a result, in the example of FIG. 44, the genotypes 2, 1, and 0 are each associated with one of the intervals in the ascending order of the signal intensity. Specifically, the genotype 2 is associated with an interval whose signal intensity is less than "$x_l$," the genotype 1 is associated with the interval whose signal intensity is not less than "$x_l$" and not larger than "$x_r$," and the genotype 0 is associated with the interval whose signal intensity is larger than "$x_r$."

In step S108, the learner 51 generates a threshold candidate list of the single-cluster SNP on the basis of the statistical values of the single-cluster SNP calculated in step S106. Also, the learner 51 generates a threshold candidate list of the multiple-cluster SNP on the basis of the statistical values of the multiple-cluster SNP calculated in step S106. The "threshold candidate list" as used herein refers to a list that includes multiple threshold candidates. The threshold candidate as used herein refers to a candidate of the thresholds "$x_l$" and "$x_r$," of the signal intensity.

The threshold candidates of the single-cluster SNP (or multiple-cluster SNP) includes, by way of example and is not limited to, the minimum value, average value, maximum value, and average value+N×standard deviation (where "N" is an integer) of the signal intensities of the respective genotypes of the single-cluster SNP (or multiple-cluster SNP).

FIG. 45 is a diagram that illustrates examples of the threshold candidate list of the single-cluster SNP and the threshold candidate list of the multiple-cluster SNP. The threshold candidate list of FIG. 45 corresponds to the statistical value of FIG. 43, and includes nine threshold candidates (minimum value, average value, and maximum value of the respective genotypes). For example, the threshold candidate −6.29 included in the threshold candidate list of the single-cluster SNP is the minimum value of the signal intensity of the genotype of the single-cluster SNP 2.

Also, the threshold candidate of the single-cluster SNP (or multiple-cluster SNP) may be, for example, a value that divides the section between the maximum value and the minimum value of the statistical values of the single-cluster SNP (or multiple-cluster SNP) at even intervals. In this case, the respective threshold candidates "$x_i$" are calculated in accordance with the following expression.

[Expression 8]

$$x_i = x_{min} + i \times d \text{ for } i = 0, 1, 2, \ldots, n-1 \quad (10)$$

$$d = \frac{x_{max} - x_{min}}{n-1} \quad (11)$$

In the above expressions (10) and (11), "n" is the number of the threshold candidates included in the threshold candidate list, "$x_{min}$" is the minimum value of the statistical value, $x_{max}$ is the maximum value of the statistical value, and "d" is an interval of the threshold candidates. In the example of FIG. 43, the minimum value of the statistical value "$x_{min}$" of the single-cluster SNP corresponds to the minimum value −6.29 of the signal intensity of the genotype 2, and the maximum value "$x_{max}$" corresponds to the maximum value 7.46 of the signal intensity of the genotype 0.

It should be noted that the threshold candidates included in the threshold candidate list are not limited to the above-described ones and can be generated by any appropriate method from the statistical value of the signal intensity. Also, the threshold candidate list may include any appropriate values specified in advance as the threshold candidates.

In step S109, the learner 51 refers to the threshold candidate list of the single-cluster SNP generated in step S108 and generates the threshold combination list of the single-cluster SNP. Also, the learner 51 refers to the threshold candidate list of the multiple-cluster SNP generated in step S108 and generates the threshold combination list of the multiple-cluster SNP.

The threshold combination list is, as has been discussed in the foregoing description, a list that includes multiple threshold combinations. The learner 51 combines the threshold candidates included in the threshold candidate list and generates the threshold combination, and generates the threshold combination list that includes multiple threshold combinations.

If the threshold candidate list includes "n" threshold candidates and the threshold combination includes "r" threshold candidates, then up to "n!/(n−r)!r!" threshold combinations are generated. Accordingly, if the threshold candidate list of the single-cluster SNP includes nine threshold candidates and the threshold combination includes two threshold candidates "$x_l$" and "$x_r$," then up to 36 threshold combinations are generated.

FIG. 46 is a diagram that illustrates an example of the threshold combination list of the single-cluster SNP. The threshold combination list of FIG. 46 corresponds to the threshold candidate list of FIG. 45. The threshold combination list of FIG. 46 includes 36 threshold combinations. In the example of FIG. 46, for example, the threshold combination 1 is $(x_l, x_r) = (−6.29, 7.46)$. The threshold combination lists as in FIG. 46 is also generated for the multiple-cluster SNP.

Next, the calculation method to calculate the genotype frequency in step S11 is described in detail. After creating the threshold combination list, the learner 51 calculates the genotype of the single-cluster SNP frequency and the genotypes of the multiple-cluster SNP frequency. The genotype frequency as used herein refers to the number of specimens having the signal intensity included in the interval of the signal intensity defined by two adjacent threshold candidates. The genotype frequency is calculated for each genotype.

The learner 51 refers to the signal intensity data divided in step S105, the genotype data after the substitution, and the threshold candidate list generated in step S108, and can thus calculate the genotype frequencies of the respective genotypes of the respective intervals of the single-cluster SNP and the multiple-cluster SNP.

For example, referring to the signal intensity data of the single-cluster SNP of FIG. 42, the signal intensity of the specimen 01 of the SNP "rs999998" is 0.3. Given this signal intensity, when the threshold candidate list of the single-cluster SNP of FIG. 45 is referred to, it is appreciated that it is included in the interval between the threshold candidate 0.69 and the threshold candidate 2.11. In addition, when the genotype data of FIG. 40 is referred to, the genotype of the specimen 01 of the SNP "rs999998" is 2. As a result, the genotype frequency of the genotype 2 of the interval between 0.69 and 2.11 of the single-cluster SNP is incremented by 1.

The learner 51 refers to the respective signal intensities included in the signal intensity data of the single-cluster SNP and increments the genotype frequencies of the respective genotypes of the respective intervals as described above, and calculates the genotype frequency of the single-cluster SNP. With regard to the multiple-cluster SNP as well, the genotype frequency is calculated by the same or similar method.

FIG. 47 is a diagram that illustrates an example of the genotypes of the single-cluster SNP frequencies. The genotype frequency of FIG. 47 corresponds to the threshold candidate list of FIG. 45. In the example of FIG. 47, in the interval between the threshold candidate −2.11 and the threshold candidate −1.79, the genotype frequency of the genotype 2 is large and the genotype frequency of the genotype 1 is small, and the genotype frequency of the genotype 0 is 0.

Next, the calculation method to calculate the evaluated value in step S12 and the selection method of the threshold combination in step S13 are described in detail. After calculating the genotype frequency, the learner 51 calculates the evaluated values of the respective threshold combinations of the single-cluster SNP, and selects the threshold combination of the single-cluster SNP on the basis of the calculated evaluated value. Also, the learner 51 calculates the evaluated values of the respective threshold combinations of the multiple-cluster SNP and selects the threshold combination of the multiple-cluster SNP on the basis of the calculated evaluated values.

First, the learner 51 carries out re-determination of the genotype of the single-cluster SNP in the Fullcall SNPs on the basis of the threshold combinations. The following describes two re-determination methods.

According to a first re-determination method, the learner 51 selects one threshold combination from the threshold combination list of the single-cluster SNP and extracts the signal intensities and the genotype of the specimens of the single-cluster SNP. The learner 51 then re-determines that the genotype of the specimen whose signal intensity is lower than "$x_l$" as being the genotype 2, re-determines that the genotype of the specimen whose signal intensity is not lower than "$x_l$" and not higher than "$x_r$" as being the genotype 1, and re-determines that the genotype of the specimen whose signal intensity is higher than "$x_r$" as being the genotype 0.

Figure 48:
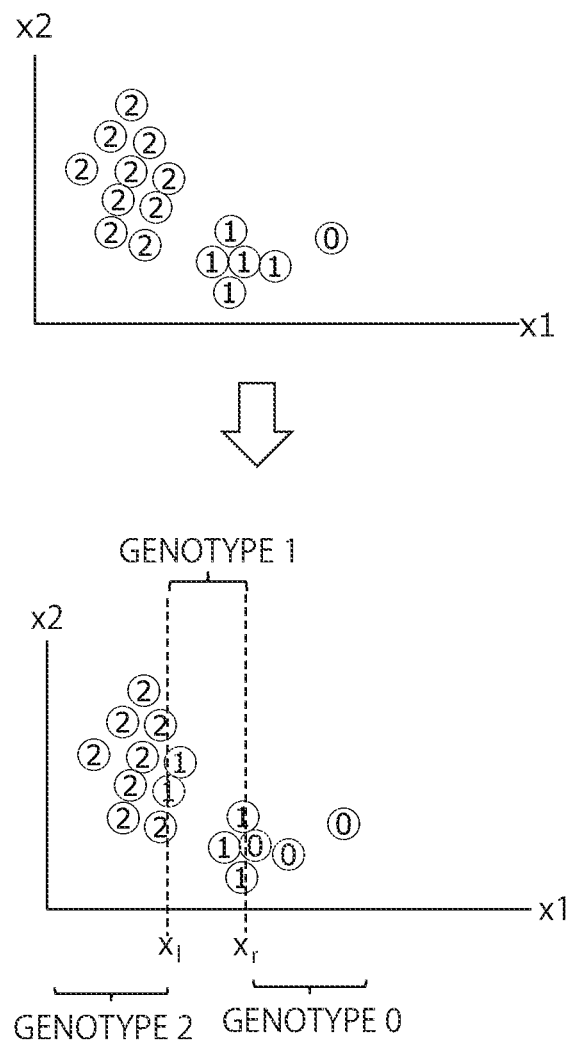
FIG. 48 is a diagram illustrating exemplary clustering maps before and after re-determination by a first re-determination method.

FIG. 48 is a diagram that illustrates an example of the clustering maps before and after the re-determination by the first re-determination method. Referring to FIG. 48, a circle indicates each specimen and the value in the circle indicates the value of the genotype. The upper figure of FIG. 48 indicates the genotype before the re-determination and the lower figure the genotype after the re-determination. As can be appreciated from FIG. 48, according to the first re-determination method, the genotypes of the specimens whose signal intensity is included in the interval between the threshold candidate "$x_l$" and the threshold candidate "$x_r$" are all re-determined as being the genotype 1.

In this manner, according to the first re-determination method, only the threshold combination is used and the genotype frequency is not used. Accordingly, when the first re-determination method is adopted, step S11 can be omitted.

In contrast, according to a second re-determination method, the genotype frequency is used. Specifically, according to the second re-determination method, the genotype of the specimen whose signal intensity is not lower than "$x_l$" and not higher than "$x_r$" is re-determined by the majority voting algorithm using the genotype frequency. Specifically, the specimen whose signal intensity is not lower than "$x_l$" and not higher than "$x_r$" is re-determined as being the genotype having the maximum genotype frequency in the interval in which the signal intensity of this specimen is included.

For example, if $(x_l, x_r)=(-2.11, 2.33)$, the signal intensity of a certain specimen is −2.00, and the genotype frequency illustrated in FIG. 47 has been obtained, then the genotype of this specimen is re-determined as being the genotype 2 having the maximum genotype frequency in the interval between −2.11 and −1.79.

Figures 49, 50:
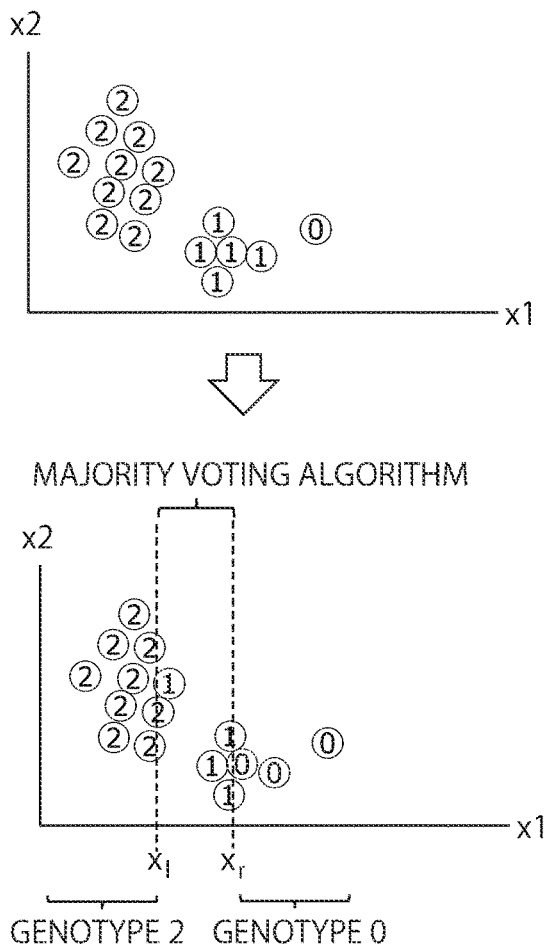
FIG. 49 is a diagram illustrating exemplary clustering maps before and after re-determination by a second re-determination method.
FIG. 50 is a diagram illustrating an exemplary threshold combination list including an evaluated value.

FIG. 49 is a diagram that illustrates an example of the clustering maps before and after the re-determination by the second re-determination method. As illustrated in FIG. 49, according to the second re-determination method, the specimen whose signal intensity is included in the interval between the threshold candidate "$x_l$" and the threshold candidate "$x_r$" is not always re-determined as being the genotype 1.

The learner 51, after having re-determined the genotype of the single-cluster SNP by the re-determination method as described above, calculates the agreement rate between the genotype before the re-determination and the genotype after the re-determination. For example, in the example of FIG. 48, the genotypes of 12 specimens before the re-determination among the 16 specimens are in agreement with their counterpart of the corresponding 12 specimens after the re-determination, so that the agreement rate is 0.75. Also, in the example of FIG. 49, the genotypes of 13 specimens before the re-determination among the 16 specimens are in agreement with their counterpart of the corresponding 13 specimens after the re-determination, so that the agreement rate is 0.81.

The agreement rate that has thus been calculated is used as the evaluated value of the threshold combination used in the re-determination. The learner 51 calculates, by the above-described method, calculates the evaluated value of the respective threshold combinations included in the threshold combination list of the single-cluster SNP. Also, the learner 51 calculates the evaluated value of the respective threshold combinations included in the threshold combination list of the multiple-cluster SNP by the same or similar method.

FIG. 50 is a diagram that illustrates an example of the threshold combination list including the evaluated values. In the example of FIG. 50, the evaluated value of the threshold combination 1 is 0.80, and the evaluated value of the threshold combination 24 is 0.97.

The learner 51 selects the threshold combination having the maximum evaluated value from the threshold combinations included in the threshold combination list of the single-cluster SNP. The respective threshold candidates included in the selected threshold combination is learned as the thresholds for estimation of the genotype of the single-cluster SNP by the thresholding method.

Also, the learner 51 selects the threshold combination having the maximum evaluated value from the threshold combinations included in the threshold combination list of the multiple-cluster SNP. The respective threshold candidates included in the selected threshold combination are learned as the thresholds for estimation of the genotypes of the multiple-cluster SNP by the thresholding method.

For example, in the example of FIG. 50, the threshold combination having the maximum evaluated value in the threshold combination list is the threshold combination 24, so that the threshold candidates included in the threshold combination 24 are learned as the thresholds for estimation of the genotype. Specifically, when the genotype is to be estimated by the thresholding method, −0.80 is used as the threshold "$x_l$" and 2.11 is used as the threshold "$x_r$."

By learning of the thresholds as described above, the estimation accuracy to estimate the genotypes by the thresholding method can be improved. This is because a larger evaluated value (higher agreement rate) of the threshold combination causes the estimation result of the genotype by this threshold combination and the estimation result of the genotype in the Fullcall SNP to become closer to each other. In general, since the estimation accuracy of the genotype in the Fullcall SNP is high, the threshold combination that can obtain an estimation result closer to the estimation result in the Fullcall SNP will have higher estimation accuracy.

Figure 51:
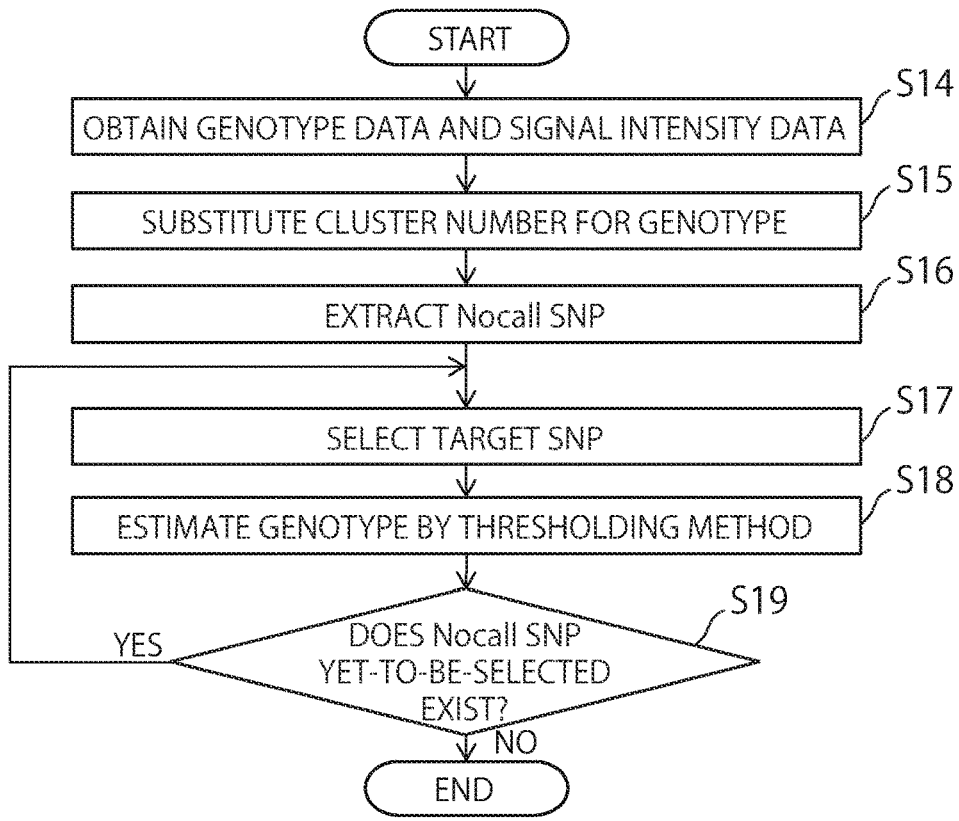
FIG. 51 is a flowchart illustrating an outline of an estimation method to estimate a genotype by a thresholding method.

Next, the estimation method to estimate the genotype using the thresholds by the estimator 52 is described with reference to FIGS. 51 to 58. In the following description, it is assumed that the thresholds "$x_l$" and "$x_r$" of the signal intensity have already been learned. FIG. 51 is a flowchart that illustrates the outline of the estimation method to estimate the genotype by the thresholding method.

First, in step S14, the estimator 52 acquires, from the specimen data storage 1, genotype data of all the SNPs and the signal intensity data of the signal intensity "x1" of all the SNPs.

Next, in step S15, the estimator 52 substitutes the respective genotypes acquired in step S14 by the cluster numbers. The substitution method of the genotypes has already been described in the context of step S102.

Subsequently, in step S16, the estimator 52 refers to the genotype data after the substitution and extracts the Nocall SNP. For example, when the genotype data of FIG. 40 is referred to, then the SNPs "rs000002" and "rs000003" are extracted as the Nocall SNPs.

Also, in step S17, the estimator 52 selects the target SNP from the Nocall SNPs extracted in step S16. The target SNP is an SNP to be subjected to the estimation of the genotype by the thresholding method. In this embodiment, as has been discussed in the foregoing description, learning of the threshold is carried out using all the Fullcall SNPs, but estimation of the genotypes is carried out for each of the individual Nocall SNPs. Any appropriate method may be used to select the target SNP.

After that, in step S18, the estimator 52 estimates the genotypes of the respective specimens of the target SNP selected in step S17 by the thresholding method. Details of step S18 will be described later.

If there is any Nocall SNP that has not been selected yet (YES in step S19) as the target SNP, then the estimator 52 selects the next target SNP from the yet-to-be-selected Nocall SNP (step S17). Thereafter, steps S17 to S19 are repeated until there is not a yet-to-be-selected Nocall SNP anymore.

Also, when there is not a yet-to-be-selected Nocall SNP anymore as the target SNP (NO in step S19), the estimator 52 completes the genotype estimation processing.

Here, the estimation method to estimate the genotype in step S18 is described in detail. In the following description, two estimation methods are independently described.

Figure 52:
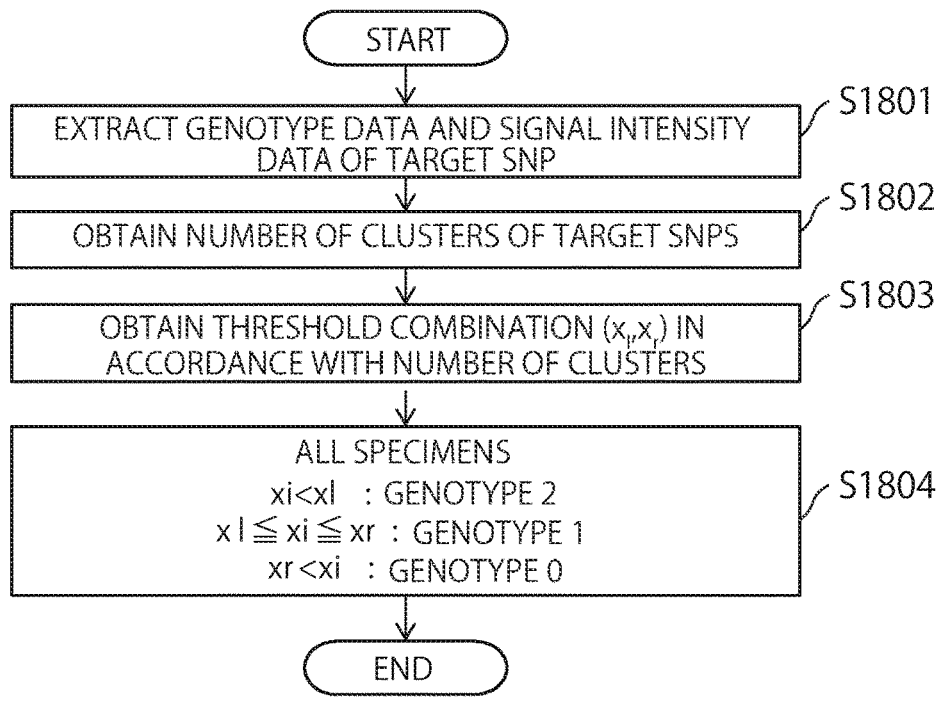
FIG. 52 is a flowchart illustrating a first estimation method.

First, a first estimation method is described. According to the first estimation method, the estimator 52 only uses the thresholds "$x_l$" and "$x_r$" of the signal intensity to estimate the genotypes of all the specimens of the target SNPs. FIG. 52 is a flowchart that illustrates the first estimation method.

In step S1801, the estimator 52 extracts the genotype data and the signal intensity data of the target SNP from the genotype data after the substitution and the signal intensity data.

In step S1802, the estimator 52 refers to the genotype data of the target SNP and acquires the number of clusters of the target SNP. The method of acquiring the number of clusters has already been described in the foregoing description. Specifically, the estimator 52 counts the types of genotype included in the genotype data of the target SNP and thereby acquires the number of clusters of the target SNP.

If the thresholds "$x_l$" and "$x_r$" of the signal intensity have not yet been learned with respect to the single-cluster SNP and the multiple-cluster SNP, respectively, then step S1802 may be omitted. In this case, the estimator 52 may execute the subsequent processes for the single-cluster SNP and the multiple-cluster SNP together.

In step S1803, the estimator 52 acquires, from the learner 51, the thresholds "$x_l$" and "$x_r$" of the signal intensity in accordance with the number of clusters of the target SNP. If the number of clusters of the target SNP is 1, the estimator 52 acquires the thresholds "$x_l$" and "$x_r$" of the single-cluster SNP. If the number of clusters of the target SNP is equal to or larger than 2, the estimator 52 acquires the thresholds "$x_l$" and "$x_r$" of the multiple-cluster SNP.

In step S1804, the estimator 52 estimates the genotypes of the respective specimens of the target SNP on the basis of the thresholds "$x_l$" and "$x_r$" acquired in step S1803. Specifically, the estimator 52 estimates the genotype of the specimen whose signal intensity "$x_i$" is lower than "$x_l$" ($x_i < x_l$) as being the genotype 2, estimates the genotype of the specimen whose signal intensity is not lower than "$x_l$" and not higher than "$x_r$" ($x_l \leq x_i \leq x_r$) as being the genotype 1, and estimates the genotype of the specimen whose signal intensity is higher than "$x_r$" ($x_r < x_i$) as being the genotype 0.

Figure 53:
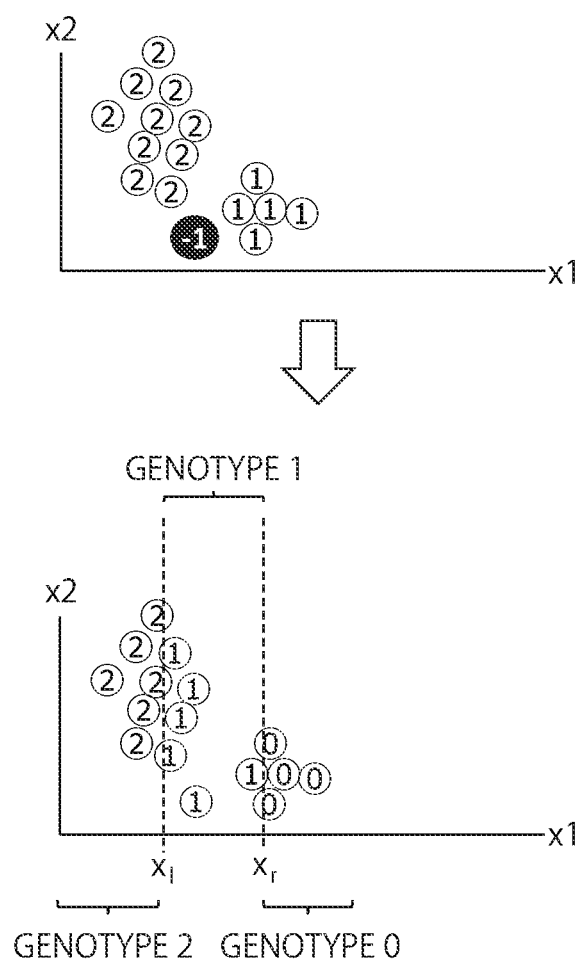
FIG. 53 is a diagram illustrating exemplary clustering maps before and after estimation by the first estimation method.

FIG. 53 is a diagram that illustrates an example of the clustering maps before and after the estimation by the first estimation method. The upper figure of FIG. 53 indicates the genotype before the estimation by the first estimation method, and the lower figure indicates the genotype after the estimation by the first estimation method. As can be appreciated from FIG. 53, according to the first estimation method, the genotypes of all the specimens including the unknown specimen and the known specimen are estimated on the basis of the thresholds "$x_l$" and $x_r$.

After that, the estimator 52 completes the estimation process of estimating the genotype of the target SNP. If there is any yet-to-be-selected Nocall SNP (YES in step S19), the estimator 52 selects the next target SNP (step S17).

Figure 54:
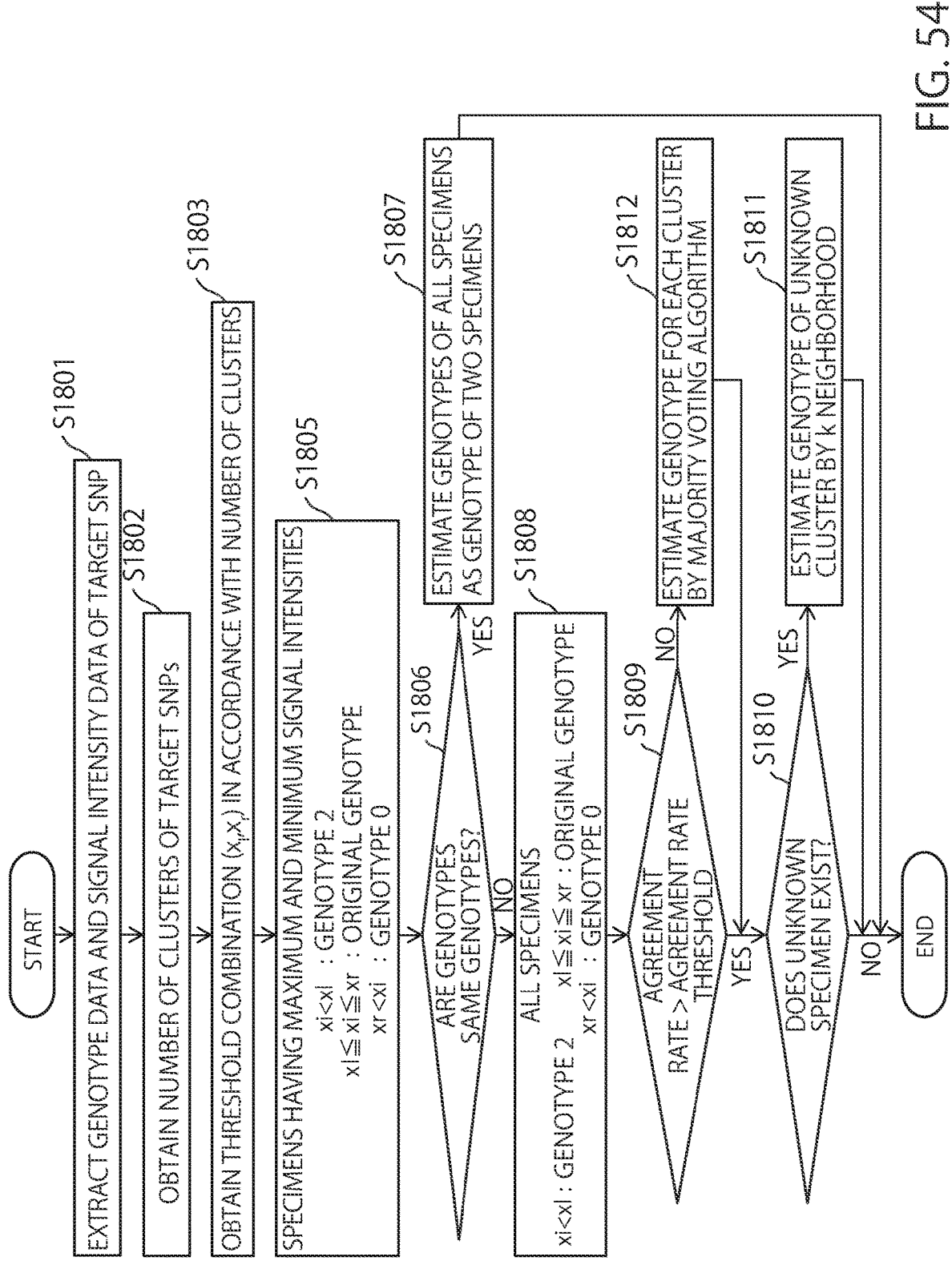
FIG. 54 is a flowchart illustrating a second estimation method.

Next, a second estimation method is described. According to the second estimation method, the estimator 52 uses thresholds "$x_l$" and "$x_r$" of the signal intensity, estimates the genotypes of the known specimens of the target SNP, and then estimates the genotype of the unknown specimen using the k-nearest neighbor algorithm. FIG. 54 is a flowchart that illustrates the second estimation method. Steps S1801 to S1803 of FIG. 54 are identical to those of the first estimation method and accordingly explanation thereof is not repeated.

In step S1805, the estimator 52 estimates the genotypes of the specimen having the maximum signal intensity and the specimen having the minimum signal intensity among the specimens of the target SNPs on the basis of the thresholds "$x_l$" and "$x_r$" acquired in step S1803. Specifically, the estimator 52 estimates the genotype of the specimen whose signal intensity is lower than "$x_l$" as being the genotype 2, estimates the genotype of the specimen whose signal intensity is not lower than "$x_l$" and not higher than "$x_r$" as being the original genotype, and estimates the genotype of the specimen whose signal intensity is higher than "$x_r$" as being the genotype 0.

Figure 55:
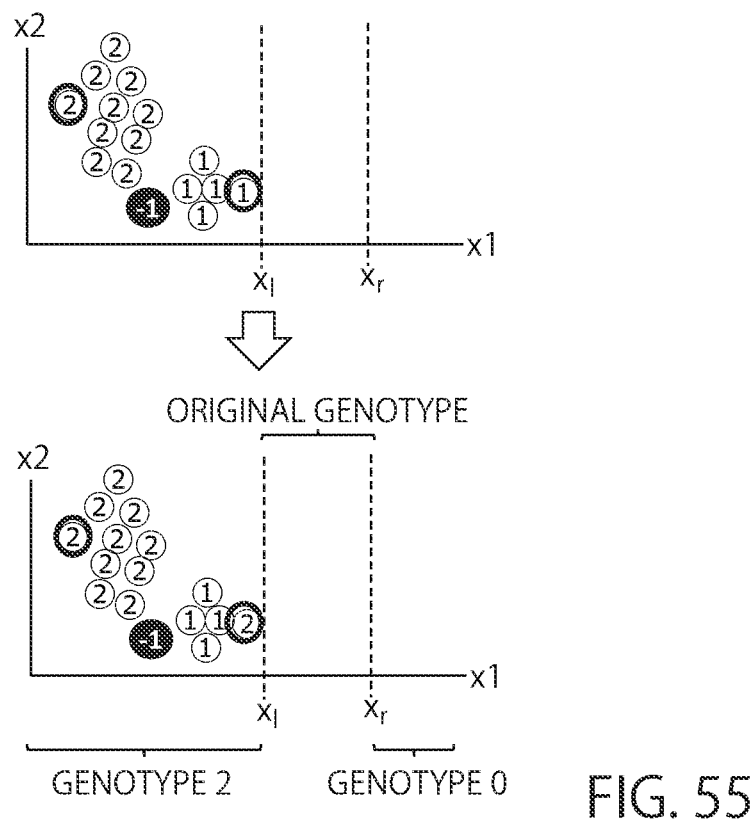
FIG. 55 is a diagram illustrating exemplary clustering maps before and after the estimation in step S1805.

FIG. 55 is a diagram that illustrates an example of the clustering maps before and after the estimation in step S1805. The upper figure of FIG. 55 indicates the genotype before the estimation, and the lower figure indicates the genotype after the estimation. In the example of FIG. 55, as illustrated in the upper figure, the genotype of the specimen having the minimum signal intensity (the leftmost specimen) is the genotype 2, and the genotype of the specimen having the maximum signal intensity (the rightmost specimen) is the genotype 1. Also, the signal intensities of these two specimens are both lower than the threshold "$x_l$." In this case, as illustrated in the lower figure, in step S1805, the genotypes of the two specimens are both estimated as being the genotype "2." In contrast, if the signal intensity of the rightmost specimen of FIG. 55 is not lower than "$x_l$" and not higher than "$x_r$," the genotype of the rightmost specimen is estimated as being the genotype 1 (the original genotype) in step S1805.

In step S1806, the estimator 52 determines whether or not the genotypes of the two specimens estimated in step S1805 are the same genotypes. If the genotypes of the two specimens are the same genotype (YES in step S1806), the process proceeds to step S1807.

In step S1807, the estimator 52 estimates the genotypes of all the specimen as being the same genotype as the genotypes of the two specimens estimated in step S1805. This is because, if the genotypes of the specimen having the maximum signal intensity and the genotype of the specimen having the minimum signal intensity are both estimated as being the same genotype X, then the genotypes of all the specimens are estimated as the same genotype "X" in the subsequent processes The amount of calculation of the estimation device can be reduced by estimating the genotypes of the two specimens only and estimating the genotypes of all the specimens on the basis of the estimation result in steps S1805 to S1807.

Figure 56:
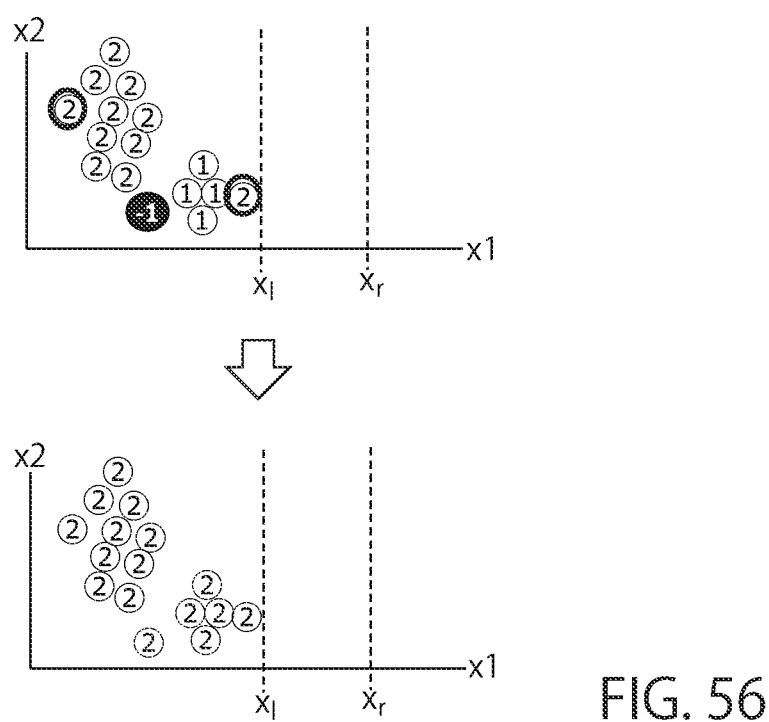
FIG. 56 is a diagram illustrating exemplary clustering maps before and after the estimation in step S1807.

FIG. 56 is a diagram that illustrates an example of the clustering maps before and after the estimation in step S1807. The upper figure of FIG. 56 indicates the genotype before the estimation and, the lower figure indicates the genotype after the estimation. The upper figure of FIG. 56 corresponds to the lower figure of FIG. 55. In the example of FIG. 56, since the genotypes of the leftmost and rightmost specimens are both estimated as being the genotype 2, the genotypes of all the specimens are estimated as being the genotype 2 in step S1807. As can be appreciated from FIG. 56, since not only the genotype of the known specimen but also the genotype of the unknown specimen is estimated in step S1807, the k-nearest neighbor algorithm is not used.

After that, the estimator 52 completes the estimation process of estimating the genotypes of the target SNP. If there is any yet-to-be-selected Nocall SNP (YES in step S19), the estimator 52 selects the next target SNP (step S17).

Meanwhile, if the genotypes of the two specimens estimated in step S1805 are different from each other (NO in step S1806), the process proceeds to step S1808.

In step S1808, the estimator 52 estimates the genotypes of all the specimens of the target SNP on the basis of the thresholds "$x_l$" and "$x_r$" acquired in step S1803. The estimation method corresponds to the above-described step S1805. Specifically, the estimator 52 estimates the genotype of the specimen whose signal intensity is lower than "$x_l$" as being the genotype 2, estimates the genotype of the specimen whose signal intensity is not lower than "$x_l$" and not higher than "$x_r$" as being the original genotype, and estimates the genotype of the specimen whose signal intensity is higher than "$x_r$" as being the genotype 0.

Figure 57:
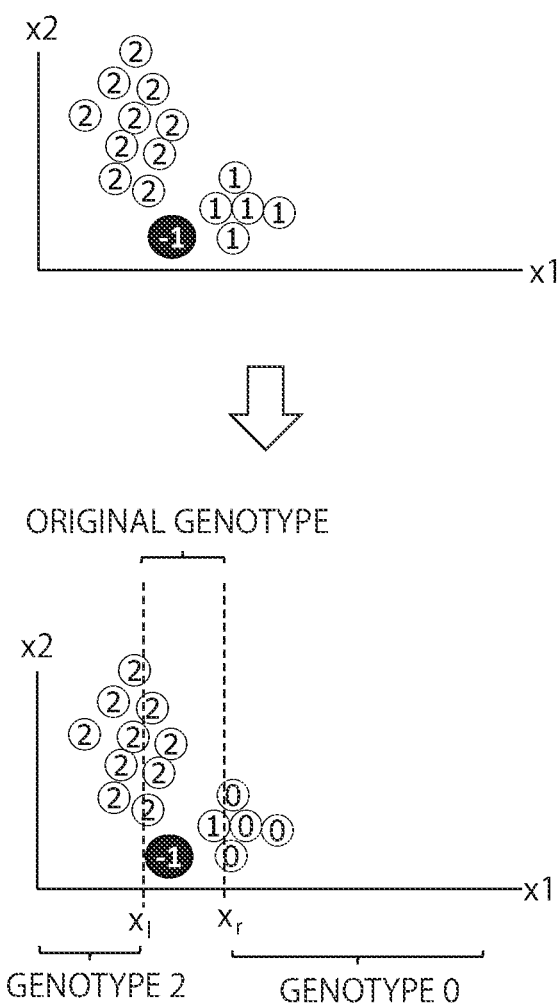
FIG. 57 is a diagram illustrating exemplary clustering maps before and after the estimation in step S1808.

FIG. 57 is a diagram that illustrates an example of the clustering maps before and after the estimation in step S1808. The upper figure of FIG. 57 indicates the genotype before the estimation and, the lower figure indicates the genotype after the estimation. In the example of FIG. 57, as the result of estimation in step S1808, the genotypes of four specimens whose signal intensities are larger than "$x_r$" are estimated as being the genotype 0.

In step S1809, the estimator 52 calculates the agreement rate between the genotype before the estimation in step S1808 and the genotype after the estimation, and determines whether or not the calculated agreement rate is larger than the agreement rate threshold. The agreement rate threshold may be specified as appropriate. In the example of FIG. 57, since the genotypes of 12 specimens out of the 16 specimens before the estimation are in agreement with their counterpart of the corresponding 12 specimens after the estimation, the agreement rate is 0.75.

If the agreement rate is larger than the agreement rate threshold (YES in step S1809), the process proceeds to step S1810.

In step S1810, the estimator 52 determines whether or not an unknown specimen exists among the specimens of the target SNP. As has been discussed in the foregoing, the unknown specimen corresponds to a specimen whose genotype is −1. As a result, the estimator 52 can determine whether or not the unknown specimen exists by referring to the estimation result in step S1808 and checking whether or not the specimen of the genotype −1 exists.

When the unknown specimen does not exist in the specimen of the target SNP (NO in step S1810), the estimator 52 completes the estimation process of estimating the genotypes of the target SNP. If there is any yet-to-be-selected Nocall SNP (YES in step S19), the estimator 52 selects the next target SNP (step S17).

Meanwhile, an unknown specimen exists in the specimen of the target SNP as in the example of FIG. 57 (YES in step S1810), the process proceeds to step S1811.

In step S1811, the estimator 52 extracts the unknown specimen or specimens from the specimens of the target SNP, and estimates the genotypes of the respective unknown specimens by the k-nearest neighbor algorithm. At this point, the estimation result in step S1808 is used as the genotype of the known specimen(s). The estimation method to estimate the genotype by the k-nearest neighbor algorithm has already been described in the context of the first embodiment. The estimator 52 may extract, for example, "k" nearest-neighbor specimens (or cluster lines) closest to the unknown specimen (having the shortest Euclidean distance in the clustering map) and estimate the most genotypes among the genotypes of the extracted specimens (or cluster lines) as being the genotype of the unknown specimen.

After that, the estimator 52 completes the estimation process of estimating the genotype of the target SNP. If there is any yet-to-be-selected Nocall SNP (YES in step S19), the estimator 52 selects the next target SNP (step S17).

In contrast, if the agreement rate is equal to or less than the agreement rate threshold (NO in step S1809), the process proceeds to step S1812.

In step S1812, the estimator 52 estimates the genotype for each cluster by the majority voting algorithm. First, the estimator 52 classifies the known specimens of the target SNP for each genotype before the estimation in step S1811, and generates clusters that correspond to the respective genotypes. Each cluster includes a specimen having a genotype that corresponds to the cluster.

Next, the estimator 52 refers to the estimation result in step S1808 and estimates the most genotypes among the genotypes after the estimation of the specimens included in the respective cluster as being the genotype of the cluster. Also, the estimator 52 estimates the genotypes of all the specimens included in the respective clusters as being the genotype of the cluster in which this specimen is included.

Figure 58:
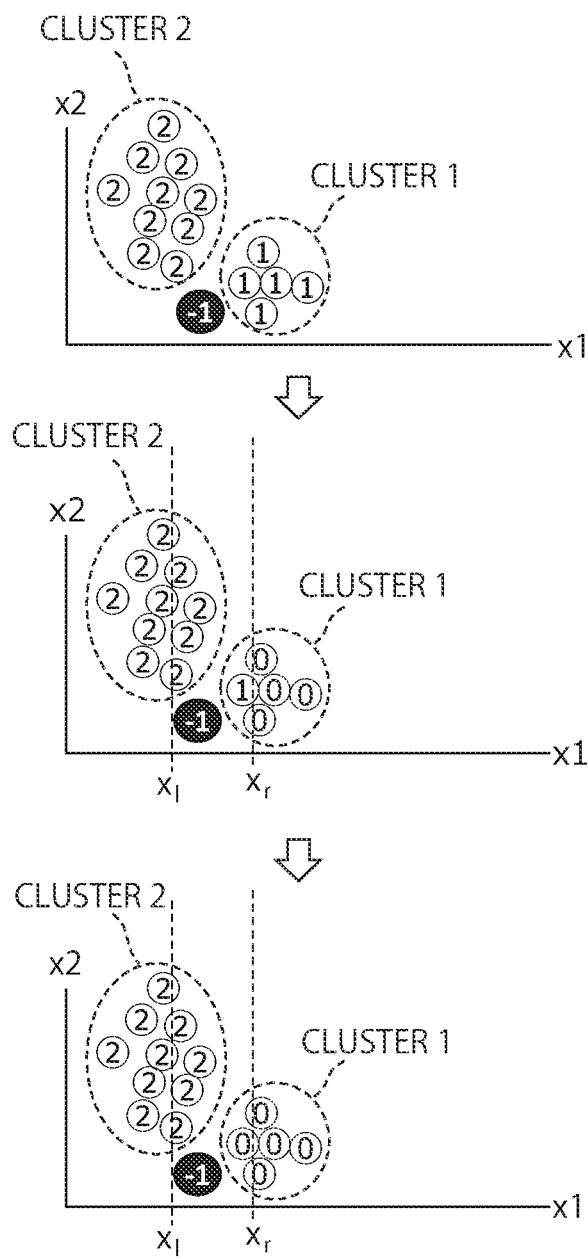
FIG. 58 is a diagram illustrating exemplary clustering maps before and after the estimation in steps S1808 and S1812.

FIG. 58 is a diagram that illustrates an example of the clustering maps before and after the estimation in steps S1808 and S1812. The upper figure of FIG. 58 indicates the genotype before the estimation in step S1808, the intermediate figure indicates the genotype after the estimation in step S1808, and the lower figure indicates the genotype after the estimation in step S1812. The upper figure and the intermediate figure of FIG. 58 correspond to FIG. 57.

In the example of FIG. 58, the estimator 52 first generates the cluster 1 that includes four specimens of the genotype 1, and the cluster 2 that includes 11 specimens of the genotype 2 (see the upper figure).

Next, the estimator 52 refers to the estimation result in step S1808 and estimates the most genotypes among the genotypes after the estimation of the specimen included in the cluster 1 as being the genotype of the cluster 1 (see the intermediate figure). In the example of FIG. 58, the cluster 1 includes three specimens of the genotype 0 and one specimen of the genotype 1. Accordingly, the estimator 52 estimates the genotype of the cluster 1 as being the genotype 1.

Also, the estimator 52 estimates the genotypes of all the specimens included in the cluster 1 as being the genotype 0 which is the genotype of the cluster 1 (see the lower figure). The estimator 52 also estimates the genotypes of the individual specimen included in the cluster 2 by the same or similar method. As a result, the genotypes of all the specimens included in the cluster 2 are estimated as being of the genotype 2.

After that, the process proceeds to step S1810. The processes following step S1810 have already been described in the foregoing. In step S1811, the genotype of the unknown specimen is estimated by the k-nearest neighbor algorithm.

As has been described in the foregoing, the estimation device in accordance with this embodiment estimates the genotype of the Nocall SNP by the thresholding method using the thresholds of the signal intensity. Since the thresholds are learned using the signal intensity data of the Fullcall SNP whose genotypes are accurately determined, the estimation device can accurately estimate the genotype of the Nocall SNP.

Also, the estimation method in accordance with this embodiment can estimate the genotype without using the reference data and thus can be used even in a case where sufficient reference data cannot be obtained.

It should be noted in this embodiment that the value of the parameter "k" used in the k-nearest neighbor algorithm may be optimally specified by the cross validation. The method of specifying the parameter "k" by the cross validation has already been described in the context of the first embodiment.

Also, the estimation device in accordance with this embodiment may be configured to be capable of executing the estimation method in accordance with the first embodiment. In this case, it is preferable that the estimation method can be selected by a user via the GUI. The estimation device may execute the estimation method selected by the user.

Third Embodiment

A third embodiment is described with reference to FIGS. 59 to 61. This embodiment describes a variant example of the estimation method to estimate the genotype by the k-nearest neighbor algorithm used in the estimation methods in accordance with the first embodiment and the second embodiment.

The foregoing embodiments have been described on the assumption that it is possible to estimate the genotype of the unknown specimen by the k-nearest neighbor algorithm. However, if multiple unknown specimens concentrate at relatively close positions in the clustering map, it may happen that the above-described k-nearest neighbor algorithm cannot estimate the genotypes of the unknown specimens.

Figure 59:
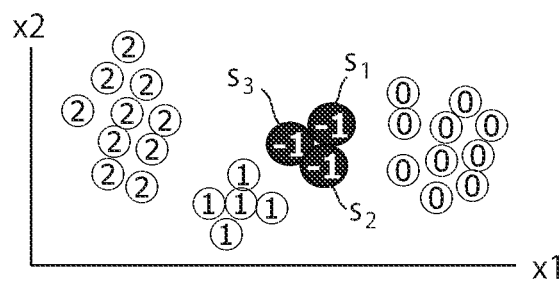
FIG. 59 is a diagram illustrating an exemplary clustering map where multiple unknown specimens are concentrated at locations relatively close to each other.
Figure 60:
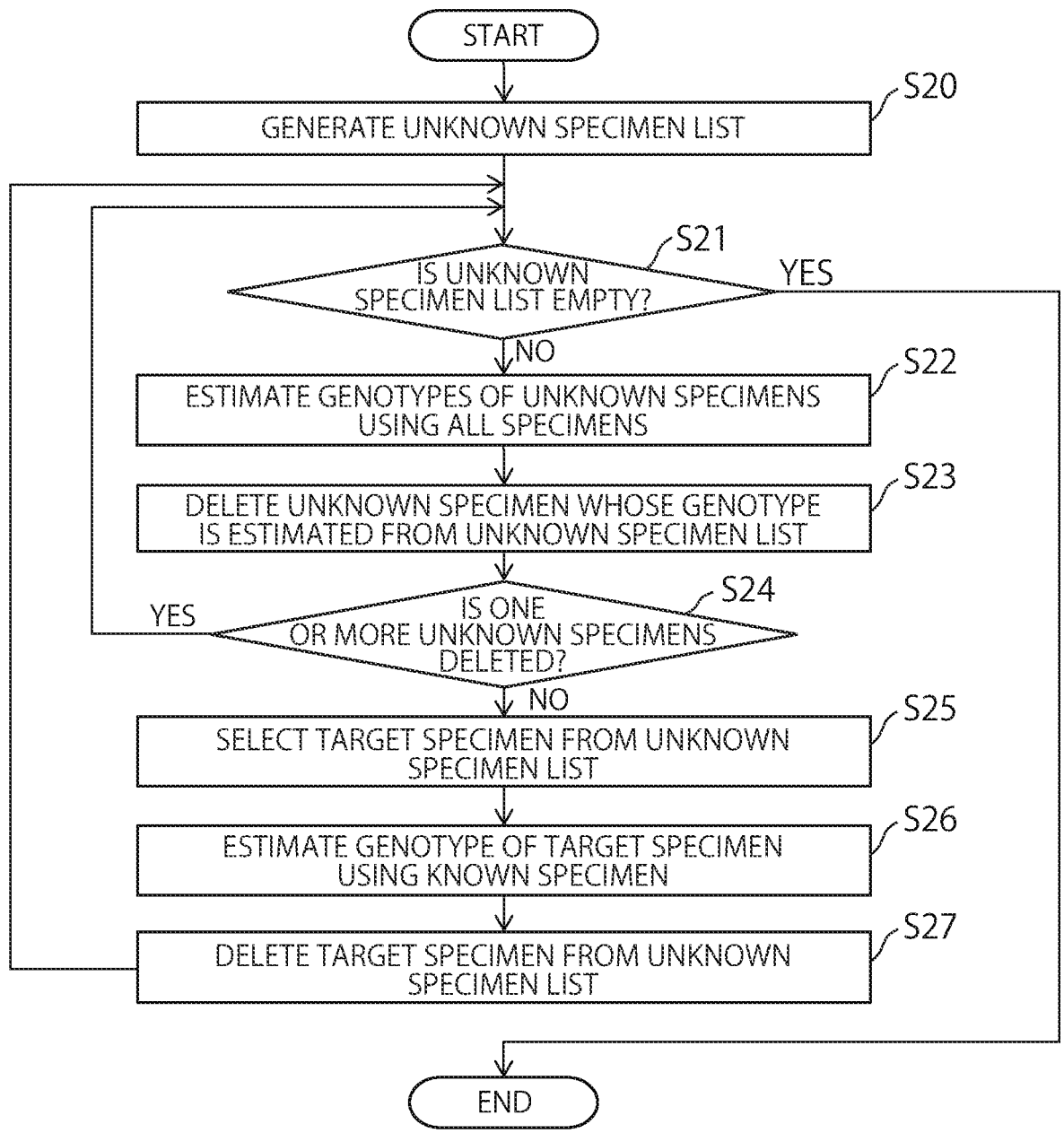
FIG. 60 is a flowchart illustrating a k-nearest neighbor algorithm in accordance with a third embodiment.

FIG. 59 is a diagram that illustrates an example of the clustering map where multiple unknown specimens concentrate at relatively close positions. In FIG. 59, the specimens "$s_1$" to "$s_3$" are unknown specimens, which concentrate at positions close to each other.

In the example of FIG. 59, if there are three parameters "k" of the k-nearest neighbor algorithm, then the specimens "$s_2$" and "$s_3$" of the genotype "−1" and one specimen of the genotype "0" are selected as the three nearest-neighbor specimens closest to the specimen $s_1$. As a result, by the majority voting algorithm, the genotype of the specimen "$s_1$" is estimated as being "−1." Specifically, it is not possible to estimate the genotype of the specimen "$s_1$." For the same reason, it is not possible to estimate the genotypes of the specimen "$s_2$" or "$s_3$."

This embodiment describes a k-nearest neighbor algorithm that can estimate the genotype of the unknown specimen even in such a case. FIG. 60 is a flowchart that illustrates the k-nearest neighbor algorithm in accordance with this embodiment.

In step S20, the estimator 5 generates an unknown specimen list. The unknown specimen list is a list that includes all the unknown specimens of the target SNP.

In step S21, the estimator 5 determines whether or not the unknown specimen list generated in step S20 is empty. If the unknown specimen list is empty (YES in step S21), specifically, if there is no unknown specimen in the target SNP, then the estimator 5 completes the estimation process of estimating the genotype of the unknown specimen by the k-nearest neighbor algorithm.

Meanwhile, if the unknown specimen list is not empty (NO in step S21), specifically, if there is any unknown specimen in the target SNP, then the process proceeds to step S22.

In step S22, the estimator 5 estimates the genotype of the respective unknown specimen included in the unknown specimen list by the k-nearest neighbor algorithm using all the specimens. The estimation of the genotype by the k-nearest neighbor algorithm executed in step S22 has already been described in the context of the first embodiment.

In step S23, the estimator 5 deletes the unknown specimen whose genotype has been estimated in step S22 from the unknown specimen list. The deleted unknown specimen is handled in the subsequent processes as a known specimen.

When one or more unknown specimens have been deleted from the unknown specimen list in step S23 (YES in step S24), the process goes back to step S21. This is because the one or more unknown specimens become a new known specimen or specimens, which may make it possible to estimate the genotype of the unknown specimen whose genotype could not be estimated in step S22.

Thereafter, the processes of steps S21 to S24 are repeated until one or more unknown specimens are deleted from the unknown specimen list (until one or more genotypes of the unknown specimen cease to be estimated in step S22).

Meanwhile, when one or more unknown specimens were not deleted from the unknown specimen list in step S23 (NO in step S24), the process proceeds to step S25. This corresponds, in the k-nearest neighbor algorithm using the all the specimens, to the case where the genotype of the unknown specimen cannot be estimated anymore. Specifically, as has been discussed in the foregoing description, this means that multiple unknown specimens concentrate at relatively close positions.

In step S25, the estimator 5 selects the target specimen from the unknown specimens included in the unknown specimen list. The target specimen as used herein refers to an unknown specimen to be subjected to the genotype estimation. The estimator 5 may randomly select the target specimen(s) or in accordance with the following method.

First, the estimator 5 calculates, with regard to the respective unknown specimens included in the unknown specimen list, an average distance of the distances with respect to the "k" nearest-neighbor known specimens. The estimator 5 then selects, as the target specimen, the unknown specimen whose average distance with respect to the "k" known specimens is the shortest.

In step S26, the estimator 5 estimates the genotype of the target specimen that has been selected in step S25 by the k-nearest neighbor algorithm only using the known specimen. As a result, "k" known specimens are selected as the "k" nearest-neighbor specimens closest to the target specimen. Accordingly, the genotype of the target specimen can be estimated on the basis of the selected genotype of the known specimen.

In step S27, the estimator 5 deletes the target specimen from the unknown specimen list. After that, the process proceeds to step S21. Thereafter, the processes of steps S21 to S27 are repeated until the unknown specimen list becomes empty.

Figure 61:
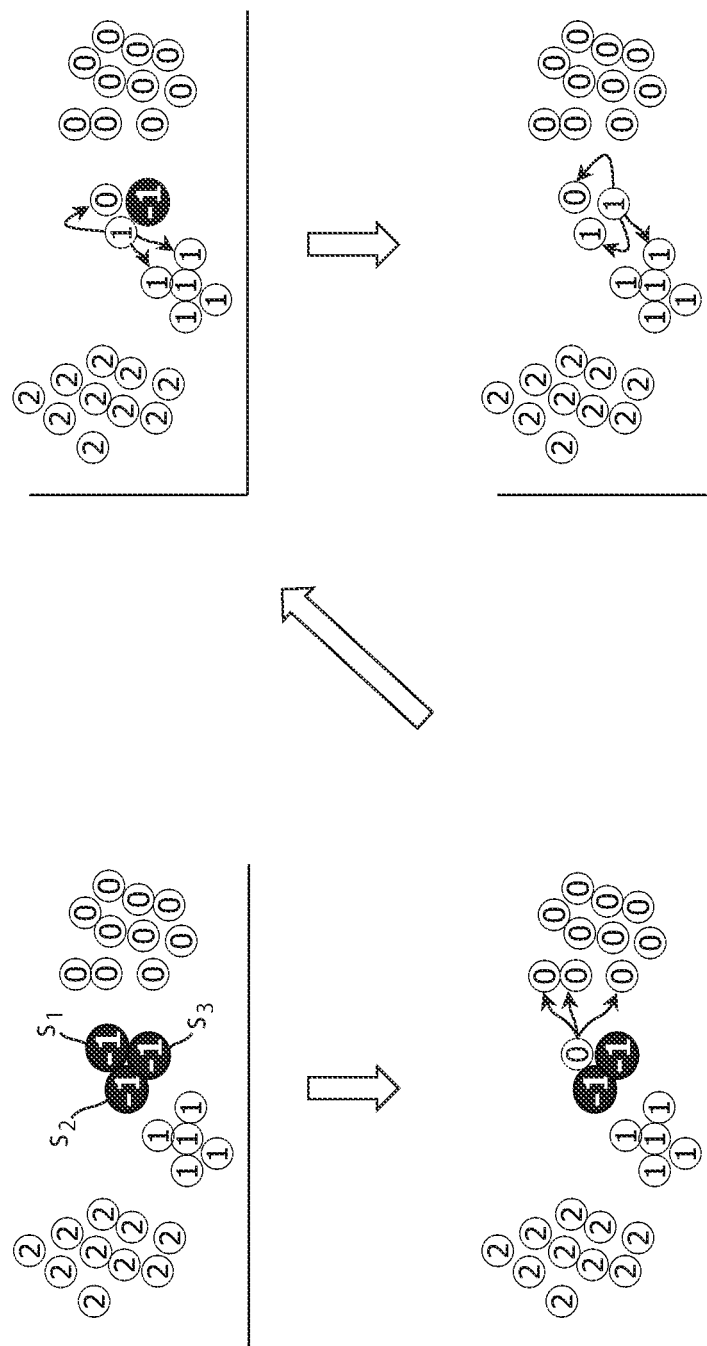
FIG. 61 is a diagram illustrating a clustering map that corresponds to the process of estimating the genotype of the unknown specimen.

FIG. 61 is a diagram that illustrates the clustering map which corresponds to the process of the genotype of the unknown specimen being estimated by the k-nearest neighbor algorithm in accordance with this embodiment. The upper left figure of FIG. 61 corresponds to FIG. 59. For simplified explanation, it is assumed here that the genotypes of the specimens "$s_1$" to "$s_3$" cannot be estimated by the k-nearest neighbor algorithm that uses all the specimens. Also, it is assumed here that the specimens "$s_1$" to "$s_3$" are selected in this order as the target specimens. Further, it is assumed that the parameter "k" is 3.

First, in the first round of the repeated processing, the estimator 5 selects the specimen "$s_1$" as the target specimen (step S25). The estimator 5 then estimates the genotype of the specimen "$s_1$" by the k-nearest neighbor algorithm using the known specimen. In the example of FIG. 61, three known specimens of the genotype 0 are selected as the three nearest-neighbor known specimens closest to the specimen "$s_1$." Accordingly, the estimator 5 estimates, as illustrated in the lower left figure, the genotype of the specimen "$s_1$" as being the genotype 0 (step S26). After that, the estimator 5 deletes the specimen "$s_1$" from the unknown specimen list (step S27). Thereafter, the specimen "$s_1$" becomes a known specimen of the genotype 0.

Next, in the second round of the repeated processing, the estimator 5 selects the specimen "$s_2$" as the target specimen (step S25). The estimator 5 then estimates the genotype of the specimen "$s_2$" by the k-nearest neighbor algorithm using the known specimen. In the example of FIG. 61, two known specimens of the genotype 1 and one known specimen of the genotype 0 (specimen "$s_1$") are selected as three nearest-neighbor known specimens closest to the specimen "$s_2$." Accordingly, the estimator 5 estimates, as illustrated in the upper right figure, the genotype of the specimen "$s_2$" as being the genotype 1 (step S26). After that, the estimator 5 deletes the specimen "$s_2$" from the unknown specimen list (step S27). Thereafter, specimen "$s_2$" becomes the known specimen of the genotype 1.

Further, in the third round of the repeated processing, the estimator 5 selects the specimen "$s_3$" as the target specimen (step S25). Also, the estimator 5 estimates the genotype of the specimen "$s_3$" by the k-nearest neighbor algorithm using the known specimen. In the example of FIG. 61, two known specimens of the genotype 1 (including the specimen "$s_2$") and one known specimen of the genotype 0 (specimen "$s_1$") are selected as three nearest-neighbor known specimens closest to the specimen "$s_3$." Accordingly, the estimator 5 estimates, as illustrated in the lower right figure, the genotype of the specimen "$s_3$" as being the genotype 1 (step S26). After that, the estimator 5 deletes the specimen "$s_3$" from the unknown specimen list (step S27). As a result, the specimen "$s_3$" will be the known specimen the genotype 1.

As has been described in the foregoing, according to the k-nearest neighbor algorithm in accordance with this embodiment, the genotype of the unknown specimen can be estimated even when multiple unknown specimens concentrate at relatively close positions. The k-nearest neighbor algorithm in accordance with this embodiment can be applied to both of the first embodiment and the second embodiment.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A genotype estimation device, comprising:
processing circuitry configured to:
learn a correspondence relationship between a genotype and each of intervals defined by a threshold of a signal intensity on the basis of signal intensities of known specimens which are specimens whose genotypes are known,
wherein the genotype is a combination of two of adenine (A), thymine (T), cytosine (C), and guanine (G), and
wherein the signal intensities are measured by DNA microarray technology and each of the intervals is associated with a different one of the genotypes; and
estimate a genotype of an unknown specimen using a signal intensity of the unknown specimen on the basis of the correspondence relationship, the unknown specimen being a specimen whose genotype is unknown,
wherein
the processing circuitry is configured to learn the correspondence relationship on the basis of a signal intensity of a Fullcall SNP being an SNP in which a genotype is known for all of the specimens, and
wherein the processing circuitry is configured to calculate a statistical value of the signal intensity of a Fullcall SNP for each of the genotypes, and generate a threshold candidate which is a candidate for the threshold on the basis of the statistical value, the Fullcall SNP being an SNP in which a genotype is known for all of the specimens.

2. The genotype estimation device according to claim 1, wherein the processing circuitry is configured to generate a threshold combination being a combination of threshold candidates; estimate the genotype of the Fullcall SNP on the basis of the threshold combination; and calculate an agreement rate between the genotype prior to the estimation and the genotype after the estimation, and
the processing circuitry is configured to learn a correspondence relationship between the genotype and each of the intervals defined by the thresholds included in the threshold combination having a highest agreement rate.

3. The genotype estimation device according to claim 1, wherein the processing circuitry is configured to further estimate a genotype of a Nocall SNP being an SNP in which a genotype is unknown for at least one of the specimens on the basis of the correspondence relationship.

4. The genotype estimation device according to claim 1, wherein the processing circuitry is configured to estimate a genotype of the specimen whose signal intensity is included in a predetermined interval by a k-nearest neighbor algorithm.

5. The genotype estimation device according to claim 1, wherein the processing circuitry is configured to estimate the genotypes of the specimen whose signal intensity is lower than a first the threshold and the specimen whose signal intensity is higher than a second threshold, on the basis of the correspondence relationship, and configured to estimate the genotype of the specimen whose signal intensity is not lower than the first threshold and not higher than the second threshold by a k-nearest neighbor algorithm.

6. A genotype estimation device, comprising:
processing circuitry configured to:
- learn a correspondence relationship between a genotype and each of intervals defined by a threshold of a signal intensity on the basis of signal intensities of known specimens which are specimens whose genotypes are known,
  - wherein the genotype is a combination of two of adenine (A), thymine (T), cytosine (C), and guanine (G), and
  - wherein the signal intensities are measured by DNA microarray technology and each of the intervals is associated with a different one of the genotypes; and
- estimate a genotype of an unknown specimen using a signal intensity of the unknown specimen on the basis of the correspondence relationship, the unknown specimen being a specimen whose genotype is unknown, wherein
the processing circuitry is configured to learn the correspondence relationship on the basis of a signal intensity of a Fullcall SNP being an SNP in which a genotype is known for all of the specimens, and
wherein the processing circuitry is configured to associate the interval with the genotype on the basis of an average value of the signal intensity of the Fullcall SNP.

7. A genotype estimation method comprising:
learning a correspondence relationship between a genotype and each of intervals defined by a threshold of a signal intensity on the basis of signal intensities of known specimens which are specimens whose genotypes are known,
- wherein the genotype is a combination of two of adenine (A), thymine (T), cytosine (C), and guanine (G), and
- wherein the signal intensities are measured by DNA microarray technology and each of the intervals correspond to a different one of the genotypes; and
estimating a genotype of an unknown specimen using a signal intensity of the unknown specimen on the basis of the correspondence relationship, the unknown specimen being a specimen whose genotype is unknown;
learning the correspondence relationship on the basis of a signal intensity of a Fullcall SNP being an SNP in which a genotype is known for all of the specimens; and
calculating a statistical value of the signal intensity of a Fullcall SNP for each of the genotypes, and generate a threshold candidate which is a candidate for the threshold on the basis of the statistical value, the Fullcall SNP being an SNP in which a genotype is known for all of the specimens.

8. A non-transitory computer readable medium having a computer program stored therein which causes a computer to execute processing of steps comprising:
learning a correspondence relationship between a genotype and each of intervals defined by a threshold of a signal intensity on the basis of signal intensities of known specimens which are specimens whose genotypes are known,
- wherein the genotype is a combination of two of adenine (A), thymine (T), cytosine (C), and guanine (G), and
- wherein the signal intensities are measured by DNA microarray technology and each of the intervals correspond to a different one of the genotypes; and
estimating a genotype of an unknown specimen using a signal intensity of the unknown specimen on the basis of the correspondence relationship, the unknown specimen being a specimen whose genotype is unknown;
learning the correspondence relationship on the basis of a signal intensity of a Fullcall SNP being an SNP in which a genotype is known for all of the specimens; and
calculating a statistical value of the signal intensity of a Fullcall SNP for each of the genotypes, and generate a threshold candidate which is a candidate for the threshold on the basis of the statistical value, the Fullcall SNP being an SNP in which a genotype is known for all of the specimens.

9. A genotype estimation device comprising: processing circuitry configured to:
learn a correspondence relationship between a genotype and each of intervals defined by a threshold of a signal intensity on the basis of signal intensities of known specimens which are specimens whose genotypes are known,
- wherein the genotype is a combination of two of adenine (A), thymine (T), cytosine (C), and guanine (G), and
- wherein the signal intensities are measured by DNA microarray technology and each of the intervals is associated with a different one of the genotypes; and
estimate a genotype of an unknown specimen using a signal intensity of the unknown specimen on the basis of the correspondence relationship, the unknown specimen being a specimen whose genotype is unknown;
wherein the processing circuitry is configured to estimate the genotypes of the specimen whose signal intensity is lower than a first threshold and the specimen whose signal intensity is higher than a second threshold, on the basis of the correspondence relationship, and configured to estimate the genotype of the specimen whose signal intensity is not lower than the first threshold and not higher than the second threshold by a k-nearest neighbor algorithm.

10. A genotype estimation method, comprising:
learning a correspondence relationship between a genotype and each of intervals defined by a threshold of a signal intensity on the basis of signal intensities of known specimens which are specimens whose genotypes are known,
- wherein the genotype is a combination of two of adenine (A), thymine (T), cytosine (C), and guanine (G), and
- wherein the signal intensities are measured by DNA microarray technology and each of the intervals is associated with a different one of the genotypes;
estimating a genotype of an unknown specimen using a signal intensity of the unknown specimen on the basis of the correspondence relationship, the unknown specimen being a specimen whose genotype is unknown;
learning the correspondence relationship on the basis of a signal intensity of a Fullcall SNP being an SNP in which a genotype is known for all of the specimens; and
associating the interval with the genotype on the basis of an average value of the signal intensity of the Fullcall SNP.

11. A genotype estimation method comprising:
  learning a correspondence relationship between a genotype and each of intervals defined by a threshold of a signal intensity on the basis of signal intensities of known specimens which are specimens whose genotypes are known,
    wherein the genotype is a combination of two of adenine (A), thymine (T), cytosine (C), and guanine (G), and
    wherein the signal intensities are measured by DNA microarray technology and each of the intervals is associated with a different one of the genotypes;
  estimating a genotype of an unknown specimen using a signal intensity of the unknown specimen on the basis of the correspondence relationship, the unknown specimen being a specimen whose genotype is unknown; and
  estimating the genotypes of the specimen whose signal intensity is lower than a first the threshold and the specimen whose signal intensity is higher than a second threshold, on the basis of the correspondence relationship, and configured to estimate the genotype of the specimen whose signal intensity is not lower than the first threshold and not higher than the second threshold by a k-nearest neighbor algorithm.

12. A non-transitory computer readable medium having a computer program stored therein which causes a computer to execute processing of steps comprising:
  learning a correspondence relationship between a genotype and each of intervals defined by a threshold of a signal intensity on the basis of signal intensities of known specimens which are specimens whose genotypes are known,
    wherein the genotype is a combination of two of adenine (A), thymine (T), cytosine (C), and guanine (G), and
    wherein the signal intensities are measured by DNA microarray technology and each of the intervals is associated with a different one of the genotypes;
  estimating a genotype of an unknown specimen using a signal intensity of the unknown specimen on the basis of the correspondence relationship, the unknown specimen being a specimen whose genotype is unknown;
  learning the correspondence relationship on the basis of a signal intensity of a Fullcall SNP being an SNP in which a genotype is known for all of the specimens; and
  associating the interval with the genotype on the basis of an average value of the signal intensity of the Fullcall SNP.

13. A non-transitory computer readable medium having a computer program stored therein which causes a computer to execute processing of steps comprising:
  learning a correspondence relationship between a genotype and each of intervals defined by a threshold of a signal intensity on the basis of signal intensities of known specimens which are specimens whose genotypes are known,
    wherein the genotype is a combination of two of adenine (A), thymine (T), cytosine (C), and guanine (G), and
    wherein the signal intensities are measured by DNA microarray technology and each of the intervals is associated with a different one of the genotypes;
  estimating a genotype of an unknown specimen using a signal intensity of the unknown specimen on the basis of the correspondence relationship, the unknown specimen being a specimen whose genotype is unknown; and
  estimating the genotypes of the specimen whose signal intensity is lower than a first the threshold and the specimen whose signal intensity is higher than a second threshold, on the basis of the correspondence relationship, and configured to estimate the genotype of the specimen whose signal intensity is not lower than the first threshold and not higher than the second threshold by a k-nearest neighbor algorithm.

* * * * *